US006025355A

United States Patent [19]
Reddy et al.

[11] Patent Number: 6,025,355
[45] Date of Patent: Feb. 15, 2000

[54] PHARMACEUTICALLY ACTIVE COMPOUNDS AND METHODS OF USE

[75] Inventors: N. Laxma Reddy, Lexington; Michael Maillard; David Berlove, both of Cambridge; Sharad Magar, Somerville; Graham J. Durant, Wellesley Hills, all of Mass.

[73] Assignee: Cambridge NeuroScience, Inc., Cambridge, Mass.

[21] Appl. No.: 08/858,399

[22] Filed: May 19, 1997

Related U.S. Application Data

[63] Continuation-in-part of application No. 08/601,992, filed as application No. PCT/US97/02678, Feb. 14, 1997, abandoned.

[51] Int. Cl.⁷ .................. A61K 31/495; A61K 31/535; A61K 31/54; C07D 279/16
[52] U.S. Cl. .................. 514/224.2; 514/230.5; 514/249; 514/311; 544/51; 544/162; 544/165; 544/349; 546/176
[58] Field of Search .................. 514/224.2, 230.5, 514/249, 311; 544/51, 162, 165, 349; 546/176

[56] References Cited

U.S. PATENT DOCUMENTS

| | | | |
|---|---|---|---|
| 2,633,474 | 3/1953 | Beaver | 260/565 |
| 2,704,710 | 3/1955 | Sprung | 95/2 |
| 3,119,831 | 1/1964 | Homer | 260/296 |
| 3,121,645 | 2/1964 | Bindler et al. | 117/138.5 |
| 3,122,555 | 2/1964 | Janssen | 260/292.4 |
| 3,140,231 | 7/1964 | Luskin et al. | 167/65 |
| 3,159,676 | 12/1964 | Spickett et al. | 260/564 |
| 3,168,562 | 2/1965 | Walton et al. | 260/564 |
| 3,200,151 | 8/1965 | Spickett et al. | 260/564 |
| 3,228,975 | 1/1966 | Abraham et al. | 260/501 |
| 3,248,426 | 4/1966 | Dvornil | 260/564 |
| 3,252,861 | 5/1966 | Mull | 167/65 |
| 3,256,278 | 6/1966 | Petracek | 260/247.5 |
| 3,270,054 | 8/1966 | Gagneux et al. | 260/564 |
| 3,283,003 | 11/1966 | Jack et al. | 260/564 |

(List continued on next page.)

FOREIGN PATENT DOCUMENTS

| | | |
|---|---|---|
| 1081711 | 7/1980 | Canada . |
| 0 035 374 | 9/1981 | European Pat. Off. . |
| 0 179 642 | 4/1986 | European Pat. Off. . |
| 0 235 942 | 9/1987 | European Pat. Off. . |
| 0 266 574 | 5/1988 | European Pat. Off. . |
| 0 296 560 | 12/1988 | European Pat. Off. . |
| 0 372 934 | 6/1990 | European Pat. Off. . |
| 0 501 552 | 9/1992 | European Pat. Off. . |
| 1473839 | 6/1967 | France . |
| 3108564 | 11/1982 | Germany . |
| 92/0990 | 11/1992 | South Africa . |
| 92/0944 | 10/1993 | South Africa . |
| 94/9253 | 3/1996 | South Africa . |
| 966493 | 8/1964 | United Kingdom . |
| WO 90/14067 | 11/1990 | WIPO . |
| WO 92/19621 | 11/1992 | WIPO . |
| WO94/22807 | 10/1994 | WIPO . |
| WO 94/27591 | 12/1994 | WIPO . |
| WO 95/14467 | 6/1995 | WIPO . |
| WO 95/20950 | 8/1995 | WIPO . |
| WO 9520950 | 8/1995 | WIPO . |
| WO 96/17612 | 6/1996 | WIPO . |

OTHER PUBLICATIONS

R.N. Gano et al., *J. Amer. Chem. Soc.*, 74:3176–3177 (1952).
V.F. Vasil'eva et al. *Chemical Abstracts*, 89:575 (1978).
N. Laxma Reddy et al. *J. Med. Chem.*, 37:260–267 (1994).
Hughes et al., J. Med. Chem. 18(11), 1077–88 1975.
Vasil'eva et al., Khim–Farm, Zh., 12(8), 40–5 1978.
J. Mosinger et al., *Experimental Neurology*, 113:10–17 (1991).
Y. Yoon et al., *Arch. Ophthalmol.*, 107:409–411 (1989).
L. Gupta et al., *Arch. Ophthalmol.*, 111:384–388 (1993).
Doull et al., *A Survey of Compounds for Radiation Protection* (USAF Radiation Laboratory). (1978).
Database Crossfire, Beilsteninformationsysteme GmbH, BRN 3095078, 3094377, 3093029, *J. Org. Chem. USSR*, 4:459 (1968).
Database Crossfire, Beilsteninformationsysteme GmbH, BRN 2938786, *Curr. Sci.*, 45:764 (1976).
Database Crossfir, Beilsteninformationsysteme GmbH, BRN 3430469, *Yuki Gosei Kaguku Kykaisha*, 8:38,42 (1950).
K. Miura et al., *Chem. Abstracts*, 109:114,75454d (1988).
P. Vasilev et al., *Chem. Abstracts*, 93:150095u (1980).
S. Ahmad, *Chem. Abstracts*, 108:538, 221382b (1988).
A. Ginsburg et al., *Chem. Abstracts*, 57:4518d (1962).
G. Durant et al., *J. Med. Chem.*, 9:22–27 (1966).
C. Kroger et al., *Ber.*, 97:396–404 (1964).
E. Podrebarac et al., *J. Med. Chem.*, 6:283–288 (1963).
R. Prasad, *Can. J. Chem.*, 45:2247–2252 (1967).
D. Lloyd et al., *Tetrahedron*, 33:1379–1389 (1977).
H. Shimazu et al., *Chem. Abstracts*, 111(2):16337m (1989).
T Tada et al., *Chem. Abstracts*, 104(24):208252g (1986).
L. Kiselev et al., *Chem. Abstracts*, 91(21):175291b (1979).
A. Heesing et al., *Chem. Abstracts*, 64(11):15776h (1966).
K. Akiba et al., *Bull. Chem. Soc. Jap.*, 47(4):935–937 (1974).

(List continued on next page.)

*Primary Examiner*—Johann Richter
*Assistant Examiner*—John F. Dolan
*Attorney, Agent, or Firm*—Peter F. Corless; Dike, Bronstein, Roberts & Cushman, LLP

[57] ABSTRACT

The present invention relates to pharmaceutically acceptable compounds, including certain substituted indolinyl and derivatives thereof, 1,2,3,4-tetrahydroquinolinyl and derivatives thereof, 1,2,3,4-tetrahydroisoquinolinyl, benz[cd] indolinyl and 5,6-dihydrophenanthridinyl compounds, and methods of treatment and pharmaceutical compositions that utilize or comprise one or more such compounds. Compounds of the invention are particularly useful for the treatment or prophylaxis of neurological injury and neurodegenerative disorders.

40 Claims, No Drawings

U.S. PATENT DOCUMENTS

| | | | |
|---|---|---|---|
| 3,284,289 | 11/1966 | Duerr et al. | 167/30 |
| 3,291,799 | 12/1966 | Wenner et al. | 260/286 |
| 3,301,755 | 1/1967 | Mull | 167/65 |
| 3,305,552 | 2/1967 | Cragoe, Jr. et al. | 260/250 |
| 3,314,963 | 4/1967 | Koch et al. | 260/288 |
| 3,320,229 | 5/1967 | Szabo et al. | 260/96.5 |
| 3,403,156 | 9/1968 | Humber et al. | 260/286 |
| 3,409,669 | 11/1968 | Dyke | 260/564 |
| 3,479,437 | 11/1969 | Szabo et al. | 424/304 |
| 3,527,871 | 9/1970 | Engelhardt et al. | 424/330 |
| 3,547,951 | 12/1970 | Hardie et al. | 260/340.9 |
| 3,597,433 | 8/1971 | Dobson et al. | 260/286 R |
| 3,624,259 | 11/1971 | Galantay | 260/479 R |
| 3,639,477 | 2/1972 | L'Italien | 260/564 A |
| 3,678,109 | 7/1972 | Knowles | 260/564 R |
| 3,679,692 | 7/1972 | Wu et al. | 260/296 B |
| 3,681,459 | 8/1972 | Hughes et al. | 260/565 |
| 3,689,675 | 9/1972 | Knowles | 424/326 |
| 3,723,463 | 3/1973 | Yale et al. | 260/327 B |
| 3,804,898 | 4/1974 | Panneman | 260/564 A |
| 3,812,119 | 5/1974 | Walker | 260/247 |
| 3,822,262 | 7/1974 | Bream et al. | 260/256.4 H |
| 3,888,927 | 6/1975 | Hamakawa et al. | 260/564 R |
| 3,903,163 | 9/1975 | McCarthy, Jr. | 260/564 R |
| 3,906,044 | 9/1975 | Algami et al. | 260/564 R |
| 3,908,013 | 9/1975 | Hughes et al. | 424/258 |
| 3,914,306 | 10/1975 | Douglas et al. | 260/562 R |
| 3,949,089 | 4/1976 | Maxwell et al. | 424/326 |
| 3,965,176 | 6/1976 | Gold | 260/564 RF |
| 3,968,211 | 7/1976 | DuCharme | 424/248 |
| 3,972,931 | 8/1976 | McCarthy, Jr. | 260/564 R |
| 3,975,533 | 8/1976 | Kodama et al. | 424/326 |
| 3,976,643 | 8/1976 | Diamond et al. | 260/247.5 R |
| 3,976,787 | 8/1976 | Hughes et al. | 424/326 |
| 3,983,250 | 9/1976 | Abdallah et al. | 424/326 |
| 3,987,158 | 10/1976 | Hodson | 424/9 |
| 3,988,474 | 10/1976 | Abdallah et al. | 424/326 |
| 4,014,934 | 3/1977 | Hughes et al. | 260/565 |
| 4,051,256 | 9/1977 | Swallow | 424/304 |
| 4,052,455 | 10/1977 | Matier et al. | 260/562 R |
| 4,052,508 | 10/1977 | Anderson et al. | 424/258 |
| 4,060,640 | 11/1977 | Kodama et al. | 424/326 |
| 4,064,139 | 12/1977 | Anderson et al. | 260/313.1 |
| 4,093,655 | 6/1978 | Miller et al. | 260/564 RF |
| 4,109,014 | 8/1978 | Liu et al. | 424/326 |
| 4,130,663 | 12/1978 | Matier et al. | 424/326 |
| 4,134,992 | 1/1979 | Abdallah et al. | 424/326 |
| 4,154,947 | 5/1979 | Goldman et al. | 542/417 |
| 4,161,541 | 7/1979 | Rasmussen | 424/326 |
| 4,284,642 | 8/1981 | Toldy et al. | 424/273 R |
| 4,318,915 | 3/1982 | Cohnen et al. | 424/273 R |
| 4,332,822 | 6/1982 | Ward | 424/324 |
| 4,342,765 | 8/1982 | Jones et al. | 424/249 |
| 4,353,912 | 10/1982 | Neumeyer | 424/258 |
| 4,369,325 | 1/1983 | Toldy et al. | 548/315 |
| 4,374,836 | 2/1983 | Yellin et al. | 424/251 |
| 4,374,838 | 2/1983 | Anderson et al. | 424/256 |
| 4,379,160 | 4/1983 | Harfenist et al. | 424/274 |
| 4,393,077 | 7/1983 | Douglas et al. | 424/326 |
| 4,400,383 | 8/1983 | Davidson et al. | 424/250 |
| 4,465,677 | 8/1984 | DeMarinis et al. | 424/244 |
| 4,470,989 | 9/1984 | Henning et al. | 424/267 |
| 4,471,137 | 9/1984 | Barton et al. | 564/240 |
| 4,504,482 | 3/1985 | Lesher et al. | 514/275 |
| 4,575,514 | 3/1986 | Carson | 514/542 |
| 4,649,222 | 3/1987 | Georgiev et al. | 564/459 |
| 4,680,300 | 7/1987 | Nelson et al. | 514/312 |
| 4,709,094 | 11/1987 | Weber et al. | 564/238 |
| 4,742,054 | 5/1988 | Naftchi | 514/215 |
| 4,778,812 | 10/1988 | Jirkovsky | 514/323 |
| 4,780,466 | 10/1988 | Hrib et al. | 514/254 |
| 4,789,673 | 12/1988 | Donatsch et al. | 514/214 |
| 4,833,138 | 5/1989 | Olney | 514/226.2 |
| 4,837,218 | 6/1989 | Olney | 514/646 |
| 4,863,953 | 9/1989 | Leeson et al. | 514/425 |
| 4,866,062 | 9/1989 | Toth et al. | 514/255 |
| 4,866,076 | 9/1989 | Gribble | 514/307 |
| 4,873,262 | 10/1989 | Junge et al. | 514/510 |
| 4,888,347 | 12/1989 | Woodruff et al. | 514/289 |
| 4,898,978 | 2/1990 | Bergfeld et al. | 564/231 |
| 4,906,779 | 3/1990 | Weber et al. | 564/238 |
| 4,918,064 | 4/1990 | Cordi et al. | 514/114 |
| 4,940,789 | 7/1990 | Childers, Jr. et al. | 540/581 |
| 4,945,097 | 7/1990 | Olney | 514/318 |
| 4,962,107 | 10/1990 | Nakamura et al. | 514/237.5 |
| 4,962,115 | 10/1990 | Van Daele | 514/326 |
| 5,011,834 | 4/1991 | Weber et al. | 514/212 |
| 5,089,634 | 2/1992 | Powers et al. | 549/285 |
| 5,093,525 | 3/1992 | Weber et al. | 564/238 |
| 5,190,976 | 3/1993 | Weber et al. | 514/634 |
| 5,231,102 | 7/1993 | Baker et al. | 514/312 |
| 5,262,568 | 11/1993 | Weber et al. | 564/238 |
| 5,308,869 | 5/1994 | Keana et al. | 514/637 |
| 5,312,840 | 5/1994 | Keana et al. | 514/634 |
| 5,336,689 | 8/1994 | Weber et al. | 514/634 |
| 5,384,322 | 1/1995 | Vincent et al. | 514/299 |
| 5,385,946 | 1/1995 | Keana et al. | 514/634 |
| 5,393,760 | 2/1995 | Ackermann et al. | 514/323 |
| 5,403,861 | 4/1995 | Goldin et al. | 514/634 |
| 5,478,863 | 12/1995 | Keana et al. | 514/634 |
| 5,502,255 | 3/1996 | Keana et al. | 564/230 |
| 5,507,974 | 4/1996 | Gompper et al. | 252/299.01 |
| 5,552,443 | 9/1996 | Keana et al. | 514/631 |
| 5,559,154 | 9/1996 | Weber et al. | 514/634 |
| 5,604,228 | 2/1997 | Keana et al. | 514/255 |
| 5,614,630 | 3/1997 | Goldin et al. | 546/159 |
| 5,622,968 | 4/1997 | Goldin et al. | 514/313 |
| 5,637,622 | 6/1997 | Weber et al. | 514/634 |
| 5,637,623 | 6/1997 | Goldin et al. | 514/634 |
| 5,652,269 | 7/1997 | Goldin et al. | 514/632 |
| 5,670,519 | 9/1997 | Goldin et al. | 514/313 |
| 5,672,608 | 9/1997 | Goldin et al. | 514/313 |
| 5,677,348 | 10/1997 | Goldin et al. | 514/634 |
| 5,681,861 | 10/1997 | Goldin et al. | 514/634 |
| 5,686,495 | 11/1997 | Goldin et al. | 514/632 |
| 5,688,789 | 11/1997 | Weber et al. | 514/214 |

OTHER PUBLICATIONS

Database Rtecs, "National Institute of Occupational Safety and Health", RTECS No. MF735000. (1986).

J. Keana et al., *Proc. Natl. Acad. Sci.*, 86:5631–5635 (1989).

S. Siddique et al., *Pakistan journal of Scientific and Industrial Res.*, 30(3):163–181 (1987).

E. Maida et al., *Winer Klinische Wochenschrift*, 90(2):43–48 (1978).

C. Chavkin et al., *Advances in the Biosciences*, 75407–410 (1989).

P. Bhargava et al., *Chem. Abstracts*, 86:598, 189787b (1977).

H. Geluk et al., *J. Med. Chem.*, 12:712–715 (1969).

M. Scherz et al., *J. Med. Chem.*, 33:2421–2429 (1990).

A. Stolyarchuk et al., *Chem. Abstracts*, 86:522–523, 121071h (1977).

T. Weakley et al., *Acta. Cryst.*, 46:2234–2236 (1990).

J. Adams et al., *Eur. J. Pharm.*, 142:61–71 (1987).

B. Campbell et al., *J. Neurosci.*, 9:3380–3391 (1989).

G. Durant et al., *J. Med. Chem.*, 28:1414–1422 (1985).

B. Tester et al., *Society for Neuroscience*, 19th Annual Meeting, 983, 396.17 (1989).

M. Kavanaugh et al., *Proc. Natl. Acad. Sci. USA*, 85:2844–2848 (1988).
E. Weber et al., *Proc. Natl. Acad. Sci. USA*, 83:8784–8788 91986).
C. Maryanoff et al., *J. Org. Chem.*, 51:1882–1884 (1986).

S. Safir et al., *J. Org. Chem.*, 13:924–932 (1948).
F. Sharp et al., *Society for Neuroscience Abstr.*, vol. 18, Abstr. No. 482.3 (1992).
B. Clement et al., *Xenobiotica*, 23(2):155–167 (1993).
Kiselev et al., *Chem. Abstracts*, vol. 66 (1967).

PHARMACEUTICALLY ACTIVE COMPOUNDS AND METHODS OF USE

This application is a 371 of PCT/US97/02678 filed Feb. 14, 1997 which is a continuation-in-part of U.S. application Ser. No. 08/601,992, filed Feb. 15, 1996, now abandoned which application is incorporated herein by reference.

BACKGROUND OF THE INVENTION

1. Field of the Invention

The present invention relates to pharmaceuticially active compounds, including certain substituted indolinyl (and derivatives thereof), 1,2,3,4-tetrahydroquinolinyl (and derivatives thereof), 1,2,3,4-tetrahydroisoquinolinyl, benz[cd]indolinyl and 5,6-dihydrophenanthridinyl compounds, and methods of treatment and pharmaceutical compositions that utilize or comprise one or more such compounds. Compounds of the invention are particularly usefull for the treatment or prophylaxis of neurological injury and neurodegenerative disorders.

2. Background

Nerve cell death (degeneration) can cause potentially devastating and irreversible effects for an individual and may occur e.g. as a result of stroke, heart attack or other brain or spinal chord ischemia or trauma. Additionally, neurodegenerative disorders involve nerve cell death (degeneration) such as Alzheimer's disease, Parkinson's disease, Huntington's disease, Amyotrophic Lateral Sclerosis, Down's Syndrome and Korsakoff's disease.

Therapies have been investigated to treat nerve cell degeneration and related disorders, e.g., by limiting the extent of nerve cell death that may otherwise occur to an individual. See, e.g., N. L. Reddy et al., *J. Med. Chem.*, 37:260–267 (1994); and WO 95/20950.

The compound MK-801 has exhibited good results in a variety of in vivo models of stroke. See B. Meldrum, *Cerbrovascular Brain Metab. Rev.*, 2:27–57 (1990); D. Choi, *Cerbrovascular Brain Vetab. Rev.*, 2:105–147 (1990). See also Merck Index, monograph 3392, 11th ed., 1989. For example, MK-801 exhibits good activity in mouse audiogenic tests, a recognized model for evaluation of neuroprotective drugs. See, e.g. M. Tricklebank et al., *European Journal of Pharmacology*, 167:127–135 (1989); T. Seyfried, *Federation Proceedings*, 38(10):2399–2404 (1979).

However, MK-801 also has shown toxicity and further clinical development of the compound is currently uncertain. See J. W. Olney et al., *Science*, 244:1360–1362 (1989); W. Koek et al., *J. Pharmacol. Exp. Ther.*, 252:349–357 (1990); F. R. Sharp et al., *Society for Neuroscience Abstr.*, abstr. no. 482.3 (1992).

It thus would be highly desirable to have new neuroprotective agents, particularly agents to limit the extent or otherwise treat nerve cell death (degeneration) such as may occur with stroke, heart attack or brain or spinal cord trauma, or to treat neurodegenerative disorders such as Alzheimer's disease, Parkinson's disease, Huntington's disease, Amyotrophic Lateral Sclerosis, Down's Syndrome and Korsakoffs disease.

SUMMARY OF THE INVENTION

In a first aspect, the present invention provides substituted indolinyl and indolinyl derivative compounds of the following Formula I:

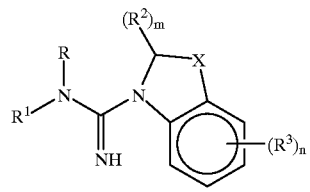

wherein R and $R^1$ are each independently hydrogen; substituted or unsubstituted alkyl having from 1 to about 20 carbon atoms; substituted or unsubstituted alkenyl having from 2 to about 20 carbon atoms; substituted or unsubstituted alkynyl having from 2 to about 20 carbon atoms; substituted or unsubstituted alkoxy having from 1 to about 20 carbon atoms; substituted or unsubstituted alkylthio having from 1 to about 20 carbon atoms; substituted or unsubstituted aminoalkyl having from 1 to about 20 carbon atoms; substituted or unsubstituted alkylsulfinyl having 1 to about 20 carbon atoms; substituted or unsubstituted alkylsulfonyl having 1 to about 20 carbon atoms; substituted or unsubstituted carbocyclic aryl having at least about 6 ring carbon atoms; or a substituted or unsubstituted heteroaromatic or heteroalicyclic group having from 1 to 3 rings, 3 to 8 ring members in each ring and from 1 to 3 hetero atoms, with at least one of R and $R^1$ being other than hydrogen;

each $R^2$ and each $R^3$ (i.e. substituent of the 4, 5, 6 and 7 aromatic ring positions) are each independently hydrogen, halogen, hydroxyl, azido, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted alkylthio having 1 to about 20 carbon atoms, substituted or unsubstituted aklsulfmyl having from 1 to about 20 carbon atoms, substituted or unsubstituted alkylsulfonyl having from 1 to about 20 carbon atoms, substituted or unsubstituted aninoalkylo having from 1 to about 20 carbon atoms, substituted or unsubstituted carbocyclic aryl having at least about 6 ring carbon atoms, or substituted or unsubstituted aralkyl having at least about 6 ring carbon atoms;

X is substituted or unsubstituted methylene (—CH$_2$—), —S— (i.e. 3-benzothiazolinylcarboximidamide compounds), —O— or substituted or unsubstituted —N—, and preferably is substituted or unsubstituted methylene;

m is 0, 1 or 2; n is 0, 1, 2, 3 or 4; and pharmaceutically acceptable salts thereof.

In a further aspect, the invention provides compounds of the following Formula II:

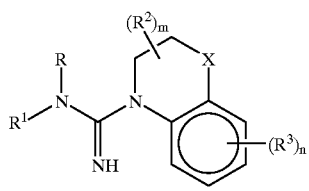

II

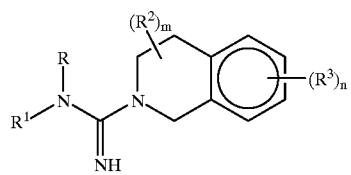

III wherein R and R¹ are each independently hydrogen; substituted or unsubstituted alkyl having from 1 to about 20 carbon atoms; substituted or unsubstituted alkenyl having from 2 to about 20 carbon atoms; substituted or unsubstituted alkynyl having from 2 to about 20 carbon atoms; substituted or unsubstituted alkoxy having from 1 to about 20 carbon atoms; substituted or unsubstituted alkylthio having from 1 to about 20 carbon atoms; substituted or unsubstituted aminoalkyl having from 1 to about 20 carbon atoms; substituted or unsubstituted alkylsulfinyl having 1 to about 20 carbon atoms; substituted or unsubstituted alkylsulfonyl having 1 to about 20 carbon atoms; substituted or unsubstituted carbocyclic aryl having at least about 6 ring carbon atoms; or a substituted or unsubstituted heteroaromatic or heteroalicyclic group having from 1 to 3 rings, 3 to 8 ring members in each ring and from 1 to 3 hetero atoms;

each R² (i.e. substituent of the 2 and 3 ring positions) and each R³ (i.e. substituent of the 5, 6, 7 and 8 aromatic ring positions) are each independently hydrogen, halogen, hydroxyl, azido, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted alkylthio having 1 to about 20 carbon atoms, substituted or unsubstituted aksulfmyl having from 1 to about 20 carbon atoms, substituted or unsubstituted alkylsulfonyl having from 1 to about 20 carbon atoms, substituted or unsubstituted aminoalkyl having from 1 to about 20 carbon atoms, substituted or unsubstituted carbocyclic aryl having at least about 6 ring carbon atoms, or substituted or unsubstituted aralkyl having at least about 6 ring carbon atoms;

X is —O— (i.e. 2,3-benzmorpholinyl compounds), —S— (i.e. 2,3-benzthiomorpholinyl compounds), substituted or unsubstituted —N—, or substituted or unsubstituted methylene (—CH₂—);

m and n are each independently 0 (i.e. the available ring are each hydrogen-substituted), 1, 2, 3 or 4; and pharmaceutically acceptable salts thereof.

In a still further aspect, the invention provides tetrahydroisoquinolinyl compounds of the following Formula III:

wherein R and R¹ are each independently hydrogen; substituted or unsubstituted alkyl having from 1 to about 20 carbon atoms; substituted or unsubstiruted alkenyl having from 2 to about 20 carbon atoms; substituted or unsubstituted alkynyl having from 2 to about 20 carbon atoms; substituted or unsubstituted alkoxy having from 1 to about 20 carbon atoms; substituted or unsubstituted alkylthio having from 1 to about 20 carbon atoms; substituted or unsubstituted alkylthio having from 1 to about 20 carbon atoms; substituted or unsubstituted aminoalkyl having from 1 to about 20 carbon atoms; substituted or unsubstituted alkylsulfinyl having 1 to about 20 carbon atoms; substituted or unsubstituted alkylsulfonyl having 1 to about 20 carbon atoms; substituted or unsubstituted carbocyclic aryl having at least about 6 ring carbon atoms; or a substituted or unsubstituted heteroaromatic or heteroalicyclic group having from 1 to 3 rings, 3 to 8 ring members in each ring and from 1 to 3 hetero atoms;

each R² (i.e. substituent of the 1, 3 and 4 tetrahydroisoquinolinyl ring positions) and each R³ (i.e. substituent of the 5, 6, 7 and 8 tetrahydroisoquinolinyl ring positions) are each independently hydrogen, halogen, hydroxyl, azido, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted alkylthio having 1 to about 20 carbon atoms, substituted or unsubstituted alkylsulfinyl having from 1 to about 20 carbon atoms, substituted or unsubstituted alkylsulfonyl having from 1 to about 20 carbon atoms, substituted or unsubstituted aminoalkyl having from 1 to about 20 carbon atoms, substituted or unsubstituted carbocyclic aryl having at least about 6 ring carbon atoms, or substituted or unsubstituted aralkyl having at least about 6 ring carbon atoms;

m is 0 (i.e. the 1, 3 and 4 tetrahydroisoquinolinyl ring positions are each hydrogen-substituted), 1, 2, 3, 4, 5 or 6; n is 0 (i.e. the 5, 6, 7 and 8 tetrahydroisoquinolinyl ring positions are each hydrogen-substituted), 1, 2, 3 or 4; and pharmaceutically acceptable salts thereof.

In a yet further aspect, the invention provides compounds of the following Formula IV:

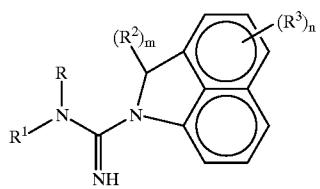

IV

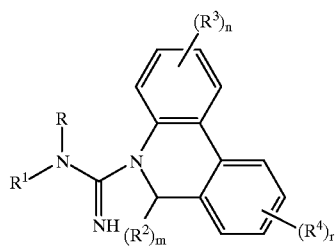

V wherein R and $R^1$ are each independently hydrogen; substituted or unsubstituted alkyl having from 1 to about 20 carbon atoms; substituted or unsubstituted alkenyl having from 2 to about 20 carbon atoms; substituted or unsubstituted alkynyl having from 2 to about 20 carbon atoms; substituted or unsubstituted alkoxy having from 1 to about 20 carbon atoms; substituted or unsubstituted alkylthio having from 1 to about 20 carbon atoms; substituted or unsubstituted aminoalkyl having from 1 to about 20 carbon atoms; substituted or unsubstituted alkylsulfinyl having 1 to about 20 carbon atoms; substituted or unsubstituted alkylsulfonyl having 1 to about 20 carbon atoms; substituted or unsubstituted carbocyclic aryl having at least about 6 ring carbon atoms; or a substituted or unsubstituted heteroaromatic or heteroalicyclic group having from 1 to 3 rings, 3 to 8 ring members in each ring and from 1 to 3 hetero atoms, with at least one of R and $R^1$ being other than hydrogen;

each $R^2$ and each $R^3$ (i.e. substituent of the aromatic positions 3–8) are each independently hydrogen, halogen, hydroxyl, azido, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted alkylthio having 1 to about 20 carbon atoms, substituted or unsubstituted alkylsulfinyl having from 1 to about 20 carbon atoms, substituted or unsubstituted alkylsulfonyl having from 1 to about 20 carbon atoms, substituted or unsubstituted aminoalkyl having from 1 to about 20 carbon atoms, substituted or unsubstituted carbocyclic aryl having at least about 6 ring carbon atoms, or substituted or unsubstituted aralkyl having at least about 6 ring carbon atoms;

m is 0 (i.e. the 2-benz[cd]indolinyl position is hydrogen-substituted), 1 or 2; and n is 0 (i.e. the available ring are each hydrogen-substituted), 1, 2, 3, 4, 5 or 6; and pharmaceutically acceptable salts thereof.

Still further, the invention provides compounds of the following Formula V:

wherein R and $R^1$ are each independently hydrogen; substituted or unsubstituted alkyl having from 1 to about 20 carbon atoms; substituted or unsubstituted alkenyl having from 2 to about 20 carbon atoms; substituted or unsubstituted alkynyl having from 2 to about 20 carbon atoms; substituted or unsubstituted alkoxy having from 1 to about 20 carbon atoms; substituted or unsubstituted alkylthio having from 1 to about 20 carbon atoms; substituted or unsubstituted aminoalkyl having from 1 to about 20 carbon atoms; substituted or unsubstituted alkylsulfinyl having 1 to about 20 carbon atoms; substituted or unsubstituted alkylsulfonyl having 1 to about 20 carbon atoms; substituted or unsubstituted carbocyclic aryl having at least about 6 ring carbon atoms; or a substituted or unsubstituted heteroaromatic or heteroalicyclic group having from 1 to 3 rings, 3 to 8 ring members in each ring and from 1 to 3 hetero atoms, with at least one of R and $R^1$ being other than hydrogen;

each $R^2$, each $R^3$ (i.e. substituent of the aromatic positions 1–4) and each $R^4$ (i.e. substituent of the aromatic positions 7–10) are each independently hydrogen, halogen, hydroxyl, azido, substituted or unsubstituted aLlyl having from 1 to about 20 carbon atoms, substituted or unsubstituted alkenyl having from 2 to about 20 carbon atoms, substituted or unsubstituted allynyl having from 2 to about 20 carbon atoms, substituted or unsubstituted alkoxy having from 1 to about 20 carbon atoms, substituted or unsubstituted alkylthio having 1 to about 20 carbon atoms, substituted or unsubstituted alkylsulfinyl having from 1 to about 20 carbon atoms, substituted or unsubstituted alkylsulfonyl having from 1 to about 20 carbon atoms, substituted or unsubstituted aminoalkyl having from 1 to about 20 carbon atoms, substituted or unsubstituted carbocyclic aryl having at least about 6 ring carbon atoms, or substituted or unsubstituted aralcyl having at least about 6 ring carbon atoms;

m is 0 (i.e. the 5,6-dihydrophenanthridinyl ring position is hydrogen-substituted), 1 or 2; and n and r are each independently 0 (i.e. the ring positions are each hydrogen-substituted), 1, 2, 3 or 4; and pharmaceutically acceptable salts thereof.

In a yet further aspect the invention provides compounds of the following Formulae VI:

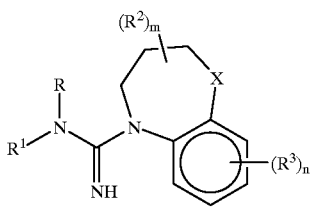

VI wherein R, R$^1$, X, R$^2$, R$^3$ and n are the same as defined above for Formula II, but where X can also be sulfinyl (i.e. —S(O)—) or sulfonyl (i.e. —S(O$_2$)—), and m of Formula VI is an integer equal to 0–6, and preferably m is 0, 1 or 2; and pharmaceutically acceptable salts thereof. Preferred substituents of Formula II also will be preferred substituents at corresponding positions of compounds of of Formula VI.

The invention also provides compounds of the following Formula VII:

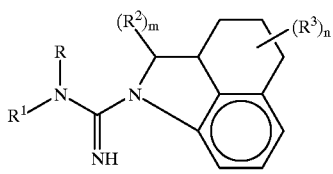

VII wherein R, R$^1$, R$^2$, R$^3$ and m are the same as defined above for Formula IV, and n of Formula VII is an integer equal to 0–9, and preferably n is 0, 1 or 2; and pharmaceutically acceptable salts thereof. It is understood that an R$^3$ substituent can be the same or different and may be present on either the non-aromatic or aromatic fused ring. Preferred substiments of Formula IV also will be preferred substituents at corresponding positions of compounds of Formula VI.

The invention also provides compounds of the following Formula VIII:

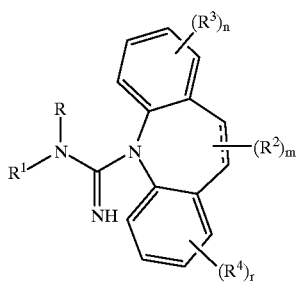

VIII wherein R, R$^1$, R$^2$, R$^3$, n and r are the same as defined above for Formula V, except R and R$^1$ each may be hydrogen, although preferably at least one of R and R$^1$ will be other than hydrogen, and m of Formula VIII is an integer equal to 0–4, and preferably m is 0, 1 or 2, and the dotted line in Formula VIII represents an optional carbon-carbon double bond (endocyclic bond); and pharmaceutically acceptable salts thereof. Preferred substituents of Formula V also will be preferred substituents at corresponding positions of compounds of Formula VIII.

The invention also provides compounds of the following Formula IX:

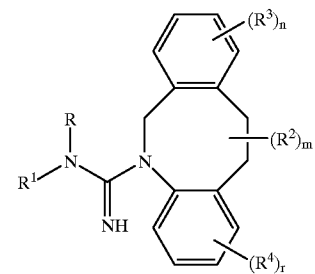

IX wherein R$^2$, R$^3$, n and r are the same as defined above for Formula V; R and R$^1$ are also the same as defined above for Formula V, except R and R$^1$ each may be hydrogen, although preferably at least one of R and R$^1$ will be other than hydrogen; m of Formula IX is an integer equal to 0–6 (i.e. R$^2$ may be a substituent at any of the available three saturated ring positions), and preferably m is 0, 1 or 2

For each of Formulae I, II, III, IV and V, as well as for each of Formulae VI, VII, VII and IX and Formulae I" and II" as defined below, preferably at least one of R and R$^1$ is a carbocyclic aryl, aralkyl, or heteroaromatic or heteroalicyclic group, particularly substituted or unsubstituted phenyl or naphthyl. More preferably, for each of Formulae I through IX (which includes Formulae I" and II"), R is a carbocyclic aryl, heteroaromatic or heteroalicyclic group, and R$^1$ is a non-aryl group, particularly hydrogen or substituted or unsubstituted alkyl, alkoxy, allylthio, alkylsulfinyl, alkylsulfonyl, or aminoalkyl. Substituted or unsubstituted phenyl or naphthyl are preferred R groups of Formulae I through IX (including Formulae I" and II"). Generally more preferred R$^1$ groups are hydrogen and substituted or unsubstituted alkyl such as substituted or unsubstituted alkyl having 1 to about 6 carbon atoms or 1 to about 3 carbon atoms.

The compounds of the invention (i.e. compounds of Formulae I, II, III, IV and V as well as compounds of Formulae I', I", Ia, Iaa, Ib, II", IIa, IIaa, IIb, IIIa. Iaa, IIIb, IVa, IVaa, IVb, Va, Vaa and Vb as discussed below, and as well as compounds of Formulae VI, VII, VIII and IX above) are useful for a number of therapeutic applications. In particular, the invention includes methods for treatment and/or prophylaxis of neurological conditions/injuries such as epilepsy, neurodegenerative conditions and/or nerve cell death (degeneration) resulting from e.g. hypoxia, hypoglycemia, brain or spinal chord ischemia, retinal ischemia, brain or spinal chord trauma or post-surgical neurological deficits and the like as well as neuropathic pain.

The compounds of the invention are especially useful for treatment of a person susceptible or suffering from stroke or heart attack or neurological deficits relating to cardiac arrest, a person suffering or susceptible to brain or spinal cord injury, or a person suffering from the effects of retinal ischemica or degeneration, or a person suffering from decreased blood flow or nutrient supply to retinal tissue or optic nerve or retinal trauma or optic nerve injury. Compounds of the invention also are useful to treat and/or prevent various neurodegenerative diseases such as Parkinson's disease, Huntington's disease, Amyotrophic Lateral Sclerosis, Alzheimer's disease, Down's Syndrome, Korsakoff's disease, cerebral palsy and/or age-dependent dementia. Compounds of the invention will be further useful to treat and/or prevent migraines, shingles (herpes zoster), epilepsy, emesis and/or narcotic withdrawal symptoms. The treatment methods of the invention in general comprise administration of a therapeutically effective amount of one or more compounds of the invention to an animal, including a mammal, particularly a human.

Particularly preferred compounds of the invention exhibit good activity in an anticonvulsant in vivo mouse audiogenic assay e.g. as disclosed in Example 48 which follows, preferably about 20% or more inhibition at a dose of a compound of the invention of 20 mg/kg, more preferably about 50% or more or 70% or more inhibition at a dose of 20 mg/kg in such an anticonvulsant in vivo audiogenic assay.

The invention also provides pharmaceutical compositions that comprise one or more compounds of the invention and a suitable carrier for the compositions.

Other aspects of the invention are disclosed infra.

DETAILED DESCRIPTION OF THE INVENTION

As mentioned above, preferred compounds of Formula I include those where the group X is substituted or unsubstituted methylene, i.e. indolinyl compounds of the following Formula I':

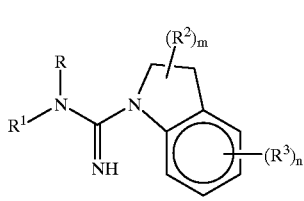

I' where R, $R^1$, $R^2$, $R^3$ and n are each the same as defined above for Formula I; m is 0, 1, 2, 3 or 4; and pharmaceutically acceptable salts thereof.

Preferred compounds of Formula I as defined above include those where R is substituted or unsubstituted carbocyclic aryl, particularly substituted or unsubstituted phenyl, naphthyl and acenaphthyl.

Substituted and unsubstiruted phenyl and naphthyl are particularly preferred R group of compounds of Formula I, such as compounds of the following Formulae Ia and Iaa:

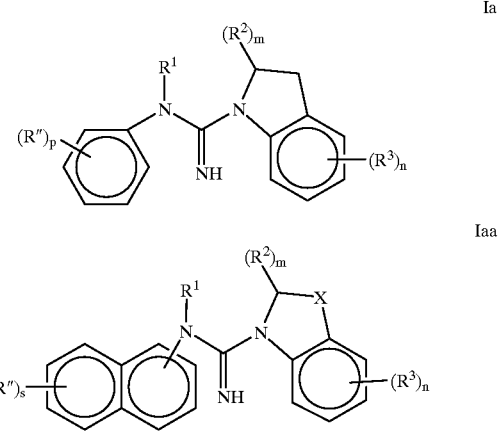

wherein for each of Formulae Ia and Iaa each R" is independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl;

p is an integer of 0 (where the phenyl ring is fully hydrogen substituted), 1, 2, 3, 4 or 5, and more preferably is 1, 2 or 3;

s is an integer of from 0 to 7, and more preferably is 0 (where the naphthyl ring is fully hydrogen-substituted), 1, 2, 3 or 4;

$R^1$, $R^2$, $R^3$, X, m and n are each the same as defined above for Formula I; and pharmaceutically acceptable salts thereof.

Particularly preferred compounds of Formula Ia include those where p is 1 or greater, e.g. compounds that are substituted at the ortho, meta and/or para phenyl ring positions by R" group(s) other than hydrogen, or 2,5-phenyl ring substituted, 2,3,5-phenyl ring substituted or 2,4,5-phenyl ring substituted by R" groups other than hydrogen(s) such as halogen, substituted or unsubstituted alkyl having 1 to about 6 carbon atoms, substituted or unsubstituted alkoxy having 1 to about 6 carbon atoms, or substituted or unsubstituted alkvlthio having 1 to about 6 carbon atoms. It is of course understood that where a phenyl or napthyl group of Formulae Ia or Iaa is not substituted by an R" group, the ring position is hydrogen-substituted. While as shown by the above structure Formula Iaa includes compounds that have either a 1-naphthyl or 2-naphthyl amino (—N($R^1$)—) substituent, compounds having a 1-naphthyl group are generally more preferred. Compounds of Formula Iaa that have a non-hydrogen R" substituent at the 4-naphthyl position are also particularly preferred.

Compounds of Formula I may suitably contain one or more indolinyl (or derivative) ring substituents, i.e. the sum of the values of m and n of Formula I is one or more. It is understood that references herein to "derivatives" of indolinyl compounds of Formula I refer to those compounds where the group X is other than substituted or unsubstituted methylene.

Generally preferred compounds of Formula I that include indolinyl (or derivative) substituents contain no more than one or two non-hydrogen $R^2$ substituents, such as compounds that contain 0 (i.e. ring position 2 is —$CH_2$—) or 1 (i.e. ring position 2 is —$CH_2$—) non-hydrogen $R^2$ substituents. Similarly, generally preferred compounds of Formula I' that include indolinyl ring substitutents contain no more than two or three non-hydrogen $R^2$ substitutents, such as compounds that contain 0 (i.e. each of ring positions 2 and 3 is —$CH_2$—) or 1 (i.e. one indolinyl ring position is —$CH_2$— and the other is —CH($R^2$)—) non-hydrogen $R^2$ substituents.

Generally preferred compounds of Formula I also include those that contain 0 (ring positions 4–7 each hydrogen substituted), and 1 or 2 $R^3$ ring substituents.

Preferred compounds of Formula I also include those compounds that are unsubstituted on the ring (each m and n as defined above for Formula I is 0), i.e. compounds of the following Formula Ib:

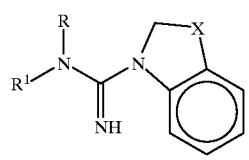

wherein the groups R, $R^1$ and X are the same as defined above for Formula I; and pharmaceutically salts thereof. The above noted preferred R and $R^1$ groups of Formula I are also preferred groups of compounds of Formula Ib.

In another aspect, compounds of Formula I" are provided, which is defined the same as Formula I above, but where X is sulfinyl (i.e. —S(O)—) or sulfonyl (i.e. —S($O_2$)—). Preferred substitutents of compounds of Formula I as noted herein are also preferred substituents for corresponding positions for compounds of Formula I".

Preferred compounds of Formula II include those where R is substituted or unsubstituted carbocyclic aryl such as substituted or unsubstituted phenyl, naphthyl or acenaphthyl, particularly substituted or unsubstituted phenyl or naphthyl, i.e. compounds of the following Formulae IIa and IIaa:

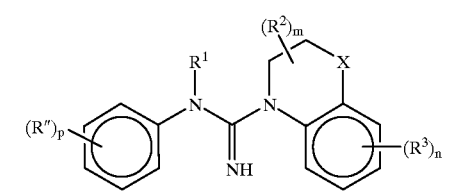

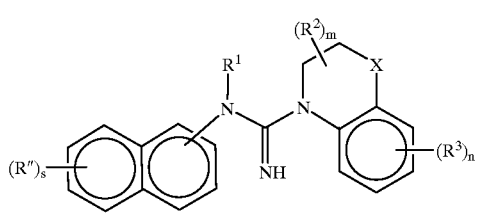

wherein for each of Formulae IIa and IIaa each R" is independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl;

p is an integer of 0 (where the phenyl ring is fully hydrogen substituted), 1, 2, 3, 4 or 5, and more preferably is 1, 2 or 3;

s is an integer of from 0 to 7, and more preferably is 0 (i.e. where the naphthyl ring is fully hydrogen-substituted), 1, 2, 3 or 4;

$R^1$, $R^2$, $R^3$, X, m and n are each the same as defined above for Formula II; and pharmaceutically acceptable salts thereof.

Particularly preferred compounds of Formula IIa include those where p is 1 or greater, e.g. compounds that are substituted at the ortho, meta and/or para phenyl ring positions by R" group(s) other than hydrogen, or 2,5-phenyl ring substituted, 2,3,5-phenyl ring substituted or 2,4,5-phenyl ring substituted by non-hydrogen R" groups such as halogen, substituted or unsubstiruted alkyl having 1 to about 6 carbon atoms, substituted or unsubstituted alkoxy having 1 to about 6 carbon atoms, or substituted or unsubstituted alkylthio having 1 to about 6 carbon atoms. It is of course understood that where a phenyl or napthyl group of Formulae IIa or IIaa is not substituted by an R" group, the ring position is hydrogen-substituted. While as shown by the above structure Formula IIaa includes compounds that have either a 1-naphthyl or 2-naphthyl amino (—N($R^1$)—) substiruent, compounds having a 1-naphthyl group are generally more preferred. Compounds of Formula IIaa that have a non-hydrogen R" substituent at the 4-naphthyl position are also particularly preferred.

Compounds of Formula II may suitably contain one or more tetrahydroquinolinyl (or derivative thereof) ring substituents, i.e. the sum of the values of m and n of Formula II is one or more. It is understood that references herein to "derivatives" of tetrahydroquinolinyl compounds of Formula II refer to those compounds where the group X is other than substituted or unsubstituted methylene.

Generally preferred compounds of Formula II that include tetrahydroquinolinyl (or derivative thereof) ring substituents contain no more than about three non-hydrogen $R^2$ substituents, including compounds that contain 0 (i.e. each of tetrahydroquinolinyl ring positions 2, 3 and 4 is —$CH_2$—) or 1 (i.e. two ring positions is —$CH_2$— and the other is —CH($R^1$)—) $R^2$ substituents. Generally preferred compounds also include those that contain 0 (ring positions 5–8 each hydrogen substituted), 1 or 2 non-hydrogen $R^3$ ring substituents.

Preferred compounds of Formula II also include those that are unsubstituted on the tetrahydroquinolinyl (or derivative thereof) ring, i.e. m and n or Formula II are each 0, particularly compounds of the following Formula IIb:

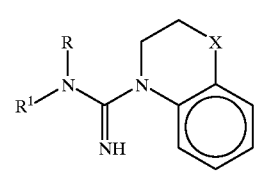

where R and $R^1$ are the same as defined above for Formula II; and pharmaceutically acceptable salts thereof. The above noted preferred R and $R^1$ groups of Formula II are also preferred groups of compounds of Formula IIb.

In another aspect, compounds of Formula II" are provided, which is defined the same as Formula II above, but where X is sulfinyl (i.e. —S(O)—) or sulfonyl (i.e. —S($O_2$)—). Preferred substitutents of compounds of Formula II as noted herein are also preferred substituents for corresponding positions for compounds of Formula II".

Preferred compounds of Formula III include those where R is substituted or unsubstituted carbocyclic aryl such as substituted or unsubstituted phenyl, naphthyl or acenaphthyl, particularly substituted or unsubstituted phenyl or naphthyl, i.e. compounds of the following Formulae IIIa and IIIaa:

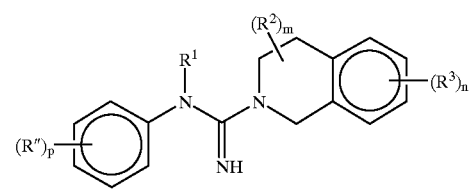

IIIa

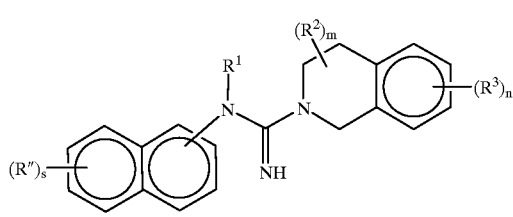

IIIaa wherein for each of Formulae IIIa and IIIaa each R" is independently hydrogen, halogen, hydroxyl, azido, substituted or unsubstituted alkyl, substituted or unsubstituted alkenyl, substituted or unsubstituted allynyl, substituted or unsubstituted alkoxy, substituted or unsubstituted alkylthio, substituted or unsubstituted alkylsulfmyl, substituted or unsubstituted alkylsulfonyl, substituted or unsubstituted aminoalkyl, substituted or unsubstituted carbocyclic aryl, or substituted or unsubstituted aralkyl;

p is an integer of 0 (where the phenyl ring is fully hydrogen substituted), 1, 2, 3, 4 or 5, and more preferably is 1, 2 or 3;

s is an integer of from 0 to 7, and more preferably is 0 (i.e. where the naphthyl ring is fully hydrogen-substituted), 1, 2, 3 or 4;

$R^1$, $R^2$, $R^3$, m and n are each the same as defined above for Formula III; and pharmaceutically acceptable salts thereof.

Particularly preferred compounds of Formula IIIa include those where p is 1 or greater, e.g. compounds that are substituted at the ortho, meta and/or para phenyl ring positions by R" group(s) other than hydrogen, or 2,5-phenyl ring substituted, 2,3,5-phenyl ring substituted or 2,4,5-phenyl ring substituted by non-hydrogen R" groups such as halogen, substituted or unsubstitted alkyl having 1 to about 6 carbon atoms, substituted or unsubstituted alkoxy having 1 to about 6 carbon atoms, or substituted or unsubstituted alkylthio having 1 to about 6 carbon atoms. It is of course understood that where a phenyl or napthyl group of Formulae IIIa or IIIaa is not substituted by an R" group, the ring position is hydrogen-substituted. While as shown by the above structure Formula ffaa includes compounds that have either a 1-naphthyl or 2-naphthyl amino (—N($R^1$)—) substituent, compounds having a 1-naphthyl group are generally more preferred. Compounds of Formula IIIaa that have a non-hydrogen R" substituent at the 4-naphthyl position are also particularly preferred.

Compounds of Formula III may suitably contain one or more tetrahydroisoquinolinyl ring substituents, i.e. the sum of the values of m and n of Formula III is one or more.

Generally preferred compounds of Formula III that include tetrahydroisoquinolinyl ring substituents contain no more than about three non-hydrogen $R^2$ substituents, including compounds that contain 0 (i.e. each of tetrahydroisoquinolinyl ring positions 1, 3 and 4 is —$CH_2$—) or 1 (i.e. two ring positions are —$CH_2$— and the other is —CH($^2$)—)

non-hydrogen $R^2$ substituents. Generally preferred compounds also include those that contain 0 (ring positions 5–8 each hydrogen substituted), 1 or 2 non-hydrogen $R^3$ ring substituents.

Preferred compounds of Formula III also include those that are unsubstituted on the tetrahydroisoquinolinyl ring, i.e. m and n or Formula III are each 0, particularly compounds of the following Formula IIIb:

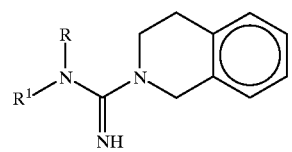

IIIb where R and $R^1$ are the same as defined above for Formula II; and pharmaceutically acceptable salts thereof. The above noted preferred R and $R^1$ groups of Formula III are also preferred groups of compounds of Formula IIIb.

Preferred compounds of Formula IV as defined above include those where R is substituted or unsubstituted carbocyclic aryl, particularly substituted or unsubstituted phenyl, naphthyl and acenaphthyl.

Substituted and unsubstituted phenyl and naphthyl are particularly preferred R groups of compounds of Formula IV, such as compounds of the following Formulae IVa and IVaa:

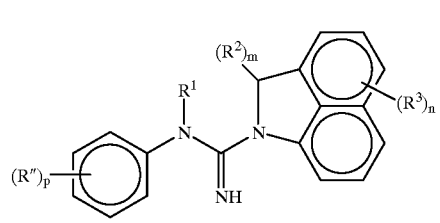

IVa

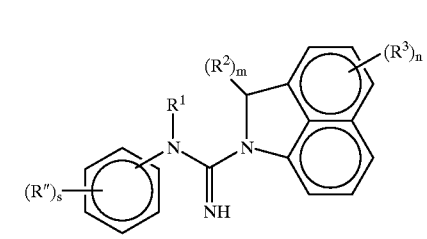

IVaa wherein for each of Formulae IVa and IVaa each R" is independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfmyl, substituted or unsubstituted alkylsulfonyl, substituted or unsubstituted arninoalkl, substituted or unsubstituted carbocyclic aryl, or substituted or unsubstituted aralkyl;

p is an integer of 0 (where the phenyl ring is fully hydrogen substituted), 1, 2, 3, 4 or 5, and more preferably is 1, 2 or 3;

s is an integer of from 0 to 7, and more preferably is 0 (i.e. where the naphthyl ring is fully hydrogen-substituted), 1, 2, 3 or 4;

$R^1$, $R^2$, $R^3$, m and n are each as defined above for Formula IV; and pharmaceutically acceptable salts thereof.

Preferred compounds of Formula IVa include those where p is 1 or greater, e.g. compounds that are substituted at the ortho, meta and/or para phenyl ring positions by R" group(s) other than hydrogen, or 2,5-phenyl ring substituted, 2,3,5-phenyl ring substituted or 2,4,5-phenyl ring substituted by non-hydrogen R" groups such as halogen, substituted or unsubstiruted alkyl having 1 to about 6 carbon atoms, substituted or unsubstituted alkoxy having 1 to about 6 carbon atoms, or substituted or unsubstituted alkylthio having 1 to about 6 carbon atoms. It is of course understood that where a phenyl or napthyl group of Formulae IVa or IVaa is not substituted by an R" group, the ring position is hydrogen-substituted. While as shown by the above structure Formula IVaa includes compounds that have either a 1-naphthyl or 2-naphthyl amino substituent, compounds having a 1-naphthyl group are generally more preferred. Compounds of Formula IVaa that have a non-hydrogen R" substituent at the 4-naphthyl position are also particularly preferred.

Compounds of Formula IV may suitably contain one or more benzindolinyl ring substituents, i.e. the sum of the values of m and n of Formula IV is one or more.

Generally preferred compounds of Formula IV that include benzindolinyl ring substituents contain 0 $R^2$ substituents (i.e. the 2 benz[cd]indolinyl positions is —$CH_2$—), or 1 non-hydrogen $R^2$ substituent.

Generally preferred compounds of Formula IV also include those that contain 0 (i.e. benz[cd]indolinyl ring positions 3–8 each hydrogen substituted), 1 or 2 $R^3$ ring substituents.

Preferred compounds of Formula IV also include those compounds that are unsubstituted on the benzindolinyl ring (each m and n as defined above for Formula IV is 0), i.e. compounds of the following Formula IVb:

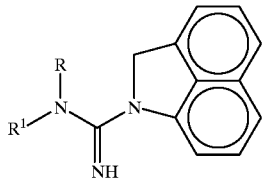

IVb wherein the groups R and $R^1$ are the same as defmed above for Formula III; and pharmaceutically salts thereof. The above noted preferred R and $R^1$ groups of Formula IV are also preferred R and $R^1$ groups of compounds of Formula IVb.

Preferred compounds of Formula V include those where R is substituted or unsubstituted carbocyclic aryl such as substituted or unsubstituted phenyl, naphthyl or acenaphthyl, particularly substituted or unsubstituted phenyl or naphthyl, such as compounds of the following Formulae Va and Vaa:

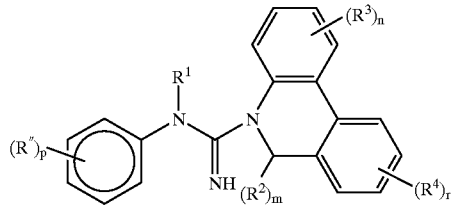

Va

-continued

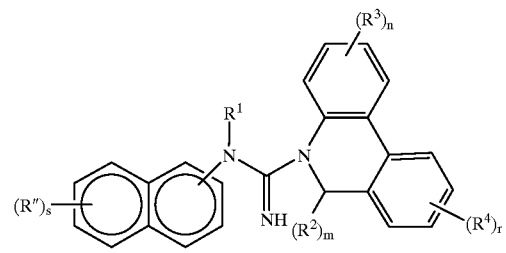

Vaa wherein for each of Formulae Va and Vaa each R" is independenly hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted arninoalkyl, substituted or unsubstituted carbocyclic aryl, or substituted or unsubstituted aralkyl;

p is an integer of 0 (where the phenyl ring is fully hydrogen substituted), 1, 2, 3, 4 or 5, and more preferably is 1, 2 or 3;

s is an integer from 0 to 7, and more preferably is 0 (i.e. where the naphthyl ring is fully hydrogen-substituted), 1, 2, 3 or 4;

$R^1$, $R^2$, $R^3$, $R^4$, m, n and r are each as defmed above for Formula V; and pharmaceutically acceptable salts thereof.

Preferred compounds of Formula Va include those where p is 1 or greater, e.g. compounds that are substituted at the ortho and/or meta phenyl ring positions by R" groups other than hydrogen, or 2,5-phenyl ring substituted, 2,3,5-phenyl ring substituted or 2,4,5-phenyl ring substituted by R" groups other than hydrogen such as halogen, substituted or unsubstituted alkyl having 1 to about 6 carbon atoms, substituted or unsubstituted alkoxy having 1 to about 6 carbon atoms, or substituted or unsubstituted alkylthio. It is of course understood that where a phenyl or napthyl group of Formulae Va or Vaa is not substituted by an R" group, the ring position is hydrogen-substituted. While as shown by the above structure Formula Vaa includes compounds that have either a 1-naphthyl or 2-naphthyl amino substituent, compounds having a 1-naphthyl group are generally more preferred. Compounds of Formula Vaa that have a non-hydrogen R" substituent at the 4-naphthyl position are also particularly preferred.

Compounds of Formula V may suitably contain one or more 5,6-dihydrophenanthridinyl ring substituents, i.e. the sum of the values of m and n of Formula V is one or more.

Generally preferred compounds of Formula V include those compounds that contain 0 (i.e. the 6-hydrophenanthridinyl ring position is —$CH_2$—), or 1 (i.e. the 6-hydrophenanthridinyl ring position is —$CH(R^2)$—) non-hydrogen $R^2$ substituents. Generally preferred compounds also include those that contain 0 (ring positions 5–8 each hydrogen substituted), 1 or 2 $R^3$ and/or $R^4$ ring substiruents.

Preferred compounds of Formula V include those that are unsubstituted on the 5,6-dihydrophenanthridinyl ring (m, n and r each zero), particularly compounds of the following Formula Vb:

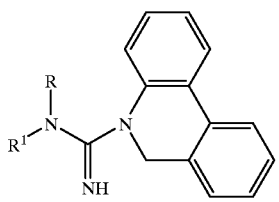

Vb where R and $R^1$ are each the same as defined above for Formula V; and pharmaceutically acceptable salts thereof. The above noted preferred R and $R^1$ groups of Formula V are also preferred R and $R^1$ groups of compounds of Formula Vb.

Suitable halogen substituent groups of compounds of Formulae I, I', I", Ia, Iaa, Ib, II, II", IIa, IIaa, IIb, III, IIIa, IIIaa, IIIb, IV, IVa, IVaa, IVb, V, Va, Vaa, Vb, VI, VII, VIII or IX, as defined above (i.e. compounds of the invention) include F, Cl, Br and I. Alkyl groups of compounds Formulae I, I", II, II", III, IV, V, VI, VII, VIII or IX preferably have from 1 to about 12 carbon atoms, more preferably 1 to about 8 carbon atoms, still more preferably 1 to about 6 carbon atoms, even more preferably 1, 2, 3 or 4 carbon atoms. (It is understood that references herein to Formulae I; I"; II; II"; III; IV; and V apply equally to compounds of Formulae I', Ia, Iaa and Ib; IIa, IIaa and IIb; IIIa, IIIaa and Ib; IVa, IVaa and IVb; Va, Vaa and Vb, respectively, as those formulae are defined herein. Hence, suitable and preferred substituent groups of Formulae I, I", II, II", III, IV and V are also suitable and preferred substituent groups of compounds of Formulae I', Ia, Iaa, Ib, IIa, IIaa, IIb, IIIa, IIIaa, IIIb, IVa, IVaa, IVb, Va, Vaa and Vb unless otherwise indicated.) Methyl, ethyl and propyl including isopropyl are particularly preferred alkyl groups of compounds of the invention. As used herein, the term alkyl unless otherwise modified refers to both cyclic and noncyclic groups, although of course cyclic groups will comprise at least three carbon ring members. Preferred alkenyl and alkynyl groups of compounds of the invention have one or more unsaturated linkages and from 2 to about 12 carbon atoms, more preferably 2 to about 8 carbon atoms, still more preferably 2 to about 6 carbon atoms, even more preferably 1, 2, 3 or 4 carbon atoms. The terms alkenyl and alkynyl as used herein refer to both cyclic and noncyclic groups, although straight or branched noncyclic groups are generally more preferred. Preferred alkoxy groups of compounds of Formulae I, I", II, II", III, IV, V, VI, VII, VIII or IX include groups having one or more oxygen linkages and from 1 to about 12 carbon atoms, more preferably from 1 to about 8 carbon atoms, and still more preferably 1 to about 6 carbon atoms, even more preferably 1, 2, 3 or 4 carbon atoms. Preferred alkyltbio groups of compounds of Formulae I through IX (which includes Formulae I" and II") include those groups having one or more thioether linkages and from 1 to about 12 carbon atoms, more preferably from 1 to about 8 carbon atoms, and still more preferably 1 to about 6 carbon atoms. Alkylthio groups having 1, 2, 3 or 4 carbon atoms are particularly preferred. Preferred alkylsulfinyl groups of compounds of the invention include those groups having one or more sulfoxide (SO) groups and from 1 to about 12 carbon atoms, more preferably from 1 to about 8 carbon atoms, and still more preferably 1 to about 6 carbon atoms. Alkylsulfmyl groups having 1, 2, 3 or 4 carbon atoms are particularly preferred. Preferred alkylsulfonyl groups of compounds of the invention include those groups having one or more sulfonyl ($SO_2$) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred. Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary ammire moieties. Suitable heteroaromatic groups of compounds of Formulae I, I", II, II", III, IV, V, VI, VII, VIII or IX contain one or more N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzothiazol. Suitable heteroalicyclic groups of compounds of Formulae I, I", II, II", III, IV, V, VI, VII, VIII or IX contain one or more N, O or S atoms and include, e.g., tetrahydrofurnyl, tetrahydropyranyl, piperidinyl, morpholino and pyrrolindinyl groups. Suitable carbocyclic aryl groups of compounds of Formulae I, I", II, II", III, IV, V, VI, VII, VIII or IX include single and multiple ring compounds, including multiple ring compounds that contain separate and/or fused aryl groups. Typical carbocyclic aryl groups contain 1 to 3 separate or fused rings and from 6 to about 18 carbon ring atoms. Specifically preferred carbocyclic aryl groups include phenyl including substituted phenyl, such as 2-substituted phenyl, 3-substituted phenyl, 2,3-substituted phenyl, 2,5-substituted phenyl, 2,3,5-substituted and 2,4,5-substituted phenyl, including where the phenyl substituents are selected from the same group as defined above in Formulae I–V for $R^3$; naphthyl including 1-naphthyl and 2-naphthyl; biphenyl; phenanthryl; and anthracyl. Suitable aralkyl groups of compounds of Formulae I, I", II, II", III, IV, V, VI, VII, VIII or IX include single and multiple ring compounds, including multiple ring compounds that contain separate and/or fused aryl groups. Typical aralkyl groups contain 1 to 3 separate or fused rings and from 6 to about 18 carbon ring atoms. Preferred aralkyl groups include benzyl and methylenenaphthyl (—$CH_2$-naphthyl).

References herein to substituted R, $R^1$, $R^2$, $R^3$, $R^4$, R" and X groups of compounds of the invention refer to the specified moiety that may be substituted at one or more available positions by one or more suitable groups such as, e.g., halogen such as fluoro, chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms or from 1 to about 6 carbon atoms and more preferably 1–3 carbon atoms; alkenyl and alkynyl groups including groups having one or more unsaturated linkages and from 2 to about 12 carbon or from 2 to about 6 carbon atoms; alkoxy groups having those having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfihyl groups including those moieties having one or more sulfmyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl (e.g. R being a substituted or unsubstituted biphenyl moiety); and aralkyl such as benzyl. Generally preferred substituents of substituted nitrogen and methylene X groups of compounds of Formulae I, II and VI include the groups from which $R^2$ is selected in Formulae I, II and VI. More typical substituents of substituted nitrogen and methylene X groups of compounds of Formulae I, II and VI include substituted and unsubstituted alkyl, including $C_{1-4}$ alkyl and halo-substituted $C_{1-4}$ alky, particularly fluoro-substituted $C_{1-4}$ alkyl such as trifluoromethyl, and in the case of a substituted methylene group, halogen and alkylthio.

It should be understood that alkoxy, alkylthio, alkylsulfinyl, alkylsulfonyl and arinoalkyl substituent groups described above include groups where a hetero atom is directly bonded to a ring system, such as a carbocyclic aryl group or a heterocyclic group, as well as groups where a hetero atom of the group is spaced from such ring system by an alkylene linkage, e.g. of 1 to about 4 carbon atoms.

Preferred carbocyclic ring substituents of compounds of Formulae I, I", II, II", III, IV, V, VI, VII, VIII or IX (including substituents of the group R where R is a carbocyclic ring such as phenyl or naphthyl, i.e. compounds of Formula Ia, Iaa, IIa, IIaa, IIIa, IIIaa, IVa, IVaa, Va and Vaa where p or $s \geq 1$ and R" is other than hydrogen) include halogen, particularly F, Cl and Br; hydroxyl; azido; substituted or unsubstituted alkyl having 1 to about 6 carbons such as methyl, ethyl, propyl and butyl, and including halogenated alkyl, particularly fluoro-alkyl having 1 to about 6 carbon atoms; substituted and unsubstituted alkoxy having 1 to about 6 carbons and including halogenated alkoxy, particularly fluoro-alkoxy having 1 to about 6 carbon atoms; substituted and unsubstituted alkylthio having 1 to about 6 carbons; substituted and unsubstituted alkylsulfinyl having 1 to about 6 carbons; substituted and unsubstituted alkylsulfonyl having 1 to about 6 carbons; and carbocyclic aryl, particularly phenyl to provide a substituted phenyl R group that is bi-phenyl. Typically preferred phenyl ring substituents have 1 to 4 carbon atoms with methyl, ethyl, propyl including isopropyl and butyl including sec-butyl being particularly preferred. Halogen-substituted alkyl and alkoxy groups are also particularly preferred including fluoroalkyl having 1, 2, 3 or 4 carbon atoms such as trifluoromethyl and fluoro-substituted alkoxy having 1, 2, 3 or 4 carbon atoms such as trifluoromethoxy (—$OCF_3$). Methylthio (—$SCH_3$) and ethylthio (—$SCH_2CH_3$) are also particularly preferred phenyl ring substituents. Preferred alkylsulfinyl ring substituents of carbocyclic aryl groups of compounds of the invention typically have one or more sulfoxide groups, more typically, one or two sulfoxide groups and from 1 to about 8 carbon atoms, more preferably 1 to about 6 carbon atoms, even more preferably 1 to about 3 carbon atoms. Methylsulfinyl (—$S(O)CH_3$) and ethylsulfinyl (—$S(O)CH_2CH_3$) are particularly preferred $R^2$, $R^3$ and $R^4$ alkylsulfinyl ring substituents as well as preferred ring substituents of a substituted carbocyclic R group. In particular, methylsulfinylphenyl and ethylsulfinylphenyl are preferred R groups. Preferred substituted alkylsulfinyl substituents include haloalkylsulfinyl groups that contain one or more F, Cl, Br or I atoms, preferably one or more F atoms, and preferably 1 to about 3 carbon atoms, more preferably one or two carbon atoms. Specifically preferred groups include fluoromethylsulfinyl, particularly trifluoromethylsulfinyl (—$S(O)CF_3$), and fluoroethylsulfinyl such as 2-trifluoroethylsulfinyl (—$S(O)CH_2CF_3$) and pentafluoroethylsulfinyl (—$S(O)CF_2CF_3$). Preferred alkylsulfonyl ring substituents of carbocyclic aryl group compounds of the invention have one or more sulfono ($SO_2$) groups, more typically one sulfono group, and from 1 to about 8 carbon atoms, still more preferably 1 to about 6 carbon atoms, even more preferably 1 to about 3 carbon atoms. Methylsulfonyl (—$S(O)_2CH_3$) and ethylsulfonyl (—$S(O)_2CH_2CH_3$) are particularly preferred sulfonoalkyl ring substituents. Preferred substituted allylsulfonyl substituents include haloalkylsulfonyl groups that contain one or more F, Cl, Br or I atoms, preferably one or more F atoms, and preferably 1 to about 3 carbon atoms, more preferably one or two carbon atoms. Specifically preferred groups include fluoromethylsulfonyl, particularly trifluoromethylsulfonyl (—$S(O)_2CF_3$), and fluoroethylsulfonyl such as 2-trifluoroethylsulfonyl (—$S(O)_2CH_2CF_3$) and pentafluoroethylsulfonyl (—$S(O)_2CF_2CF_3$).

Without wishing to be bound by theory, compounds of the invention that contain an alkylsulfinyl and/or alkylsulfonyl group, may be, in effect, "pro-drugs" wherein after administration of the compound to a subject the sulfinyl or sulfonyl group(s) are metabolized (reduced) in vivo to the corresponding sulfide moiety.

Specifically preferred compounds of Formula I include the following:

N-(4-benzyloxyphenyl)-1-indolinylcarboxiridamide;
N-(4-methoxynaphthyl)-1-indolinylcarboximidarnide;
N-(1-naphthyl)-1-indolinylcarboximidarnide;
N-(3,4-dimethoxynaphthyl)-1-indolinylcarboximidamide;
N-(3,4dichlorophenyl)-1-indolinylcarboximidamide;
N-(1-naphthyl)-1-(7-ethyl)-indolinylcarboximidamide;
N-(2-naphthyl)-1-(7-ethyl)-indolinylcarboximidamide;
N-(4-sec-butylphenyl)-1-indolinylcarboximidamide;
N-(2,3-dichlorophenyl)-1-indolinylcarboximidamide;
N-(2,3-dirnethylphenyl)-1-indolinylcarboximidamide;
N-(5,6,7,8-tetrahydro-1-naphthyl)-1-indolinylcarboximidamide;
N-(2-biphenyl)-1-indolinylcarboximidamide;
N-(1-naphthyl)-N-methyl-1-indolinylcarboximidamide;
N-(2-naphthyl)-1-indolinylcarboximidamide;
N-phenyl-1-indolinylcarboximidarnide;
N-(2-chlorophenyl)-1-indolinylcarboximidamide;
N-(2-methylphenyl)-1-indolinylcarboxinidamide;
N-(3-methylphenyl)-1-indolinylcarboximidamide;
N-(2,5-dimethylphenyl)-1-indolinylcarboximidamide;
N-(2,5-dibromophenyl)-1-indolinylcarboximidamide;
N-(2,5-dichlorophenyl)-1-indolinylcarboximidamide;
N-(5-acenaphthyl)-1-(5-methoxy)-indolinylcarboximidamide;
N-(5-acenaphthyl)-1-(5-bromo)-indolinylcarboximidamide;
N-(2,3-dimethoxyphenyl)-1-indolinylcarboximidarnide;

and pharmaceutically acceptable salts of said compounds.

N-(1-naphthyl)-1-indolinylcarboximidamide and pharmaceutically acceptable salts thereof are particularly preferred compounds of Formula I.

Additional preferred compounds of Formula I include the following where the compound is structurally depicted above the chemical name thereof, and pharmaceutically acceptable salts of these depicted compounds.

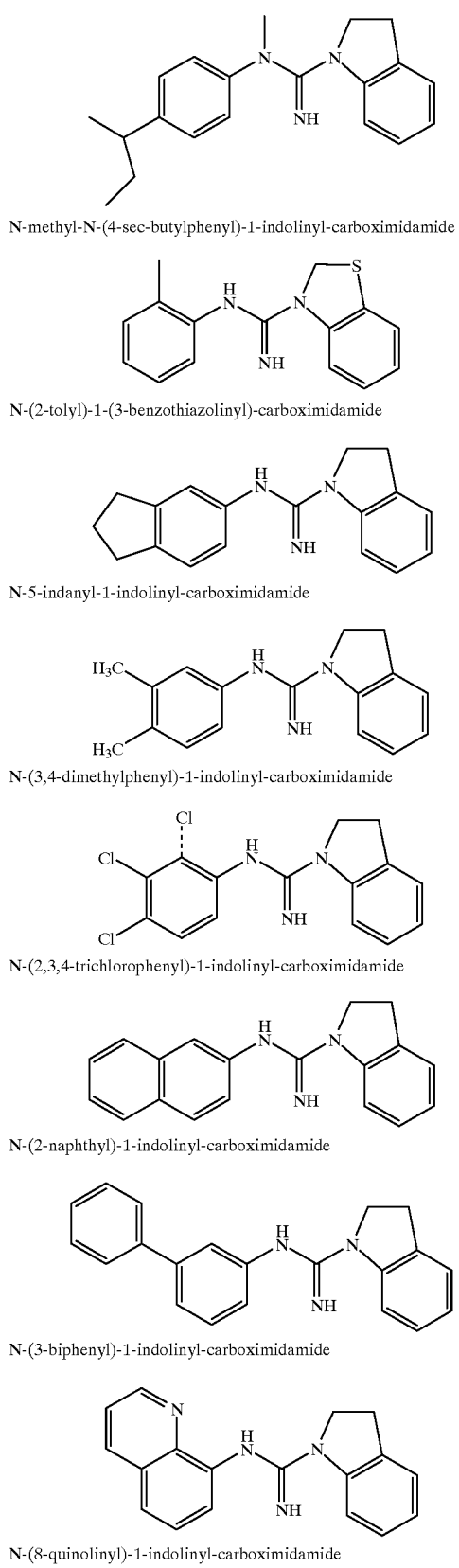
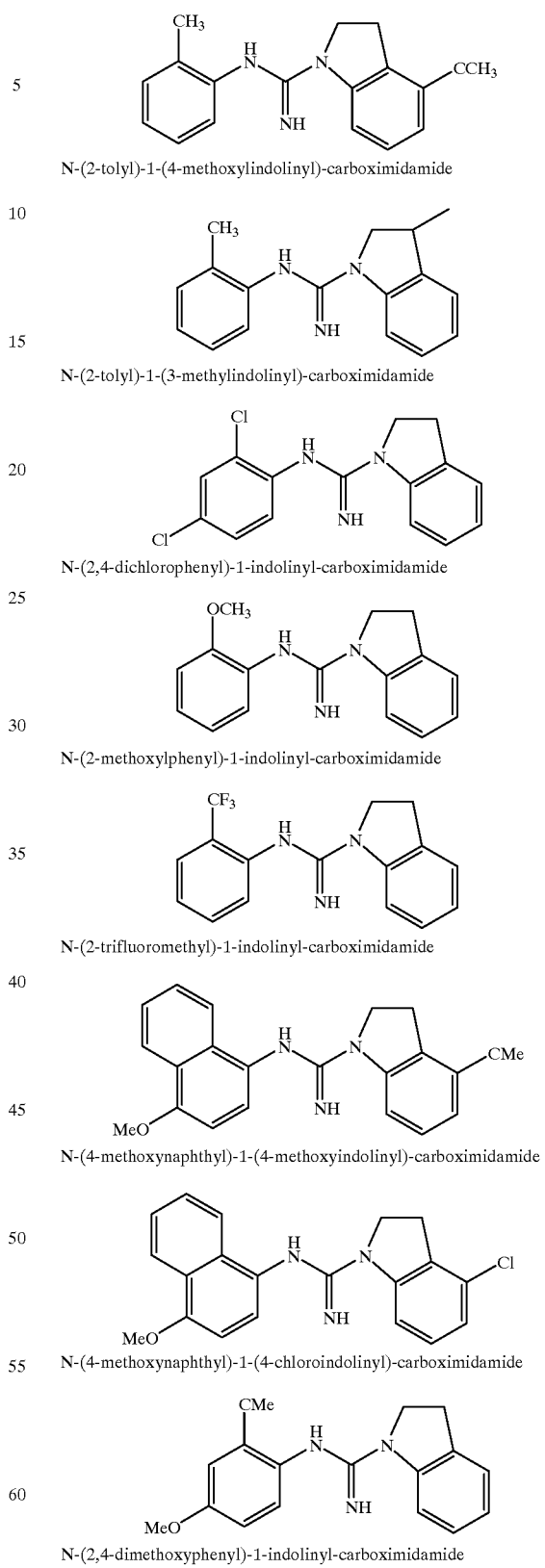

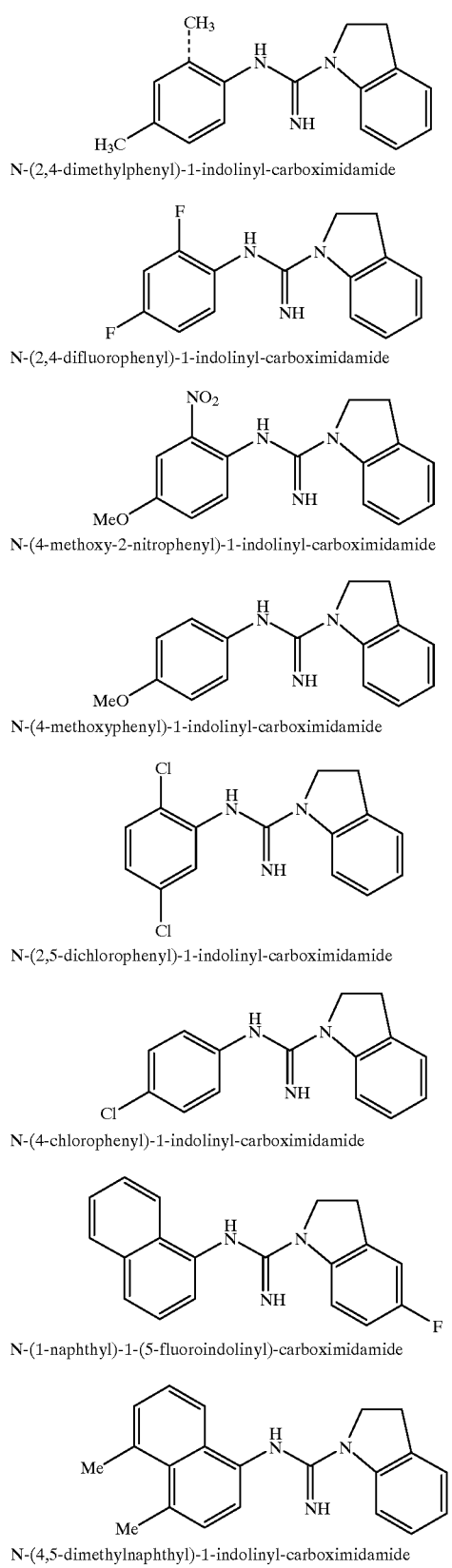

N-(2,4-dimethylphenyl)-1-indolinyl-carboximidamide

N-(2,4-difluorophenyl)-1-indolinyl-carboximidamide

N-(4-methoxy-2-nitrophenyl)-1-indolinyl-carboximidamide

N-(4-methoxyphenyl)-1-indolinyl-carboximidamide

N-(2,5-dichlorophenyl)-1-indolinyl-carboximidamide

N-(4-chlorophenyl)-1-indolinyl-carboximidamide

N-(1-naphthyl)-1-(5-fluoroindolinyl)-carboximidamide

N-(4,5-dimethylnaphthyl)-1-indolinyl-carboximidamide

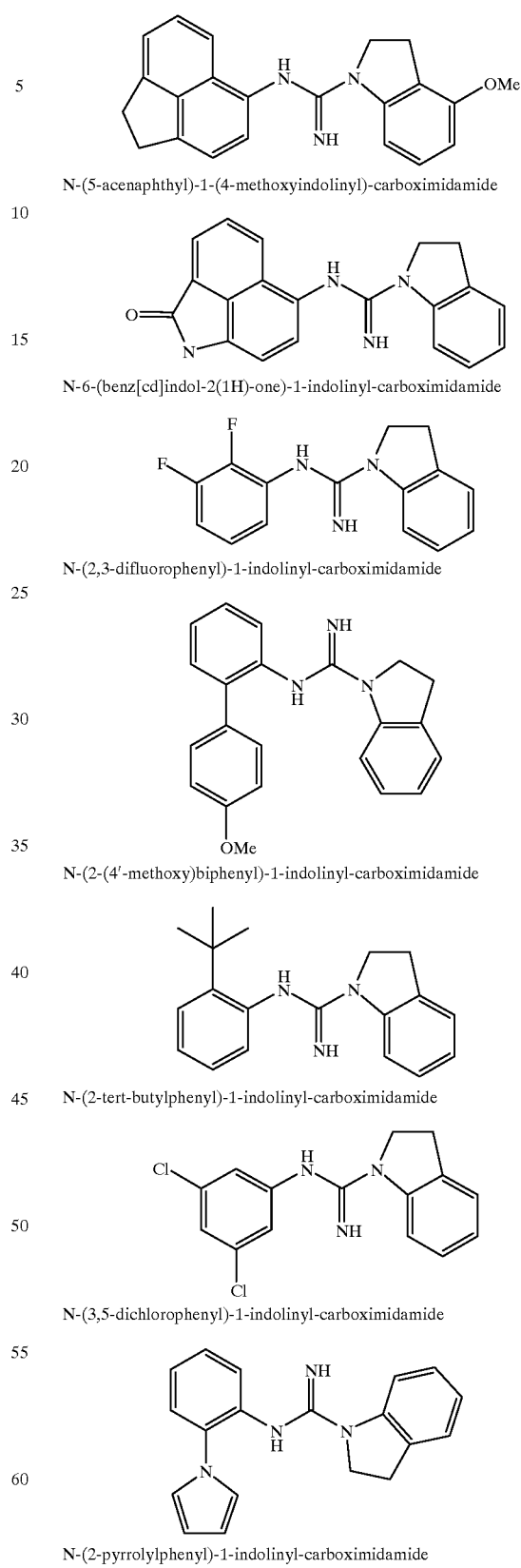

N-(5-acenaphthyl)-1-(4-methoxyindolinyl)-carboximidamide

N-6-(benz[cd]indol-2(1H)-one)-1-indolinyl-carboximidamide

N-(2,3-difluorophenyl)-1-indolinyl-carboximidamide

N-(2-(4'-methoxy)biphenyl)-1-indolinyl-carboximidamide

N-(2-tert-butylphenyl)-1-indolinyl-carboximidamide

N-(3,5-dichlorophenyl)-1-indolinyl-carboximidamide

N-(2-pyrrolylphenyl)-1-indolinyl-carboximidamide

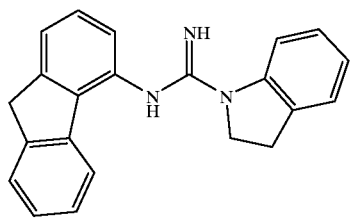

N-(4-fluorenyl)-1-indolinyl-carboximidamide

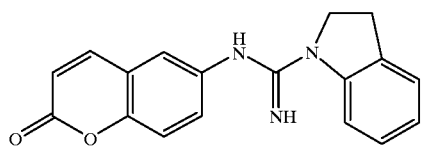

N-(6-coumarinyl)-1-indolinyl-carboximidamide

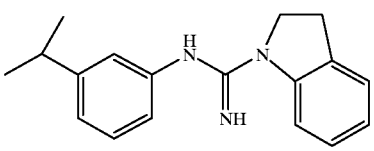

N-(3-isopropylphenyl)-1-indolinyl-carboximidamide

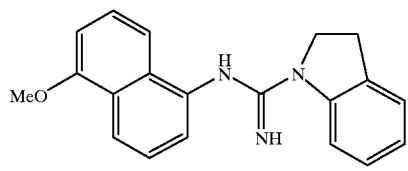

N-(5-methoxynaphthyl)-1-indolinyl-carboximidamide

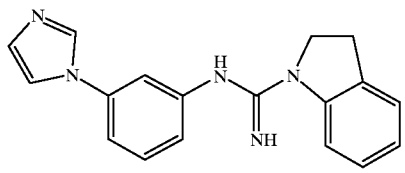

N-(3-(1H-imidazol-1-yl)-1-indolinyl-carboximidamide

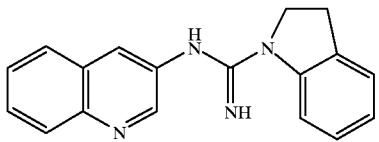

N-(3-quinolinyl)-1-indolinyl-carboximidamide

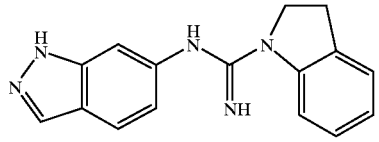

N-(6-indazole)-1-indolinyl-carboximidamide

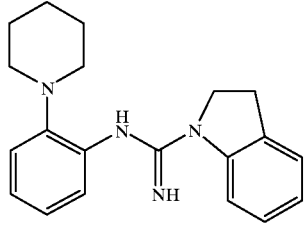

N-(2-piperidinylphenyl)-1-indolinyl-carboximidamide

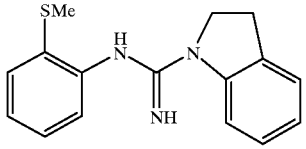

N-(2-methylmercapto)phenyl-1-indolinyl-carboximidamide

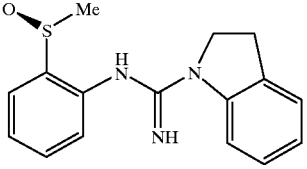

N-(1-methylsulfoxyphenyl)-1-indolinyl-carboximidamide

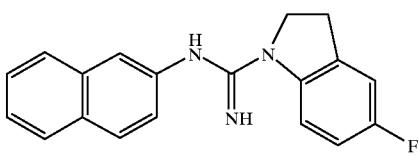

N-(2-naphthyl)-1-(5-fluoroindolinyl)-carboximidamide

Specifically preferred compounds of Formula II include the following:
N-(1-naphthyl)-1-(1,2,3,4-tetrahydroquinolinyl) carboximidamide;
N-(1-naphthyl)-1-(7-trifluoromethyl)-(1,2,3,4-tetrahydroquinolinyl) carboxinriidamide;
N-(1-naphthyl)-1-(7-methyl)-(1,2,3,4-tetrahydroquinolinyl) carboximidamide;
N-(2,5-dibromophenyl)-1-(7-trifluorometihyl)-(1,2,3,4-tetrahydroquinolinyl) carboximidamide;
N-(1-naphthyl)-1-(2-trifluoromethyl)-(1,2,3,4-tetrahydroquinolinyl) carboxirnidamide;
N-(4-benzyloxyphenyl)-1-(1,2,3,4-tetrahydroquinolinyl) carboximidamide;
N-(4-methoxynaphthyl)-1-(1,2,3,4-tetrahydroquinolinyl) carboximidamide;
N-(3,4-dichlorophenyl)-1-(1,2,3,4-terrahydroquinolinyl) carboxirnidamide;
N-(5-acdnaphthyl)-1-(5-methoxy)-(1,2,3,4-tetrahydroquinolinyl) carboxinidaraide;
N-(5-acenaphthyl)-1-(5-bmromto)-(1,2,3,4-tetrahydroquinolinyl) carboximidamide;
N-(5-naphthyl)-1-(7-ethyl)-(1,2,3,4-tetrahydroquinolinyl) carboximidamide;
N-(4-sec-burylphenyl)-1-(1,2,3,4-tetrahydroquinolinyl) carboximidamide;
N-(2,3-dichlorophenyl)-1-(1,2,3,4-terrahydroquinolinyl) carboximidamide;
N-(2 3-dimethylphenyl)-1-(1,2,3,4-tetrahydroquinolinyl) carboximidamide;
N-(5,6,7,8-tetrahydro-1-naphthyl)-1-(1,2,3,4-tetrahydroquinolinyl) carboximidamide;
N-(2-biphenyl)-1-(1,2,3,4-retrahydroquinolinyl) carboximidamide;
N-(3-biphenyl)-1-(1,2,3,4-tetrahydroquinolinyl) carboximnidamide;
N-(1-naphthyl)-1-(1,2,3,4-tetrahydroquinolinyl) carboximidamide;
N-(2-ethylphenyl)-1-(1,2,3,4-tetrthydroquinotinyl) carboximidamide;
N-(3-ethylphenyl)-1-(1,2,3,4-rerahydroquinolinyl) carboximidarnide;
N-(2,5-dimethylphenyl)-1-(1,2,3,4-cetrahydroquinolinyl) carboximidamide;

N-(2-chloro-5-ethylphenyl)-1-(7-trifluoromethyl)-(1,2,3,4-tetrahydroquinolinyl) carboximidamide;
N-(2,5-dibromophenyl)-1-(1,2,3,4-tetrahydroquinolinyl) carboximidamide;
N-(2,5-dichlorophenyl)-1-(1,2,3,4-tetrahydroquinolinyl) carboximidamide;
N-(3-methylthiophenyl)-1-(1,2,3,4-tetrahydroquinolinyl) carboximidamide;
N-(2,3-dichlorophenyl)-1-(1,2,3,4-tetrahydroquinolinyl) carboximidamide;
N-(2,3-difluorophenyl)-1-(1,2,3,4-tetrahydroquinolinyl) carboximidamide;

and pharmaceutically acceptable salts of said compounds.

N-(2,5-dibromophenyl)-1-(7-trifluoromethyl)-(1,2,3,4-tetrahydroquinolinyl) carboximidamide and pharmaceutically acceptable salts thereof are particularly preferred compounds of Formula II, i.e. the compound of the following structure and pharmaceutically acceptable salts thereof:

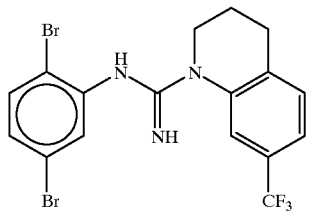

Additional preferred compounds of Formulae II and II' include the following where the compound is structurally depicted above the chemical name thereof, and pharmaceutically acceptable salts of these depicted compounds.

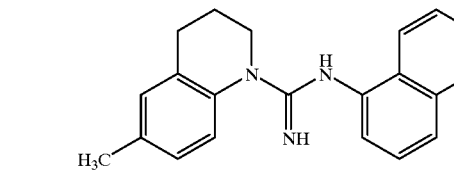

N-(1-naphthyl)-1-(6-methyl-1,2,3,4,-tetrahydroquinoline) carboximidamide

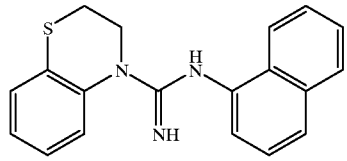

N-(1-naphthyl)-4-(2,3-dihydro[1,4]benzothiazinyl)carboximidamide

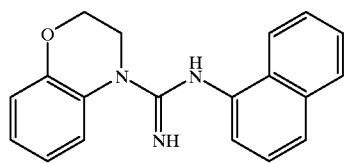

N-(1-naphthyl)-4-(2,3-dihydro[1,4]benzoxazinyl)carboximidamide

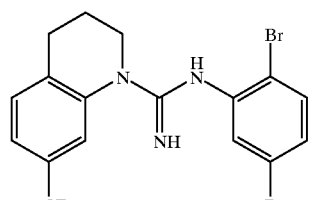

N-(2,5-dibromophenyl)-1-[7-[trifluoromethyl]-1,2,3,4-tetrahydroquinoline]carboximidamide

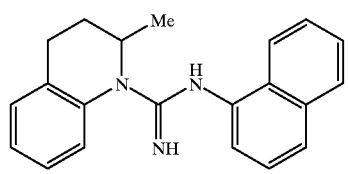

N-(1-naphthyl)-1-(2-methyl-1,2,3,4-tetrahydroquinolin-1-yl) carboximidamide

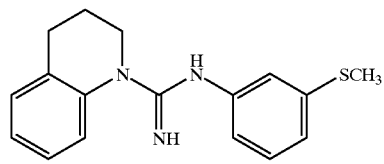

N-(3-methylthiophenyl)-1-(1,2,3,4-tetrahydroquinolinyl) carboximidamide

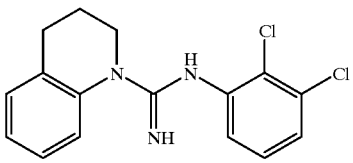

N-(2,3-dichlorophenyl)-1-(1,2,3,4-tetrahydroquinolinyl) carboximidamide

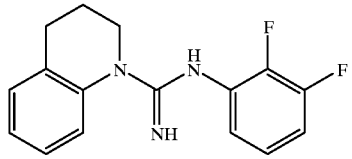

N-(2,3-difluorophenyl)-1-(1,2,3,4-tetrahydroquinolinyl) carboximidamide

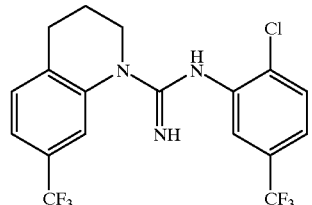

N-[2-chloro-5-(trifluoromethyl)phenyl]-1-(7-(trifluoromethyl)-1,2,3,4-tetrahydroquinolinyl)carboximidamide

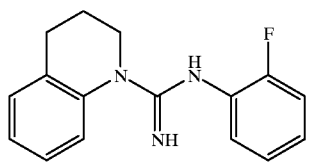

N-(2-fluorophenyl)-1-(1,2,3,4-tetrahydroquinolinyl)carboximidamide

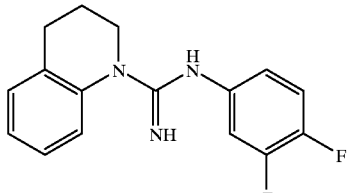

N-(3,4-difluorophenyl)-1-(1,2,3,4-tetrahydroquinolinyl)
carboximidamide

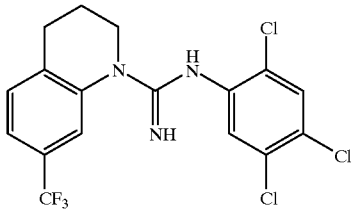

N-(2,4,5-trichlorophenyl)-1-(7-(trifluoromethyl)-1,2,3,4-
tetrahydroquinolinyl)carboximidamide

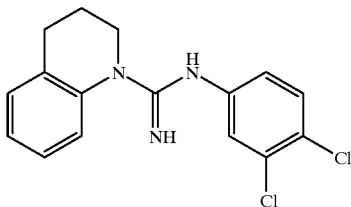

N-(3,4-dichlorophenyl)-1-(1,2,3,4-tetrahydroquinolinyl)
carboximidamide

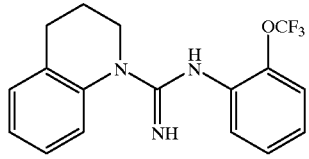

N-(2-trifluoromethoxyphenyl)-1-(1,2,3,4-tetrahydroquinolinyl)
carboximidamide

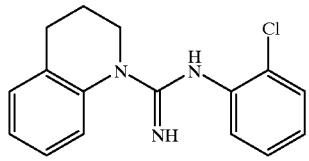

N-(2-chlorophenyl)-1-(1,2,3,4-tetrahydroquinolinyl)carboximidamide

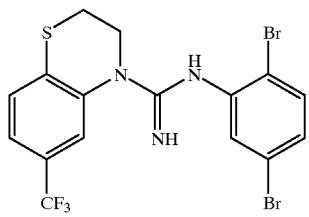

N-(2,5-dibromophenyl)-4-(2,3-dihydro-6-trifluoromethyl-[1,4]-
benzothiazinyl)carboximidamide

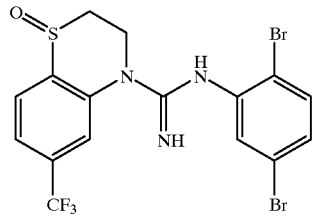

N-(2,5-dibromophenyl)-4-(2,3-dihydro-4-oxo-6-trifluoromethyl-[1,4]-
benzothiazinyl)-carboximidamide

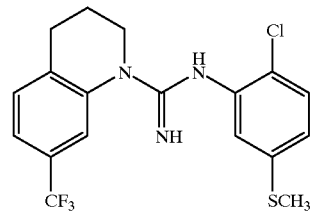

N-(2-chloro-5-thiomethylphenyl)-1-(7-trifluoromethyl-1,2,3,4-
tetrahydroquinolinyl)carboximidamide

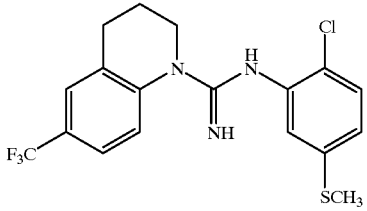

N-(2-chloro-5-methylthiophenyl)-1-(6-trifluoromethyl-1,2,3,4-
tetrahydroquinolinyl)carboximidamide

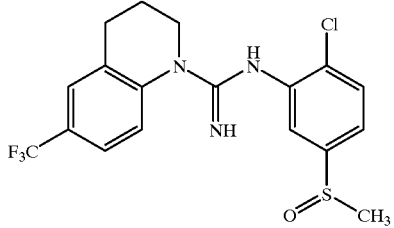

N-(2-chloro-5-sulfinylmethylphenyl)-1-(6-trifluoromethyl-1,2,3,4-
tetrahydroquinolinyl)carboximidamide

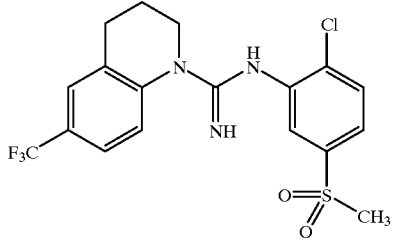

N-(2-chloro-5-sulfonylmethylphenyl)-1-(6-trifluoromethyl-1,2,3,4-
tetrahydroquinolinyl)carboximidamide

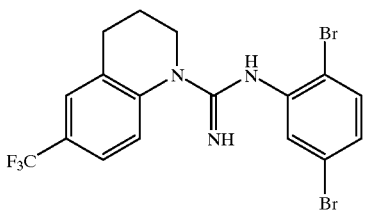

N-(2,5-dibromophenyl)-1-[6-(trifluoromethyl)-1,2,3,4-
tetrahydroquinolinyl]carboximidamide -continued

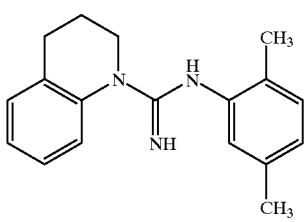

N-(2,5-dimethylphenyl)-1-(1,2,3,4-tetrahydroquinolinyl)carboximidamide

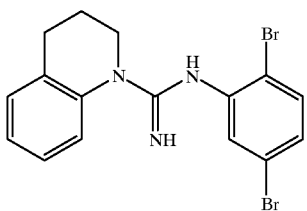

N-(2,5-dibromophenyl)-1-(1,2,3,4-tetrahydroquinolinyl)carboximidamide

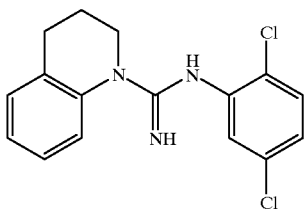

N-(2,5-dichlorophenyl)-1-(1,2,3,4-tetrahydroquinolinyl)carboximidamide

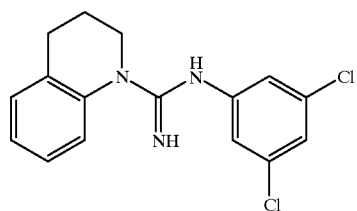

N-(3,5-dichlorophenyl)-1-(1,2,3,4-tetrahydroquinolinyl)carboximidamide

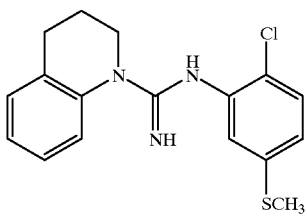

N-(2-chloro-5-thiomethylphenyl)-1-(1,2,3,4-tetrahydroquinoline)carboximidamide

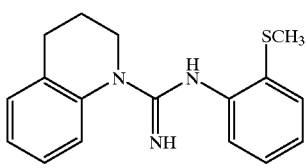

N-(2-methylthiophenyl)-1-(1,2,3,4-tetrahydroquinolinyl)carboximidamide

-continued

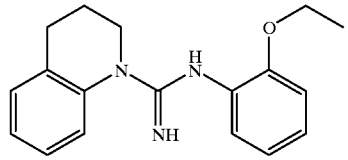

N-(2-ethoxyphenyl)-1-(1,2,3,4-tetrahydroquinolinyl)carboximidamide

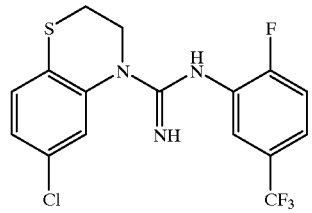

N-(2-fluoro-5-trifluoromethylphenyl)-4-(6-chloro-[1,4]-benzothiazinyl)carboximidamide

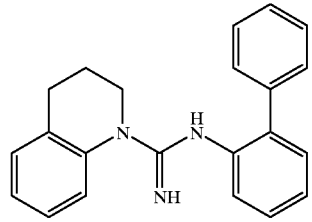

N-(2-biphenyl)-1-(1,2,3,4-tetrahydroquinolinyl)carboximidamide

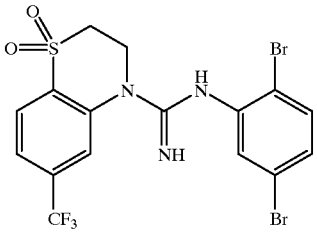

N-(2,5-dibromophenyl)-4-(2,3-dihydro-1-dioxo-6-trifluoromethyl)-([1,4]-bezothiazinyl)carboximidamide

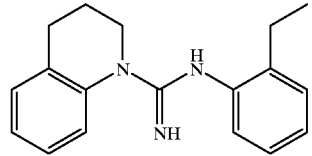

N-(2-ethylphenyl)-1-(1,2,3,4-tetrahydroquinolinyl)carboximidamide

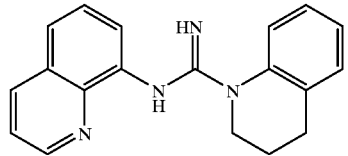

N-(8-quinolinyl)-1-(1,2,3,4-tetrahydroquinolinyl)carboximidamide

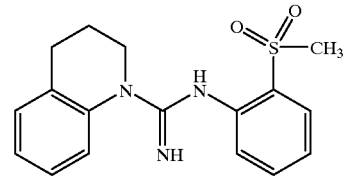

N-(2-methylsulfonylphenyl)-1-(1,2,3,4-tetrahydroquinolinyl)carboximidamide

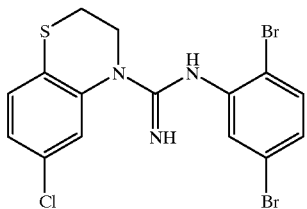

N-(2,5-dibromophenyl)-4-(6-chloro-[1,4]-benzothiazinyl)
carboximidamide

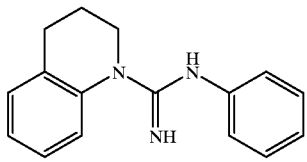

N-phenyl-1-(1,2,3,4-tetrahydroquinolinyl)carboximidamide

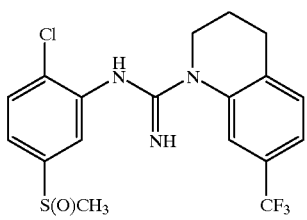

N-(2-chloro-5-methylthiophenyl)-1-(7-trifluoromethyl-1,2,3,4-
tetrahydroquinolinyl)-carboximidamide

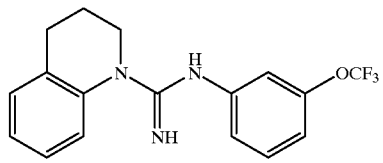

N-(3-trifluoromethoxyphenyl)-1-(1,2,3,4-tetrahydroquinolinyl)-
carboximidamide

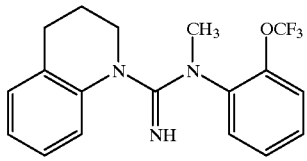

N-(2-trifluoromethoxyphenyl)-N-methyl-1-(1,2,3,4-
tetrahydroquinolinyl)carboximidamide

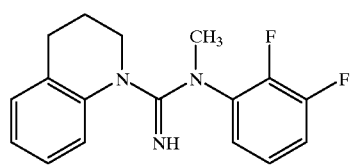

N-(2,3-difluorophenyl)-N-methyl-1-(1,2,3,4-tetrahydroquinolinyl)
carboximidamide

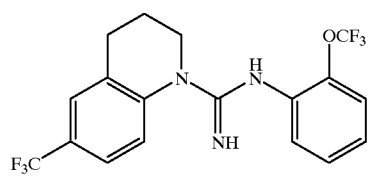

N-(2-trifluoromethoxyphenyl)-1-(6-trifluoromethyl-1,2,3,4-
tetrahydroquinolinyl)-carboximidamide

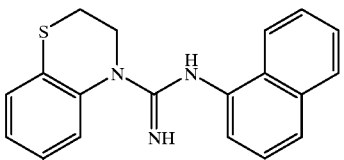

N-(1-naphthyl)-4-(6-chloro-2,3-dihydro-[1,4]-benzothiazinyl)
carboximidamide

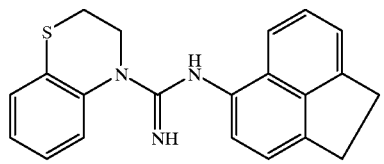

N-(5-acenaphthyl)-4-(2,3-dihydro-[1,4]-benzothiazinyl)
carboximidamide

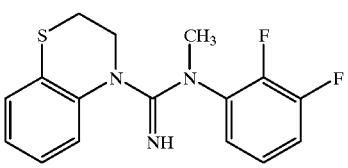

N-(2,3-difluorophenyl)-N-methyl-4-(2,3-dihydro-[1,4]-benzothiazinyl)
carboximidamide

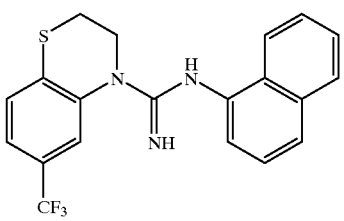

N-(1-naphthyl)-4-(6-trifluoromethyl-2,3-dihydro-[1,4]-benzothiazinyl)
carboximidamide

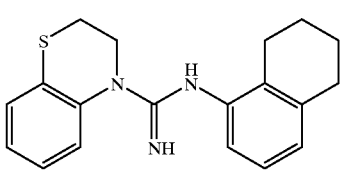

N-(5,6,7,8-tetrahydro-1-naphthyl)-4-(2,3-dihydro-[1,4]-benzothiazinyl)
carboximidamide

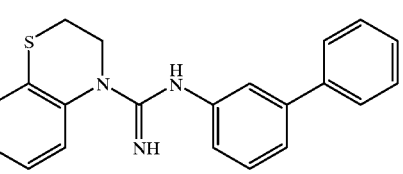

N-(3-biphenyl)-4-(2,3-dihydro-[1,4]-benzothiazinyl)carboximidamide

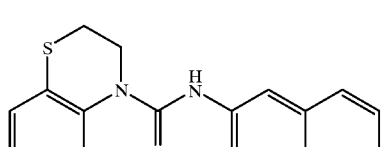

N-(2-naphthyl)-4-(2,3-dihydro-[1,4]-benzothiazinyl)carboximidamide

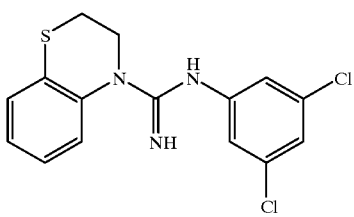

N-(3,5-dichlorophenyl)-4-(2,3-dihydro-[1,4]-benzothiazinyl) carboximidamide

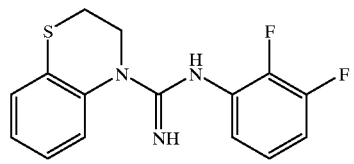

N-(2,3-difluorophenyl)-4-(2,3-dihydro-[1,4]-benzothiazinyl) carboximidamide

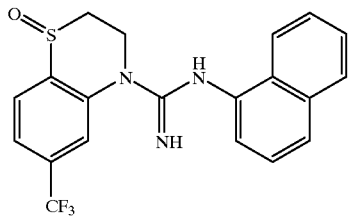

N-(1-naphthyl)-4-(2,3-dihydro-6-trifluoromethylbenzo[1,4]-1-oxo-thiazinyl)carboximidamide Specifically preferred compounds of Formula III include dhe following:

N-(1-naphthyl)-1-(1,2,3,4-tetrahydroisoquinolinyl) carboximidamide;
N-(1-naphthyl)-1-(7-trifluoromethyl)-(1,2,3,4-tetrahydroisoquinolinyl) carboximidamide;
N-(1-naphthyl)-1-(7-methyl)-(1,2,3,4-tetrahydroisoquinolinyl) carboximidamide;
N-(2,5-dibromophenyl)-1-(7-trifluoromethyl)-(1,2,3,4-tetrahydroisoquinolinyl) carboximidamide;
N-(1-naphthyl)-1-(2-trifluoromethyl)-(1,2,3,4tetrahydroisoquinolinyl) carboximidamide;
N-(4-benzyloxyphenyl)-1-(1,2,3,4-tetrahydroisoquinolinyl) carboximidamide;
N-(4-methoxynaphthyl)-1-(1,2,3,4-terrahydroisoquinolinyl) carboximidamide;
N-(3,4-dichlorophenyl)-1-(1,2,3,4-tetrahydroisoquinolinyl) carboximidamide;
N-(5-acenaphthyl)-1-(5-methoxy)-(1,2,3,4-tetrahydroisoquinolinyl) carboximidamide;
N-(5-acenaphthyl)-1-(5-bromo)-(1,2,3,4-tetrahydroisoquinolinyl) carboximidamide;
N-(1-naphthyl)-1-(7-ethyl)-(1,2,3,4-terrahydroisoquinolinyl) carboximidamide;
N-(4-sec-butylphenyl)-1-(1,2,3,4-tetrahydroisoquinolinyl) carboximldamide;
N-(2,3-dichlorophenyl)-1-(1,2,3,4-tetrahydroisoquinolinyl) carboximidamide;
N-(2,3-dimethylphenyl)-1-(1,2,3,4-tetrahydroisoquinolinyl) carboximidamide;
N-(5,6,7,8-tetrahydro-1-naphthyl)-1-(1,2,3,4-tetrahydroisoquinolinyl) carboximidamide;
N-(2-biphenyl)-1-(1,2,3,4-tetrahydroisoquinolinyl) carboximidamide;
N-(3-biphenyl)-1-(1,2,3,4-tetrahydroisoquinolinyl) carboximidamide;
N-(1-naphthyl)-1-(1,2,3,4-tetrahydroisoquinolinyl) carboximidamide;
N-(2-ethylphenyl)-1-(1,2,3,4-tetrahydroisoquinolinyl) carboxirnidamide;
N-(3-ethylphenyl)-1-(1,2,3,4-tetrahydroisoquinolinyl) carboximidamide;
N-(2,5-dimethylphenyl)-1-(1,2,3,4-tetrahydroisoquinolinyl) carboximidamide;
N-(2-chloro-5-ethylphenyl)-1-(7-trifluoromethyl)-(1,2,3,4-tetrahydroisoquinolinyl) carboximidamide;
N-(2,5-dibromophenyl)-1-(1,2,3,4-tetrahydroisoquinolinyl) carboximidamide;
N-(2,5-dichlorophenyl)-1-(1,2,3,4-tetrahydroisoquinolinyl) carboximidamide;
N-(3-methylthiophenyl)-1-(1,2,3,4-tetrahydroisoquinolinyl) carboximidamide;
N-(2,3-dichlorophenyl)-1-(1,2,3,4-tetrahydroisoquinolinyl) carboximidamide;
N-(2,3-difluorophenyl)-1-(1,2,3,4-tetrahydroisoquinolinyl) carboximidamide;

and pharmaceutically acceptable salts of said compounds.

Specifically preferred compounds of Formula IV include the following:

N-(3-biphenyl)-1-(benz[cd]indolinyl)carboximidamide;
N-(1-naphthyl)-1-(benz[cd]indolinyl)carboximidamide;
N-(2-methylphenyl)-1-(benz[cd]indolinyl) carboximidamide;
N-(2,3-dimethylphenyl)-1-(benz[cd]indolinyl) carboximidamide;
N-(2,5-dimethylphenyl)-1-(benz[cd]indolinyl) carboximidamide;
N-(4-benzyloxyphenyl)-1-(benz[cd]indolinyl) carboximnidamide;
N-(4-methoxynaphthyl)-1-(benz[cd]indolinyl) carboximidamide;
N-(3,4-dichlorophenyl)-1-(benz[cd]indolinyl) carboximidamide;
N-(5-acenaphthyl)-1-(5-methoxy)-1-(benz[cd]indolinyl) carboximidamide;
N-(5-acenaphthyl)-1-(5-bromo)-(benz[cd]indolinyl) carboximidamide;
N-(1-naphthyl)-1-(7-ethyl)-(benz[cd]indolinyl) carboximidamnide;
N-(4-sec-butylphenyl)-1-(benz[cd]indolinyl) carboximidamide;
N-(2,3-dichlorophenyl)-1-(benz[cd]indolinyl) carboximidarnide;
N-(3-methylphenvl)-1-(benz[cd]indolinyl) carboximidamide;
N-(5,6,7,8-cetrahydro-1-naphthyl)-1-(benz[cd]indolinyl) carboximidarnide;
N-(2-biphenyl)-1-(benz[cd]indolinyl)carbo.imidamide;
N-(1-naphthyl)-1-(7-trifluoromethyl)-(benz[cd]indoiinyl) carboximidamide;
N-(3-ethylphenyl)-1-(benz [cd]indolinyl)carboximidamide;
N-(2,5-dibromophenyl)-1-Cbenz[cd]indolinyl) carboximidaraide;
N-(2,5-dichlorophenyl)-1-(benz[cd]indolinyl) carboximidamide;

and pharmaceutically acceptable salts of said compounds.

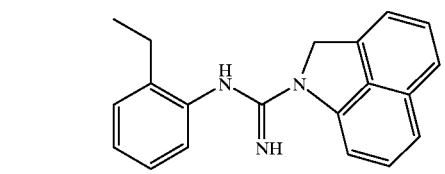

N-(2-ethylphenyl)-(1-benz[cd]indolinyl)carboximidamide

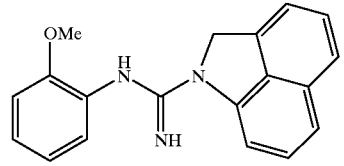

N-(2-methoxyphenyl)-(1-benz[cd]indolinyl)carboximidamide

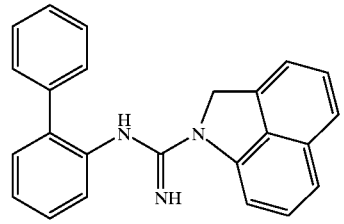

N-(2-biphenyl)-(1-benz[cd]indolinyl)carboximidamide

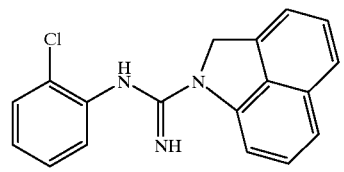

N-(2-chlorophenyl)-(1-benz[cd]indolinyl)carboximidamide

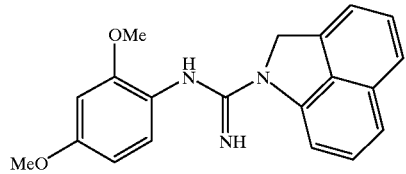

N-(2,4-dimethoxyphenyl)-(1-benz[cd]indolinyl)carboximidamide

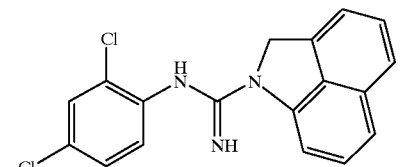

N-(2,4-dichlorophenyl)-(1-benz[cd]indolinyl)carboximidamide

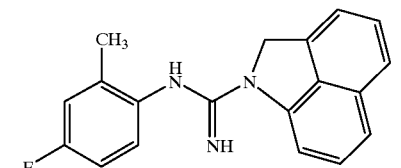

N-(4-fluoro-2-methylphenyl)-(1-benz[cd]indolinyl)carboximidamide

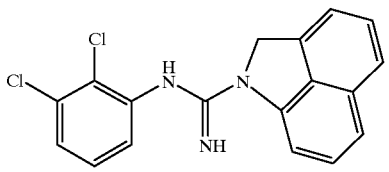

N-(2,3-dichlorophenyl)-(1-benz[cd]indolinyl)carboximidamide

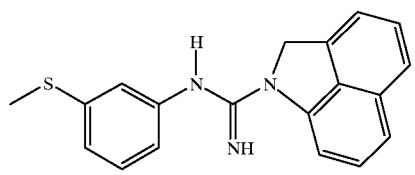

N-(3-methylmercaptophenyl)-(1-benz[cd]indolinyl)carboximidamide

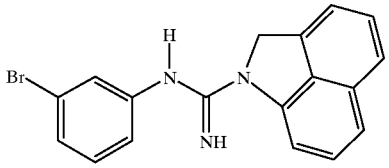

N-(3-bromophenyl)-(1-benz[cd]indolinyl)carboximidamide

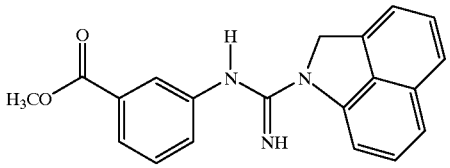

N-(3-methylcarboxylphenyl)-(1-benz[cd]indolinyl)carboximidamide

Specifically preferred compounds of Formula V include the following:
N-(1-naphthyl)-1-(5,6-dihydrophenanthridinyl) carboxuizdarnide;
N-(4benzyloxyphenyl)-1-(5,6-dihydrophenanthridinyl) carboimidamide;
N-(4methoxynaphthyl)-1-(5,6-dihydrophenanthridinyl) carboximidamride;
N-(3,4-dichlorophenyl)-1-(5,6-dihydrophenanthridinyl) carboxirndarnide;
N-(5-acenaphthyl)-1-(5-methoxy)-1-(5,6-dihydrophenanthridinyl) carboxiidamnide;
N-(5-acenaphchyl)-1-(5-bromo)-(5,6-diydrophenanthridinyl) carboximidamide;
N-(1-naphthyl)-1-(7-erhyl)-(5,6-dihydrocphenanthridinyl) carboximidamide;
N-(4-sec-butylphenyl)-1-(5,6-dihydrophenanthridinyl) carboximidamide;
N-(2,3-dichlorophenyl)-1-(5,6-dihydrophenanthridinyl) carboximidamide;
N-(2,3-dimethylphenyl)-1-(5,6-dihydrophenantlridinyl) carboxinidaniide;
N-(5,6,7,8-terrahydro-1-naphthyl)-1-(5,6-dihydrophenanthridinyl) carboximidarnide;
N-(2-biphenyl)-1-(5,6-dihydrophenanthridinyl) carboximidamide;
N-(3-biphenyl)-1-(5,6-dihydrophenanthridinyl) carboximidarnide;
N-(1-naphthyl)-1-(5,6-dihydrophenanthridinyl)carbo,ximidamide;

N-(1-naphthyl)-1-(7-trifluoromethyl)-(5,6-dihydrophenanthridinyl) carboximidamide;
N-(2-methylphenyl)-1-(5,6-dihydrophenanthridinyl) carboximidamide;
N-(3-ethylphenyl)-1-(5,6-dihydropheanthridinyl) carboximidamide;
N-(2,5-dimethylphenyl)-1-(5,6-dihydrophenanthridinyl) carboximidarnide;
N-(2-ethylphenyl)-1-(5,6-dihydrophenanthridinyl) carboxirnidamide;

and pharmaceutically acceptable salts of said compounds.

Specificallv preferred compounds of Formula VI include the following where the where the compound is structurally depicted above the chernical name thereof, and pharmaceutically acceptable salts of these depicted compounds:

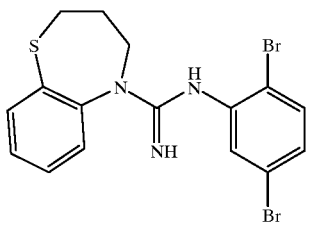

N-(2,5-dibromophenyl)-2,3,4,5-tetrahydro-[1,5]-benzothiazepin-5-yl)carboximidamide;

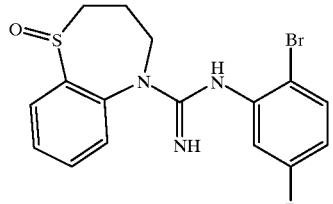

N-(2,5-dibromophenyl)-(1-oxo-2,3,4,5-tetrahydro-[1,5]-benzothiazepin-5-yl)carboximidamide;

Specifically preferred compounds of Formula VII include the following where the where the compound is structurally depicted above the chemical name thereof, and pharmaceutically acceptable salts of these depicted compounds:

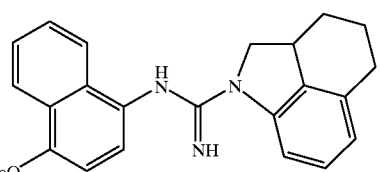

N-(4-methoxynaphthyl)-1-(2a,3,4,5-tetrahydrobenz[cd]indolinyl)-carboxidamide

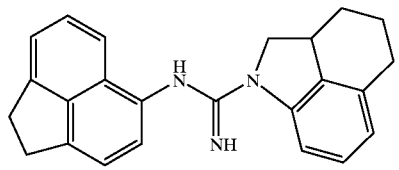

N-(5-acenaphthyl)-1-(2a,3,4,5-tetrahydrobenz[cd]indolinyl)-carboximidamide

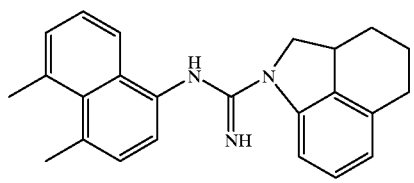

N-(4,5-dimethylnaphthyl)-1-(2a,3,4,5-tetrahydrobenz[cd]indolinyl)-carboximidamide

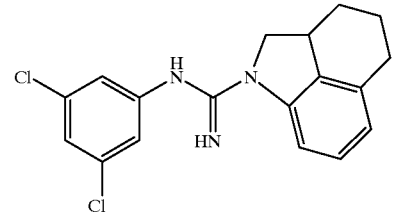

N-(3,5-dichlorophenyl)-1-(2a,3,4,5-tetrahydrobenz[cd]indolinyl)-carboximidamide

Specifically preferred compounds of Formulae VIII and IX include the following where the where the compound is structurally depicted above the chemical name thereof, and pharmaceutically acceptable salts of these depicted compounds:

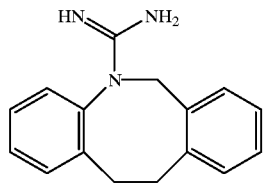

1-(5,6,11,12-tetrahydrodibenz[b, f]azocin)-carboximidamide

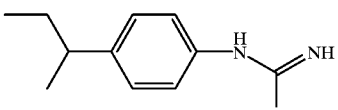

N-(4'-sec-butylphenyl)-1-(5,6,11,12-tetrahydrodibenz[b,f]azocin) carboximidamide

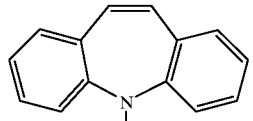

1-(dibenz[b, f]azepinyl)carboximidamide

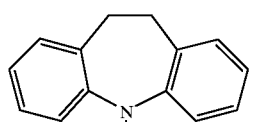

1-(10,11-dihydro-[5H]-dibenz[b, f]azepinyl)carboximidamide

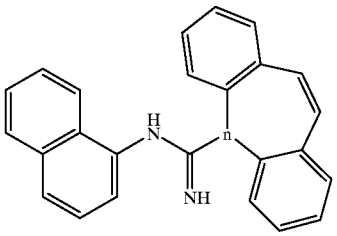

N-(1-naphthyl)-1-(dibenz[b, f]azepinyl)carboximidamide

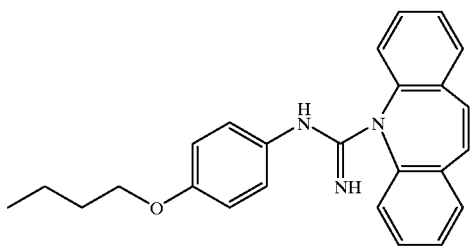

N-(4-butoxyphenyl)-1-(dibenz[b, f]azepinyl)carboximidamide

Excluded from certain aspects of the invention are N-(alkylphenyl)-1-indolinylcarboximidamide compounds (i.e. compounds of Formula I where X is $CH_2$ and R is alkyl-substituted phenyl, particularly where $R^1$ is H), specifically N-(mono-alkylphenyl)-1-indolinylcarboximidamide such as N-(m-ethylphenyl)-1-indolinyl carboximidarnide; as well as compounds of the invention where R is acenaphthyl, particularly where R is unsubstituted acenaphthyl and/or ring substituents $R^2$ and $R^3$ are each only hydrogen, and/or where X is $CH_2$ in the case of Formulae I and II, and/or one of R and $R^1$ is hydrogen; as well as compounds of Formula III where R or $R^1$ is aralkyl, particularly where ring substituents $R^2$ and $R^3$ are each only hydrogen, and/or R and $R^1$ are each other than hydrogen.

Compounds of the invention can be prepared by the reaction of a suitable precursor compound, e.g. indolinyl (or derivative thereof) compound, 1,2,3,4-tetrahydroquinolinyl (or derivative thereof) compound, 1,2,3,4-tetrahydroisoquinolinyl compound, benz[cd]indolinyl compound, 5,6-dihydrophenandhridinyl compound, 2,3,4,5-tetrahydro-[1,5]-benzothiazepine compounds (or derviative thereof, e.g. where X is other atom), 2a,3,4,5-tetrabenz[cd] indoline compound, 5,6,11,12-tetrahydrodibentb,flazocine compound, etc. (depending on whether a compound of Formulae I, I", II, II", III, IV, V, VI, VII, VIII or IX respectively, is being prepared) with a preformed alkyl or aryl cyanamide (see S. R. Safer, et al., *J. Org. Chem.*, 13:924 (1948)) or the corresponding N-substituted alkyl or aryl cyanamide. Typically, a salt of the amine (e.g. an HCl salt) is reacted with the cyanamide.

More particularly, compounds the invention can be suitably prepared by reaction of an appropriate indolinyl (or derivative thereof) salt (to prepare compounds of Formulae I, I', I", Ia, Iaa or Ib), 1,2,3,4-tetrahydroquinolinyl (or derivative thereof) salt (to prepare compounds of Formulae II, II", IIa, IIaa or Ib), 1,2,3,4-tetrahydroisoquinolinyl salt (to prepare compounds of Formulae III, IIIa, IIIaa or IIIb), benz[cd]indolinyl salt (to prepare compounds of Formulae IV, IVa, IVaa or IVb), or 5,6-dihydrophenanthridinyl salt (to prepare compounds of Formulae V, Va, Vaa or Vb) or other appropriate salt such as salts of above mentioned precursor compounds (to form compounds of Formulae VI–IX) with a substituted cyanamide in a suitable solvent such as toluene, chlorobenzene or the like under an inert atmosphere such as argon or nitrogen as exemplified in the Scheme below. The reaction solution is then heated e.g. from about 110° to 120° C. for 2 to about 16 hours until reaction completion, e.g. as indicated by thin layer chromatography. The reaction solution is then cooled to room temperature, and the solvent is then removed under reduced pressure to provide the desired compound of the invention. The crude product then can be purified by recrystallization and/or column chromatography, e.g. by elution one or more times on silica gel (e.g., 60–200 mesh, 50× w/w) with suitable solvents. See Example 2 which follows for exemplary conditions.

The indolinyl (or derivative thereof), 1,2,3,4-tetrahydroquinoline (or derivative thereof), 1,2,3,4-tetrahydroisoquinoline, benz[cd]indolinyl or 5,6-dihydrophenanthridinyl ot other presursor such as those mentioned above (for Formulae VI–IX) and cyanamide reagents with appropriate substituents are commercially available or can be readily prepared by known procedures. For example, the cyanamide starting material can be synthesized from the correspondingly substituted amine by treatment with cyanogen bromide (BRCN) in a suitable solvent such as dry ethyl ether or toluene at reduced temperatures (e.g. 0° C.) or room temperature. As exemplified in the Scheme below, the amine to be reacted with cyanogen bromide is substituted with the R moiety as defined above for Formulae I, I", II, II", III, IV, V, VI, VII, VIII or IX (in the Scheme, that R moiety is exemplified as phenyl which may be ring-substituted by groups $R_1$ and $R_2$). Thus, various R groups of compounds of Formula I through IX (Which includes Formulae I" and II") can be provided by use of suitable substituted amies that are reacted with BrCN, such as e.g. substituted and unsubstiruted anilines as shown in the Scheme, substituted and unsubstituted 1-naphthylarine, 2-naphthylamine, acenaphthylamine, etc. $R^1$ groups other than hydrogen of compounds of Formulae I through IX can be readily provided by reaction of a substituted cyanamide with a suitable nucleophile such as a halide reagent (e.g., a substituted or unsubstiruted alkyl or alklnyl iodide or bromide). Thus, as exemplified in the Scheme below, the aryl cyanamide is reacted with NaH in a solvent of tetrahydrofuran and reacted with the iodide reagent $R^1$-I, such as substituted or unsubstituted methyl, ethyl, propyl, butyl, etc. iodide, an alkenyl iodide, etc. Also, compounds of the invention having an $R^1$ group of methyl can be prepared by reaction of a mono-substituted amine (e.g., an aniline, naphthylamine or acenaphthylamine) with formic acid followed by treatment with lithium aluminum hydride to provide the corresponding methyl-substituted cyanamide (e.g., $C_6H_5N(CH_3)CN$ from unsubstituted aniline). Alkylsulfmyl-substituted or alkylsulfonyl-substituted reagents, that can provide correspondingly substituted compounds of the invention as described above, can be provided by oxidation (e.g., $H_2O_2$) of alkylthio-substituted reagents. See for instance Example 46 which follows.

While the Scheme depicts preparation of compounds of Formula I, the same procedures can be employed to prepare compounds of Formulae I', II, II", III, IV, V, VI, VII, VIII or IX by use of a 1,2,3,4-tetrahydroquinolinyl (or derivative thereof) salt, 1,2,3,4-tetrahydroisoquinolinyl salt, benz[cd] indolinyl salt or 5,6-dihydrophenanthridinyl salt or other corresponding salt for compounds of Formulae VI through IX, respectively, in place of the indolinyl salt shown in the Scheme.

SCHEME

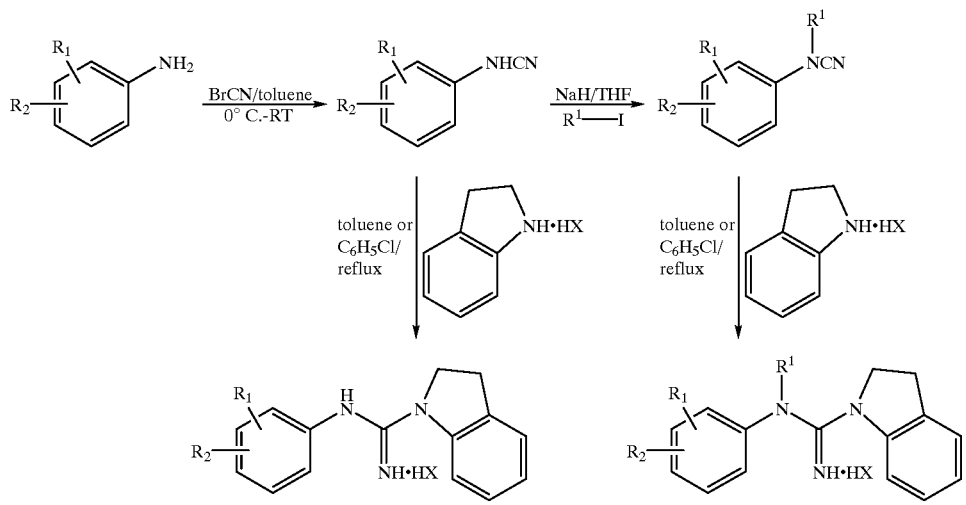

Compounds of Formula II where R and $R^1$ are each hydrogen can be prepared by reaction of 1,2,3,4-tetrahydroquinoline compound with cyanamnide. $R^2$ substituents can be provided by reaction of a substituted or unsubstituted quinoline compound with a Grignard reagent followed by hydrogenation to provide the substituted 1,2,3,4-tetrahydroquinoline compound. See Example 3 which follows for an exemplary procedure. See also Examples 41 and 42 which follow. Compounds of Formulae I", II" and VI where X is —S(O)— or —S(O)$_2$— can be prepared by oxidation (e.g. with H$_2$O$_2$ and/or with sodium periodate) of the corresponding preformed compounds where the ring member X is —S—. See for instance Example 47 which follows.

The amine starting materials are commercially available andior can be readily prepared. For example, benz[cd] indoline and 5,6-dihydrophenanthridine reagents can be prepared treatment of a benz[cd]indo-2(1H)-one compound or 5,6-dihydrophenanthridinone compound with a base such as diborane in a suitable solvent such as tetrahydrofuran. See Example 1 which follows for exemplary conditions. Chiral compounds of the invention may be used as optically enriched or racemic mixtures. An optically enriched mixture contains substantially more (e.g. about 60%, 70%, 80% or 90% or more) of one enantiomer or diastereoisomer than the other stereoisomers. Optically enriched mixtures can be obtained by known procedures, e.g., column chromatography using an optically active binding material or formation of a salt using an optically active material, particularly an optically active acid. Particularly preferred optically enriched mixtures include sulfinyl-containing compound of the invention, e.g. compounds of Formulae I", II" or VI where X is —S(O)—, or compounds having having an alkylsulfmyl or other sulfinyl substituent. Such optically active mxtures of sulfinyl-containing compounds can be readily prepared, e.g. by column chromatography using an optically active binding material.

As discussed above, the present invention includes methods for treating preventing certain neurological disorders, including the consequences of stroke, heart attack and traumatic head or brain injury, epilepsy or neurodegenerative diseases comprising the administration of an effective amount of one or more compounds of the invention to a subject including a mammal, particularly a human, in need of such treatment. In particular, the invention provides methods for treatment and/or prophylaxis of nerve cell death (degeneration) resulting e.g. from hypoxia, hypoglycemia, brain or spinal cord ischemia, brain or spinal cord trauma, stroke, heart attack or drowning. Typical candidates for treatment include e.g. heart attack, stroke and/or persons suffering from cardiac arrest neurological deficits, brain or spinal cord injury patients, patients undergoing major surgery such as heart surgery where brain ischemia is a potential complication and patients such as divers suffering from decompression sickness due to gas emboli in the blood stream. Candidates for treatment also will include those patients undergoing a surgical procedure involving extracorporal circulation such as e.g. a bypass procedure.

The invention in particular provides methods for treatment which comprise administration of one or more compounds of the invention to a patient that is undergoing surgery or other procedure where brain or spinal cord ischemia is a potential risk. For example, carotid endarterectomy is a surgical procedure employed to correct atherosclerosis of the carotid arteries. Major risks associated with the procedure include intraoperative embolization and the danger of hypertension in the brain following increased cerebral blood flow, which may result in aneurism or hemorrhage. Thus, an effective amount of one or more compounds of the present invention could be administered pre-operatively or peri-operatively to reduce such risks associated with carotid endarterectomy, or other post-surgical neuorological deficits.

The invention further includes methods for prophylaxis against neurological deficits resulting from e.g. coronary artery bypass graft surgery and aortic valve replacement surgery, or other procedure involving extra-corporal circulation. Those methods will comprise administering to a patient undergoing such surgical procedures an effective amount of one or more compounds of the invention, typically either pre-operatively or peri-operatively.

The invention also provides methods for prophylaxis and treatment against neurological injury for patients undergoing myocardial infarction, a procedure that can result in ischemic insult to the patient. Such methods will comprise administering to a patient undergoing such surgical procedure an effective amount of one or more compounds of the invention, typically either pre-operatively or peri-operatively.

Also provided are methods for treating or preventing neuropathic pain such as may experienced by cancer patients, persons having diabetes, amputees and other persons who may experience neuropathic pain. These methods for treatment comprise administration of an effective amount of one or more compounds of the invention to a patient in need of such treatment.

The invention also provides methods for treatment and prophylaxis against retinal ischemia or degeneration and resulting visual loss. For example, a compound of the invention can be administered parenterally or by other procedure as described herein to a subject a suffering from or susceptible to ischemic insult that may adversely affect retinal function, e.g., significantly elevated intraocular pressures, diseases such as retinal artery or vein occlusion, diabetes or other ischemic ocular-related diseases. Post-ischemic administration also may limit retinal damage. The invention also includes methods for treating and prophylaxis against decreased blood flow or nutrient supply to retinal tissue or optic nerve, or treatment or prophylaxis against retinal trauma or optic nerve injury. Subjects for treatment according to such therapeutic methods of the invention may be suffering or susceptible to retinal ischemia that is associated with atherosclerosis, venous capillary insufficiency, obstructive arterial or venous retinopthies, senile macular degeneration, cycstoid macular edema or glaucoma, or the retinal ischemia may be associated with a tumor or injury to the mammal. Intravitreal injection of a compound of the invention also may be a preferred administration route to provide more direct treatment to the ischemic retina.

The invention also provides methods for treatment of a subject suffering from shingles as well as treatment of a person suffering from or susceptible to migraines, particularly to alleviate the pain and discomfort associated with those disorders. These methods comprise administration of an effective amount of one or more compounds of the invention to a patient in need of treatment.

The invention further provides a method of treating Korsakoff's disease, a chronic alcoholism-induced condition, comprising administering to a subject including a mammal, particularly a human, one or more compounds of the invention in an amount effective to treat the disease. Compounds of the invention are anticipated to have utility for the attenuation of cell loss, hemorrhages and/or amino acid changes associated with Korsakoff's disease.

As discussed above, the invention also includes methods for treating a person suffering from or susceptible to cerebral palsy, emesis, narcotic withdrawal symptoms and age-dependent dementia, comprising administering to a subject including a mammal, particularly a human, one or more compounds of the invention in an amount effective to treat the condition.

As discussed above, preferred compounds of the invention in a standard anticonvulsant in vivo audiogenic test, such as the audiogenic mouse assay of Example 48 which follows, where DBA/2 mice about 20–23 days old are injected intraperitoneally with a test compound 30 minutes prior to being placed in a bell jar with exposure to auditory stimulus of 12 KHz sine wave at 110–120 db. References herein in vivo "audiogenic assay" are intended to refer to that protocol. Generally preferred compounds exhibit 20% or more inhibition (relative to subjects treated with vehicle control only) at a dose of 20 mg/kg, more preferably about 50% or more or 70% or more inhibition at a dose of 20 mg/kg in such an in vivo audiogenic assay. As discussed above, activity in the audiogenic assay has been recognized as indicative that a test compound has neuroprotective properties. See, e.g., M. Tricklebank et al., *European Journal of Pharmacology*, supra; T. Seyfried, *Federation Proceedings*, supra.

The invention also provides methods for determining binding activity of compounds of the invention as well as in vitro and in vivo binding activity diagnostic methods using one or more radiolabelled compounds of the invention, e.g., a compound of the invention that is labeled with $^{125}$I, tritium, $^{32}$P, $^{99}$Tc, or the like, preferably 125I. For instance, a compound of the invention having a phenyl or other aryl substituent that is ring substituted with one or more $^{125}$I groups can be administered to a mammal and the subject then scanned for binding of the compound. Specifically, single photon emission computed tomography ("SPECT") can be employed to detect such binding. Such an analysis of the mammal could e.g. aid in the diagnosis and treatment of acute cerebral ischemia. That is, a labeled compound of the invention will selectively bind to ischernic tissue of e.g. a subject's brain to differentiate between ischemic and non-ischemic tissue and thereby assess trauma or other injury to the brain.

Accordingly, the invention includes compounds of the invention that contain a radiolabel such as $^{125}$I, tritium, $^{32}$P, $^{99}$Tc, or the like, preferably $^{125}$I. Such radiolabelled compounds can be suitably prepared by procedures known in the synthesis art. For example, a compound of the invention having an aromatic group, such as phenyl, that has a bromo or chloro ring substituent can be employed in an exchange labeling reaction to provide the corresponding compound having an $^{125}$I ring substituent.

Compounds of the invention may be used in therapy in conjunction with other medicaments. For example, for treatment of a stroke victim or a person susceptible to stroke, one or more compounds of Formulae I, II, III, IV or V, or one or compounds of Formulae I", II", VI, VU, VIII or IX, may be suitably administered together with a pharmaceutical targeted for interaction in the blood clotting mechanism such as streptokinase, tPA, urokinase and other agents that lyse clots. Also, one or more compounds of the invention may be administered together with agents such as heparin and related heparin-based compounds, acenocoumarol or other known anticoagulants.

The compounds of this invention can be administered intranasally, orally or by injection, e.g., intramuscular, intraperitoneal, subcutaneous or intravenous injection, or by transdermal, intraocular or enteral means. The optimal dose can be determined by conventional means. Compounds of the present invention are suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc.

Compounds of the invention can be employed, either alone or in combination with one or more other therapeutic agents as discussed above, as a pharmaceutical composition in mixture with conventional excipient, i.e., pharmaceutically acceptable organic or inorganic carrier substances suitable for parenteral, enteral or intranasal application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Intravenous or parenteral administration, e.g., subcutaneous, intraperitoneal or intramuscular administration are preferred. The compounds of this invention are particularly valuable in the treatment of mammalian subjects, e.g., humans, to provide neuroprotective therapy and/or prophylaxis. Typically, such subjects include those afflicted with neurodegenerative diseases such as Parkinson's disease, Huntington's disease, Amyotrophic Lateral Sclerosis, Alzheimer's disease, Down's Syndrome and Korsakoff's disease. Also suitable for treatment are those subjects suffering from or likely to suffer from nervous system dysfunctions resulting from, for example, epilepsy or nerve cell degeneration which is the result of hypoxia, hypoglycemia, brain or spinal chord ischemia or brain or spinal chord trauma. As discussed above, typical candidates for treatment include heart attack, stroke, brain or spinal cord injury patients, patients undergoing major surgery where brain or spinal cord ischemia is a potential complication and patients such as divers suffering from decompression sickness due to gas emboli in the blood stream.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. In general, a suitable effective dose of one or more compounds of Formulae I, II, III, IV or V, or one or compounds of Formulae I", II", VI, VII, VIII or IX, particularly when using the more potent compound(s) of Formulae I, II, III, IV or V, or one or compounds of Formulae I", II", VI, VII, VIII or IX, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day. The desired dose is suitably administered once daily, or several sub-doses, e.g. 2 to 4 sub-doses, are administered at appropriate intervals through the day, or other appropriate schedule. Such sub-doses may be administered as unit dosage forms, e.g., containing from 0.05 to 10 milligrams of compound(s) of Formulae I, II, III, IV or V, or one or compounds of Formulae I", II", VI, VII, VIII or IX, per unit dosage, preferably from 0.2 to 2 milligrams per unit dosage.

Compounds of the invention also should be useful as rubber accelerators. See U.S. Pat. No. 1,411,713 for a discussion of rubber accelerator applications.

The entire text of all documents cited herein are incorporated by reference herein. The following non-limiting examples are illustrative of the invention.

GENERAL COMMENTS

In the following examples, all percentages reported herein, unless otherwise specified, are percent by weight. All temperatures are expressed in degrees Celsius.

Melting points were determined in open capillary tubes on a Thomas-Hoover apparatus and are uncorrected. Thin-layer chromatography was performed on Baker-flex 1B2-F silica gel plates. Compounds were visualized on TLC with 254-nM UV light or as a blue spot with bromcresol spray reagent (Sigma Chemical Co.). Preparative TLC was performed on Analtech GF precoated silica gel (1000 $\mu$m) glass-backed plates (20×20 cm). The IR, $^1$H and $^{13}$C NMR spectra of all compounds were consistent with their assigned structures. NMR spectra were recorded on Varian Gemini 300 and the chemical shifts were reported in ppm ($\delta$) relative to the residual signal of the deuterated solvent (CDCl$_3$, $\delta$ 7.26; CHD$_2$OD, $\delta$ 3.30). Elemental analyses were performed by either Galbraith Laboratories (Knoxville, Tenn.) or MHW Laboratories (Tuscon, Ariz.). High Resolution Mass spectra (HRMS) were recorded on a Finnegan MAT 90. HPLC were performed on a C18 reverse phase column using 50:50 water:acetonitrile with 0.1% TFA as a mobile phase. BrCN was obtained from Aldrich Chemical Co., and was used as received. All starting amines were obtained from commercial sources and were purified by standard procedures before use, or they were prepared by published procedures. Chlorobenzene, ether (Et$_2$O) and tetrahydrofuran (THF) were anhydrous quality solvents (Sure Seal) supplied by Aldrich. All other solvents were reagent grade. Alkyl- and arylcyanamides were prepared as described above and according to published procedures (e.g., PCT/US92/01050) by reaction of the amines with BrCN in ether.

EXAMPLE 1

1(a). Preparation of Benz[cd]indoline HCl salt

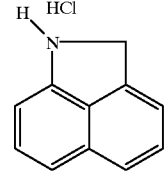

To a cooled (ice bath) solution of Benz[cd]indo-2(1H)-one (9.0 g, 53.2 mmol) in tetrahydrofuran (50 ml) was added dropwise 100 ml of diborane 1M in tetrahydrofuran (100 mmol) under argon. The resulting mixture was refluxed for 12 hours and quenched with aqueous HCl (1M) at 0–5° C. The solution was basified to pH 14 by adding NaOH 1N and the product extracted with chloroform. The combined organic layers were washed with brine and dried over MgSO$_4$. Flash column chromatography (silica gel, 2:1 hexane/dichloromethane) afforded Benz[cd]indoline (5.58 g, 67.6%). To form the HCl salt, Benz[cd]indoline (1.0 g, 6.44 mmol) was then dissolved in a minimum amount of diethyl ether and 15 ml of 1M HCl diethyl ether solution was added. The precipitate was collected by filtration, washed with diethyl ether and dried to afford Benz[cd]indoline HCl (1.21 g, 98%) as a white solid. $^1$H-NMR (CD$_3$OD): $\delta$ ppm 7.90–7.55 (m, ArH, 6H), 5.16 (s, ArCH2, 2H).

1(b). Preparation of 6-Dihydrophenanthridine HCl salt

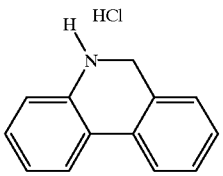

The title compound was obtained as a white solid from 6(5H)-phenanthridinone by the method described in Example 1(a) above in 12% yield. $^1$H-NMR (CD$_3$OD): δ ppm 8.12–7.45 (m, ArH, 6H), 4.59 (s, ArCH2, 2H).

EXAMPLE 2

Preparation of N-(1-Naphthyl)-1-indolinylcarboximidamide (Formula I: R=1-naphthyl, $R^1$=hydrogen, m=n=0)

Part 1: Preparation of 1-Naphthylcyanamide

Cyanogen bromide (4.4 gm, 41.9 mmol) was added in portions to the stirred and ice-bath cooled solution of 1-aminonaphthalene (10.0 gm, 69.8 mmol) in toluene (100 mL. After 0.5 hour, the cooling bath was removed the reaction mixture was stirred at room temperature for 12 hours. The precipitate was filtered and the solid was triturated with water (150 mL) for 0.5 hour. The resulted solid was filtered and washed with water (4×20 mL) and the solid was dried in vacuum oven at 40° C. This material (4.6 gm) was used as such without any further purification.

Part 2: Preparation of N-(1-Naphthyl)-1-indolinylcarboximidamide mesylate

A mixture of 1-naphthylcyanamide (610 mg, 3.63 inmol), indoline mesylate (663 m, 3.09 mmol) and chlorobenzene (18 ml) in a round bottom flask were heated to reflux on an oil bath for 4 hours. The reaction was allowed to cool to room temperature, solvent was removed by rotavapor, and the residue was chromatographed on silica gel using a mnixture of hexanes: ethyl acetate (2:1) followed by chloroform/methanol (10:1) as eluents. The white foam-solid obtained upon concentration of fractions was treated with diethyl ether for overnight. White solid was filtered washed with diethyl ether to give the title product as free base as white solid; mp: 151–155° C.; TLC (CHCl$_3$:MeOH; 10:1); R$_f$=0.23; $^1$H NMR(CDCl$_3$): 8.173–8.144 (m, ArH, 1H), 7.856–7.826 (m, ArH, 2H), 7.574–7.405 (m, ArH, 2H), 7.240–7.154 (m, ArH, 2H), 7.080–7.052 (m, ArH, 1H), 6.952–6.927 (m, ArH, 1H), 4.208–4.152 (t, J=8.45 Hz, CH$_2$, 2H), 3.231–3.174 (t, J=8.45 Hz, CH$_2$, 2H); Anal. Calcd. for C$_{19}$H$_{17}$N$_3$ 0.5H$_2$O; C: 77.0, H: 6.07, N: 14.18; Found C: 76.10, H: 5.78, N: 13.98.

EXAMPLE 3

Preparation of (±) 2-(4-tert-butylphenyl)-6-isopropyl-1-(1,2,3,4-(tetrahydroquinolinylcarboximidamide) hydrochloride (Formula II: hydrochloride salt of R= $R^1$=H, $R^2$=2-(4-tert-butylphenyl), $R^3$=6-isopropyl, X=CH$_2$, m=n=1)

Part 1: Preparation of 2-(4-tert-butylphenyl)-6-isopropylquinoline

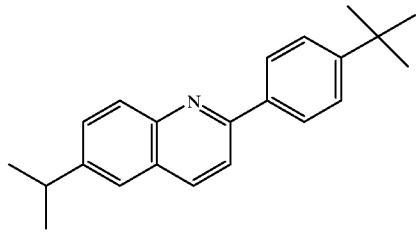

To a cooled (ice bath) 2M diethyl ether solution of 4-tert-butylphenylmagnesium bromide (15 ml, 0.03 mol) was added dropwise under argon 15 ml of a tetrahydrofuran solution of 6-isopropylquinoline (5.13 g, 0.03 mol). The resulting mixture was refluxed for 5 hours, stirred at room temperature for 12 hours and quenched with water (80 ml). The yellow precipitate obtained was then filtered and washed with hexane. CrystaUization in hexane:chloroform 40:1 yielded 3.7 g of pure (±)-2-(4-tert-burylphenyl)-6-isopropylquinoline (40% yield). $^1$H NMR(CDCl$_3$): 8.2 (m, ArH, 4H), 7.84 (m, ArH, 1H), 7.60 (m, ArH, 4H), 3.12 (s, CH(Me)$_2$, 1H), 1.4 (s, CH(Me)$_2$ and C(Me)$_3$, 15H); Mass/Cl-NH$_3$: MH$^+$304.

Part 2: Preparation of (±)-2-(4-tert-butylphenyl)-6-isopropyl-1,2,3,4-tetrahydroquinoline hydrochloride

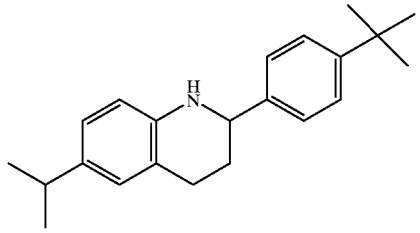

2-(4-tert-butylphenyl)-6-isopropylquinoline (2.5 g, 8.2 mmol) was dissolved in 100 ml of methanol; platinum (IV) oxide (300 mg, 1.3 mmol) was added and the suspension hydrogenated at 50 psi for 12 hours. The catalyst was filtered off on a bed of celite and 20 ml of 1N HCl in ethyl ether was added to the filtrate which was then concentrated to yield crude (±)-2-(4tert-butylphenyl)-6-isopropyl-1,2,3,4- tetrahydroquinoline hydrochloride. Mass/Cl-NH₃: MH⁺308.

Part 3: Preparation of (±)-2-(4-tert-butylphenyl)- 6-isopropyl-1-(1,2,3,4-tetrahydroquinolinecarboximidamide hydrochloride

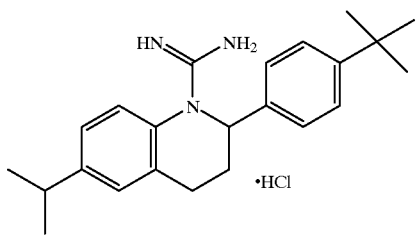

The crude (±)-2-(4-tert-burylphenyl)-6-isopropyl-1,2,3,4-tetrahydroquinoline hydrochloride (300 mg, approximately 0.8 mmol) obtained in Part 2 above and cyanarnide (350 mg, 8 mmol) were dissolved in ethanol and the mixture heated to reflux for 2 days. The solvent was evaporated, water was added and the product extracted with ethyl acetate. The crude product was purified on silica gel with chloroform: methanol 9:1 as eluant. The obtgained solid was washed successively with water and ethyl ether to yield (±) 2-(4-tert-butylphenyl)-6-isopropyl-1-(1,2,3,4-tetrahydroquinoliylcarboximidamide) hydrochloride (70 mg, 21%). ¹H NMR(CD₃OD): δ ppm 7.40 (m, ArH, 3H), 7.20 (m, ArH, 4H), 5.30 (M, CHN, 1H), 2.90 (s, CH(Me)₂, 1H), 2.70 (m, CH₂, 2H), 1.9 (m, CH₂, 2H), 1.25 and 1.28 (s, CH(Me)₂ and C(Me)₃, 15H); Mass/Cl-NH₃: MH⁺350.

EXAMPLES 4–47

By methods indicated above in Examples 1–3 and using appropriately substituted reagents, the following compounds were prepared having the specified physical characteristics.

EXAMPLE 4

N-(4-Benzyloxyphenyl)-1-indolinylcarboximidamide•mesylate (Formula I: mesylate salt of R=4-benzyloxyphenyl, R¹=H, m=n=0)

White solid; mp: 144–145° C.; TLC (CHCl₃:MeOH; 10:1); R$_f$=0.37; ¹H NMR (CDCl₃): 7.391–6.858 (m, ArH, 13H), 5.000 (s, CH₂, 2H), 3.894–3.841 (t, J=7.97 Hz, CH₂, 2H), 3.143–3.090 (t, J=7.97 Hz, CH₂, 2H), 2.706 (s, CH₃, 3H); Anal. Calcd. for C₂₃H₂₅N₃SO₄: C: 62.85, H: 5.74, N: 9.57; Found: C: 62.66, H: 5.50, N: 9.38.

EXAMPLE 5

N-(4-Methoxynaphthyl)-1-indolinylcarboximide•mesylate (Formula I: mesylate salt of R=4-methoxynaphthyl, R¹=H, m=n=0)

White solid; mp: 151–155° C.; TLC (CHCl₃:MeOH; 10:1); R$_f$=0.23; ¹H NMR(CDCl₃): 8.313–7.097 (m, ArH, 9H), 6.723–6.695 (d, J=8.24 Hz, ArH, ¹H), 3.996 (s, OCH₃, 3H), 3.497–3.469 (t, CH₂, 2H), 2.971 (t, CH₂, 2H), 2.733 (s, CH₃, 3H); Anal. Calcd. for C₂₁H₂₃N₃SO₄: C: 61.00, H: 5.61, N: 10.17; Found: C: 61.15, H: 5.48, N: 10.08.

EXAMPLE 6

N-(3,4-Dichlorophenyl)-1-indolinylcarboximidamide (Formula I: R=3, 4dichlorophenyl, R¹=H, m=n=0)

White solid; mp: 133–134° C.; TLC (CHCl₃:MeOH; 10:1): R$_f$=0.29; ¹H NMR(CDCl₃): 7.697–7.670 (d, J=8.03 Hz, ArH, 1H), 7.370–7.342 (d, J=8.48 Hz, ArH, 1H), 7.208–7.090 (m, ArH, 3H), 6.939–6.811 (m, ArH, 2H), 4.097–4.040 (t, J=8.37 Hz, CH₂, 2H), 3.828 (s, OCH₃, 3H), 3.182–3.125 (t, J=8.37 Hz, CH₂, 2H); Anal. Calcd. for C₁₅N₁₃N₃Cl₂: C: 58.84, H: 4.28, N: 13.72; Found: C: 59.00, H: 4.44, N: 13.51.

EXAMPLE 7

N-(5-Acenaphthyl)-1-(5-methoxy)-1-indolinylcarboximidamide•HCl (Formula I: hydrochloride salt of R=5-aceraphthyl, R¹=H, m=n=1, R³=methoxy (at 5-indoline position))

Yellow solid; mp: 124–127° C.; TLC (CHCl₃:MeOH; 10:1); R$_f$=0.30; ¹H NNMR(CDCl₃): 7.744–6.674 (m, ArH, 8H), 3.982–3.971 (m, CH₂, 2H), 3.777 (s, OCH₃, 3H), 3.433–3.334 (m, CH₂, 4H), 3.117–3.061 (t, J=8.31 Hz, CH₂, 2H); Anal. Calcd. for C₂₂H₂₂N₃ClO: C: 69.56, H: 5.84, N: 11.06; Found: C: 69.45, H: 5.98, N: 10.96.

EXAMPLE 8

N-(5-Acenaphthyl)-1-(5-bromo)-indolinylcarboximidamide (Formula I: R=5-acenaphthyl, R¹=H, m=0, n=l, R³=bromo (at 5-indoline position))

Yellow foam; mp: 80–85° C.; TLC (CHCl₃:MeOH; 10:1); R$_f$=0.35; ¹H NMR(CDCl₃): 7.856–7.828 (d, J=8.52 Hz, ArH, 1H), 7.683–6.656 (d, J=8.24 Hz, ArH, 1H), 7.422–7.395 (t, ArH, 1H), 7.372–7.212 (m, ArH, 2H), 6.995–6.971 (d, ArH, J=7.21 Hz, 1H), 4.185–4.128 (t, J=8.51 Hz, CH₂, 2H), 3.437–3.343 (m, CH₂, 2H), 3.206–3.148 (t, J=8.73 Hz, CH₂, 2H); Anal. Calcd. for C₂₁H₁₈N₃Br: C: 64.30, H: 4.62, N: 10.71; Found: C: 64.56, H: 4.34, N: 10.25.

EXAMPLE 9

N-(1-Naphthyl)-1-(7-ethyl)-indolinylcarboximidamide (Formula I: R=1-naphthyl, R¹=H, m=0, n=l, R³=ethyl (at 7-indoline position))

White solid; mp: 160–164° C.; TLC (CHCl₃:MeOH; 10:1); R$_f$=0.40; ¹H NMR(CDCl₃): 7.861–7.081 (m, ArH, 10H), 3.064–3.044 (br, CH₂, 2H), 2.858–2.783 (q, CH₂, 2H), 1.333–1.282 (t, J=7.54 Hz, CH₃, 3H); Anal. Calcd. for C₂₁H₂₁N₃: C: 79.97, H: 6.71, N: 13.32; Found: C: 79.90, H: 6.85, N: 13.33.

EXAMPLE 10

N-(4-sec-butylphenyl)-1-indolinylcarboximidamide•mesylate (Formula I: mesylate salt of R=4-sec-butylphenyl, R¹=H, m=n=0)

White solid; TLC (CHCl₃:MeOH; 10:1); R$_f$=0.28; ¹H NMR (CDCl₃): 7.21–6.93 (m, 3H, ArH), 4.00 (t, 2H, J=8 Hz, —Ar—CH₂—), 3.13 (t, 2H, J=8 Hz, —NCH₂—), 2.68 (s, 3H, CH₃SO₃H), 2.55–2.45 (m, 1H, —CH—), 1.58–1.45 (m, 2H, —CH₂—), 1.16 (d, 3H, J=7 Hz, —CH₃), 0.74 (t, 3H, J=7.3, —CH₃); HPLC: 98.6%; Rtn time: 18.6 minutes; MS: 294 (M⁺).

EXAMPLE 11

N-(2,3-dichlorophenyl)-1-indolinylcarboximidamide•HCl (Formula I: hydrochloride salt of R=2,3-dichlorophenyl, R¹=H, m=n=0)

Light gray powder; mp: 187–187° C.; TLC (CH₂Cl₂:MeOH; 11:1); R$_f$=0.35; ¹H NMR(CD₃OD):

7.621–7.589 (q, 1H. J=3.26 Hz, ArH), 7.479–7.136 (m, 6H, ArH), 4.247–4.194 (t, 2H, J=8.04 Hz, $CH_2$), 3.301–3.247 (t, 2H, J=8.04 Hz, $CH_2$); Anal. Calcd. for $C_{15}H_{13}N_3Cl_2$ HCl 0.5$H_2O$ (351.67): C: 51.23, H: 4.30, N: 11.94, Cl: 30.24; Found: C: 51.14, H: 4.48, N: 11.76, Cl: 30.20.

EXAMPLE 12

N-(2,3-dimethylphenyl)-1-indolinylcarboximidamide•HCl (Formula I: hydrochloride salt of R=2,3-dimethylphenyl, $R^1$=H, m=n=0)

White powder; purity: 99.2% (HPLC); mp: 192–194° C.; TLC ($CH_2Cl_2$: MeOH; 11:1); $R_f$=0.48; $^1$H NMR($CD_3OD$): 7.46–7.13 (m, 7H, ArH), 4.22–4.17 (t, 2H, J=8.14 Hz, $CH_2$), 3.30–3.25 (t, 2H, J=8.14 Hz, $CH_2$), 2.37 (s, 3H, $CH_3$), 2.26 (s, 3H, $CH_3$).

EXAMPLE 13

N-(5,6,7,8-tetrahydro-1-naphthyl)-1-indoaiylcarboximidamide•HCl (Formula I: hydrochloride salt of R=5,6,7,8-tetrahydro-1-naphthyl, $R^1$=H, m=n=0)

Light gray powder; purity: 97.5% (HPLC); mp: 175–177° C.; TLC ($CH_2Cl_2$:MeOH; 11:1); $R_f$=0.53; $^1$H NMR ($CD_3OD$): 7.45–7.09 (m, 7H, ArH), 4.21–4.16 (t, 2H, J=8.15 Hz, $CH_2$), 3.29–3.24 (t, 2H, J=8.15 Hz, $CH_2$), 2.87–2.83 (t, 3H, J=5.88 Hz, $CH_3$), 2.76–2.72 (t, 3H, J=5.88 Hz, $CH_3$).

EXAMPLE 14

N-(2-biphenyl)-1-indolinylcarboximidamide•HCl (Formula I: hydrochloride salt of R=2-biphenyl, $R^1$=H, m=n=0)

Light gray powder; purity: 96.7% (HPLC); mp: 144–146° C.; TLC ($CH_2Cl_2$:MeOH; 11:1); $R_f$=0.44; $^1$H NMR ($CD_3OD$): 7.54–6.99 (m, 13H, ArH), 3.87–3.81 (t, 2H, J=8.11 Hz, $CH_2$), 3.10–3.05 (t, 2H, J=7.97 Hz, $CH_2$); Anal. Calcd. for $C_{21}H_{20}N_3Cl$ 0.5$H_2O$ (349.86): C: 70.28, H: 5.89, N: 11.70, Cl: 30.24; Found: C: 70.50, H: 6.03, N: 11.64.

EXAMPLE 15

N-phenyl-1-indolinylcarboximidarnide•HCl (Formula I: hydrochloride salt of R=phenyl, $R^1$=H, m=n=0)

White powder; purity: 99.0% (HPLC); mp: 222–224° C.; TLC ($CHCl_3$:MeOH; 10:1): $R_f$=0.10; $^1$H NMR ($CD_3OD$): 7.50–7.44 (m, 2H, Ar—H), 7.39–7.30 (m, 5H, Ar—H), 7.26–7.21 (m, 1H, Ar—H), 7.15–7.09 (m, 1H, Ar—H), 4.22–4.17 (t, 2H, J=8.20, $CH_2$), 3.29–3.23 (t, 2H, J=8.20, $CH_2$); Anal. Calcd. for $C_{15}H_{15}N_3$•HCl (273.77): C: 65.81, H: 5.89, N: 15.35; Found: C: 65.70, H: 5.78, N: 15.52.

EXAMPLE 16

N-(2-chlorophenyl)-1-indolinylcarboximidamide•HCl (Fornula I: hydrochloride salt of R=2-chlorophenyl, $R^1$=H, m=n=0)

White powder; purity: 98.8% (HPLC); mp: 172–174° C.; TLC ($CHCl_3$:MeOH; 10:1): $R_f$=0.19; $^1$H NMR ($CD_3OD$): 7.63–7.60 (m, 1H, Ar—H), 7.47–7.35 (m, 5H, Ar—H), 7.28–7.23 (m, 1H, Ar—H), 7.16–7.11 (m, 1H, Ar—H), 4.24–4.19 (t, 2H, J=8.10, $CH_2$), 3.29–3.24 (t, 2H, J=8.10, $CH_2$); Anal. Calcd. for $C_{15}H_{15}N_3Cl$•HCl (308.21): C: 58.46, H: 4.91, N: 13.63, Cl: 23.01; Found: C: 58.64, H: 5.10, N: 13.48, Cl: 22.88.

EXAMPLE 17

N-(2-tolyl)-1-indolinylcarboximidamide•HCl (Formula I: hydrochloride salt of R=2-methylphenyl, $R^1$=H, m=n=0)

Light gray powder; purity: 98.6% (HPLC); mp: 225–226° C.; TLC ($CHCl_3$:MeOH; 10:1): $R_f$=0.36; $^1$H NMR ($CD_3OD$): 7.46–7.13 (m, 8H, Ar—H), 4.23–4.17 (m, 2H, J=8.10, $CH_2$), 3.29–3.23 (t, J=8.10, $CH_2$; Anal. Calcd. for $C_{16}H_{17}N_3Cl$•HCl (287.79): C: 66.78, H: 6.30, N: 14.60; Found: C: 67.00, H: 6.41, N: 14.77.

EXAMPLE 18

N-(3-tolyl)-1-indolinylcarboximidamide•HCl (Formula I: hydrochloride salt of R=3-methylphenyl, $R^1$=H, m=n=0)

Light gray powder; purity: 99.0% (HPLC); mp: 122–124° C.; TLC ($CHCl_3$:MeOH; 10:1): $R_f$=0.17; $^1$H NMR ($CD_3OD$): 7.39–7.09 (m, 8H, Ar—H), 4.22–4.17 (t, 2H, J=8.05, $CH_2$), 3.28–3.23 (t, J=8.10, $CH_2$); Anal. Calcd. for $C_{16}H_{17}N_3Cl$•HCl•0.2 ether (302.62): C: 66.68, H: 6.66, N: 13.89; Found: C: 66.90, H: 6.52, N: 13.71.

EXAMPLE 19

N-(2-chloro-5-ethylphenyl)-[(7-trifluoromethyl)-1,2,3,4-tetrahydroquinolinyl]carboximidamide•HCl (Formula II: R=2-chloro-5-ethylphenyl, $R^1$=H, $R^3$=7-trifluoromethyl, n=1, m=0)

White solid; mp: 220° C.; $^1$H NMR (300 MHz, $CD_3OD$): δ 7.78 (s, 1H, Ar—H), 7.41–7.44 (m, 3H, Ar—H) 7.17–7.20 (br s, 1H, Ar—H), 3.89–3.93 (t, J=6.5 Hz, 2H, N—$CH_2$), 2.88–2.92 (t, 2H, J=6.5 Hz, $CH_2$), 2.59–2.67 (q, 2H, J=7.5 Hz, $CH_2$), 2.09–2.19 (dt, 2H, J=7.5 Hz, $CH_2$), 1.19–1.24 (t, 3H, $CH_3$); MS (El): m/e 382 ($M^+$ for free base); Anal. Calcd. for $C_{19}H_{19}ClF_3N_3HCl$: C: 54.09, H: 4.87, N: 9.96; Found: C: 54.05, H: 5.01, N: 10.00.

EXAMPLE 20

N-(1-naphthyl)-[(7-trifluoromethyl-1,2,3,4-tetrahydroquinolinyl]carboximidamide•HCl (Formula II: R=1-naphthyl, $R^1$=H, $R^3$=7-trifluoromethyl, n=1, m=0)

White solid; mp: 215–220° C.; $^1$H NMR (300 MHz, $CD_3OD$): δ 7.90–8.02 (m, 3H, Ar—H), 7.80 (br s, 1H, Ar—H), 7.52–7.68 (m, 4H, Ar—H), 7.37–7.41 (m, 2H, Ar—H), 3.94–3.98 (t, J=6.5 Hz, 2H, N—$CH_2$), 2.87–2.92 (t, 2H, Ar$CH_2$), 2.13–2.22 (q, J=6.5 Hz, 2H, $CH_2$); MS (El): m/e 371 ($M^-$ for free base); Anal. Calcd. for $C_{21}H_{19}F_3N_3$•HCl: C: 61.99, H: 4.96, N: 10.32; Found: C: 61.65, H: 4.63, N: 10.02.

EXAMPLE 21

N-(1-naphthyl)-(1,2,3,4-tetrahydroquinolinyl) carboximidamide•HCl (Formula II: R=1-naphthyl, $R^1$=H, m=n=0)

White solid; mp: 244° C.; $^1$H NMR (300 MHz, $CD_3OD$): δ 7.92–8.03 (m, 3H, Ar—H), 7.49–7.68 (m, 5H, Ar—H), 7.12–7.27 (m, 3H, Ar—H), 3.89–3.93 (t, J=6.5 Hz, 2H, N—CH), 2.84–2.88 (t, J=6.5 Hz, 2H, Ar—CH$_2$), 2.11–2.19 (q, J=6.5 Hz, 2H, CH$_2$); MS (EI): m/e 302 (M$^-$ for free base); Anal. Calcd. for C$_{20}$H$_{19}$N$_3$•HCl: C: 71.10, H: 5.97, N: 12.43; Found: C: 70.83, H: 5.82, N: 12.32.

EXAMPLE 22

N-(3-biphenyl)-1-(benz[cd]indolinyl) carboximidamide•HCl (Formula IV: hydrochloride salt of R=3-biphenyl, R$^1$=H, m=n=0)

Light gray solid; purity: 98.9% (HPLC); mp: 222–224° C.; TLC (CH$_2$Cl$_2$:MeOH; 11:1): R$_f$=0.58; $^1$H NMR (CD$_3$OD): 7.78–7.30 (m, 15H, Ar—H), 5.60 (s, CH$_2$); Anal. Calcd. for C$_{24}$H$_{19}$N$_3$•HCl•1.3H$_2$O: C: 70.42, H: 5.57, N: 10.26; Found: C: 70.70, H: 5.22, N: 9.96.

EXAMPLE 23

N-(2-tolyl)-1-(benz[cd]indolinyl) carboximidamide•HCl (Formula IV: hydrochloride salt of R=2-methylphenyl, R$^1$=H, m=n=0)

Light gray powder; purity: 99.0% (HPLC); mp: 132–134° C.; TLC (CH$_2$Cl$_2$:MeOH; 11:1): R$_f$=0.58; $^1$H NMR (CD$_3$OD): 7.78–7.37 (m, 10H, Ar—H), 5.58 (s, 2H, CH$_2$), 2.41 (s, 3H, CH$_3$).

EXAMPLE 24

N-(2,3-dimethylphenyl)-1-benz[cd] indolinylcarboximidamide•HCl (Formula IV: hydrochloride salt of R=2,3-dimethylphenyl, R$^1$=H, m=n=0)

Gray powder; purity: 97.6% (HPLC); mp: 236–238° C.; TLC (CHCl$_3$:MeOH; 10:1): R$_f$=0.27; $^1$H NMR (CD$_3$OD): 7.79–7.23 (m, 9H, Ar—H), 5.58 (s, 2H, CH$_2$), 2.40 (s, 3H, CH$_3$), 2.31 (s, 3H, CH$_3$); Anal. Calcd. for C$_{20}$H$_{19}$N$_3$•HCl (338.84): C: 71.10, H: 5.97, N: 12.44; Found: C: 71.16, H: 5.94, N: 12.22.

EXAMPLE 25

N-(2,5-dimethylphenyl)-1-benz[cd] indolinylcarboximidamide•HCl (Formula IV: hydrochloride salt of R=2,5-dimethylphenyl, R$^1$=H, m=n=0)

White solid; purity: 97.4% (HPLC); mp: 132–134° C.; TLC (CHCl$_3$:MeOH; 10:1): R$_f$=0.28; $^1$H NMR (CD$_3$OD): 7.76–7.21 (m, 9H, Ar—H), 5.57 (s, 2H, CH$_2$), 2.37 (s, 3H, CH$_3$), 2.35 (s, 3H, CH$_3$); Anal. Calcd. for C$_{20}$H$_{19}$N$_3$•HCl•0.4H$_2$O (345.06): C: 69.62, H: 6.08, N: 12.18; Found: C: 69.66, H: 5.70, N: 11.85.

EXAMPLE 26

N-(1-naphthyl)-1-benz[cd] indolinylcarboximidamide•HCl (Formula IV: hydrochloride salt of R=1-naphthyl, R$^1$=H, m=n=0)

Light gray solid; purity: 98% (HPLC); mp: 250–251° C.; R$_f$=0.43 chloroform/methanol 20/1); $^1$H NMR (CD$_3$OD): 8.10–7.40 (m, 13H, Ar—H), 5.68 (s, 2H, ArCH$_2$); HRMS: 323.1419 (cal: 323.1422 for C$_{22}$H$_{17}$N$_3$).

EXAMPLE 27

N-(3-ethylphenyl)-1-benz[cd] indolinylcarboximidamide•mesylate (Formula IV: mesylate salt of R=3-ethylphenyl, R$^1$=H, m=n=0)

Light gray solid; purity: 98% (HPLC); mp: 158–159° C.; R$_f$=0.38 (chloroform/methanol 10/1); $^1$H NMR (CD$_3$OD): 7.76–7.25 (m, 1OH, Ar—H), 5.56 (s, 2H, ArCH$_2$), 2.68–2.74 (m, 5H, CH$_2$ +CH$_3$SO$_3$H), 1.26 (t, 3H, CH$_3$, J=7.45 Hz); Anal. Calcd. for C$_{20}$H$_{19}$N$_3$•CH$_3$SO$_3$H: C: 63.46, H: 5.83, N: 10.57; Found: C: 63.30, H: 5.74, N: 10.39.

EXAMPLE 28

N-(naphth-1-yl)-1-(6-hydro) phenanthridinylcarboximidamide•HCl (Formula V: hydrochloride salt of R=1-naphthyl, R$^1$=H, m=n=0)

White solid; purity: 93.7% (HPLC); mp: 234–236° C.; R$_f$=0.38 (chloroform/methanol 10/1); $^1$H NMR (CD$_3$OD): d ppm 7.92–7.32 (m, 15H, Ar—H), 4.97 (s, 2H, ArCH$_2$); Anal. Calcd. for C$_{24}$H$_{19}$N$_3$•HCl: C: 74.70, H: 5.22, N: 10.88; Found: C: 74.86, H: 5.40, N: 10.82.

EXAMPLE 29

N-(2-naphthyl)-1-indolinyl- carboximidamide•hydrochloride (Formula I: hydrochloride salt of R=2-naphthyl, R$^1$=H,m=n=0)

White plate; purity: 99.6% (HPLC); mp: 256–258° C.; TLC (CH$_2$Cl$_2$:MeOH; 10:1): R$_f$=0.19; $^1$H NM (CD$_3$OD): 8.00–7.97 (d, 1H, J=8.8 Hz, Ar—H), 7.92–7.81 (m,3H, Ar—H), 7.55–7.36 (m, 5H, Ar—H), 7.24–7.12 (m, 2H, Ar—H), 4.27–4.22 (t, 2H, J=8.1 Hz, CH$_2$), 3.30–3.25 (t, 2H, J=8.1 Hz, CH$_2$). Anal. Calcd. for C$_{19}$H$_{17}$N$_3$•HCl (323.83): C, 70.47, H, 5.60, N, 12.98; Found: C, 70.26, H, 5.76, N, 12.76.

EXAMPLE 30

N-(3-biphenyl)-1-indolinyl-carboximidamide (Formula I: R=3-biphenyl, R$^1$=H, m=n=0)

White powder; purity: 97.1% (HPLC); mp: 148–150°; TLC (CH$_2$Cl$_2$: MeOH; 0:1): R$_f$=0.18; $^1$H NMR (CD$_3$OD): 7.63–7.59 (m, 2H, Ar—H), 7.53–7.24 (m, 8H, Ar—H), 7.16–7.10 (m, 2H, Ar—H), 6.99–6.94 (m, 1H, Ar—H), 4.15–4.10 (t, 2H, J=8.2 Hz, CH$_2$), 3.20–3.15 (t, 2H, J=8.2 Hz, CH$_2$). Anal. Calcd. for C$_{21}$H$_{19}$N$_3$•0.2EtOAc (331.03): C, 79.10, H, 6.27, N, 12.69; Found: C, 78.92, H, 6.02, N, 12.96.

EXAMPLE 31

N-(5-methoxynaphthyl)-1-indolinyl- carboximidmide•hydrochloride (Formula I: HCl salt of R=5-methoxynaphthyl, R$^1$=H,m=n=0)

White solid; purity: 97.87% (HPLC); TLC (CHCl$_3$: MeOH; 10:1): R$_f$=0.15; mp: 236–239° C.; $^1$H NMR (CD$_3$OD): 8.38–8.34 (d, 1H, J=7.3 Hz, Ar—H), 7.59–7.50 (m, 5H, Ar—H), 7.40–7.38 (d, 1H, J=6.8 Hz, Ar—H), 7.29–7.24 (td, 1H, J=8,1.4 Hz. Ar—H), 7.17–7.11 (td, 1H, J=7.4,1.0 Hz, Ar—H), 7.06–7.03 (dd, 1H, J=6.4,1.3 Hz, Ar—H), 4.30–4.25 (t, 2H, J=8.0 Hz, CH$_2$), 4.04 (s, 3H, OCH$_3$), 3.34–3.29 (t, 2H, J=8.0 Hz, CH$_2$). Annal. Calcd. for C$_{20}$H$_{19}$N$_3$O•HCl (353.86): C, 67.89, H, 5.70, N, 11.88; Found: C, 67.65, H, 5.61, N, 11.63.

EXAMPLE 32

N-(2-methylsulfinylphenyl)-1-indolinyl- carboximidamide•hydrochloride (Formula I: HCl salt of R=2-(CH$_3$SO)phenyl, R$^1$=H, m=n=0)

Light yellow powder; purity: 99.6% (HPLC); TLC (CHCl$_3$: MeOH; 10:1): R$_f$=0.5; $^1$H NMR (CD$_3$OD):

8.01–7.98 (dd, I1, J=2.7,7.7 Hz, Ar—H), 7.76–7.67 (m, 2H, Ar—H), 7.57–7.54 (m, 1H, Ar—H), 7.48–7.45 (d, 1H, J=7.7 Hz, Ar—H), 7.41–7.38 (d, 1H, J=6.6 Hz, Ar—H), 7.32–7.26 (t, 3H, J=8.2 Hz, Ar—H), 7.19–7.14 (m, 1H, Ar—H), 4.27–4.19 (m, 2H, $CH_2$), 3.33–3.27 (t, 2H, J=8.4 Hz, $CH_2$), 2.92 (s, 3H, $CH_3$).

EXAMPLE 33

N-(1-naphthyl)-(6-methyl-1,2,3,4-tetrahydroquinolinyl)carboximidamide hydrochloride (Formula II: HCl salt of R=1-naphthyl, $R^1$=H, X=$CH_2$, $R^3$=$CH_3$, n=1, m=0)

Light purple solid: mp 205–206° C.; $R_f$=0.364 (9:2 $CHCl_3$/MeOH); $^1$H NMR (300 MHz, $CD_3OD$) δ 7.92–8.0 (m, 3H, Ar—H), 7.51–7.68 (m, 4H, Ar—H), 7.37–7.40 (d, 1H, J=8.25 Hz, Ar—H), 7.02–7.08 (m, 2H, Ar—H), 3.87–3.91 (t, 2H, J=12.94 Hz, $CH_2$), 2.80–2.84 (t, 2H, J=12.91 Hz, $CH_2$), 2.29 (s, 3H, $CH_3$), 2.11–2.17 (m, 2H, $CH_2$). MS(Cl): m/e 316 (M+ for free base). Anal. Calcd. for $C_{21}H_{21}N_3$•HCl: C, 71.68, H, 6.30, N, 11.94. Found: C, 71.73, H, 6.51, N, 12.07.

EXAMPLE 34

N-(1-naphthyl)-N'-(2,3-dihydro-[1,4]-benzothiazinyl)carboximidamide hydrochloride (Formula II: HCl salt of R=1-naphthyl, $R^1$=H, X=S, m=n=0)

White solid: mp 245–246° C.; $R_f$=0.13 (10:1 $CHCl_3$/MeOH); $^1$H NMR (300 MHz, $CD_3OD$) δ 7.92–8.20 (m, 3H, Ar—H), 7.48–7.71 (m, 5H, Ar—H), 7.28–7.35 (m, 1H, Ar—H), 7.12–7.20 (m, 2H, Ar—H), 4.16–4.22 (m, 2H, $CH_2$), 3.40–3.47 (m, 2H, $CH_2$). MS(Cl): m/e 320 (M+ for free base). Anal. Calcd. for $C_{19}H_{17}N_3S$•HCl: c, 64.12, H, 5.10, N, 11.81. Found: C, 64.28, H, 5.20, N, 11.69.

EXAMPLE 35

N-(2,5-dibromophenyl)-(7-trifluoromethyl-1,2,3,4-tetrahydroquinolinyl)carboximidamide hydrochloride (Formula II: HCl salt of R=2,5-dibromophenyl, $R^1$=H, X=$CH_2$, $R^3$=$CF_3$, n=1, m=0)

Cream colored solid: mp 201–202° C.; $R_f$=0.354 (Eth. Ac.); $^1$H NMR (300 MHz, $CD_3OD$) δ 7.79 (s, 1H, Ar—H), 7.45–7.48 (m, 1H, Ar—H), 7.25–7.28 (d, 1H, J=7.97 Hz, Ar—H), 7.12–7.15 (m, 2H, Ar—H), 7.03–7.07 (m, 1H, Ar—H), 3.78–3.82 (t, 2H, J=11.96 Hz, $CH_2$), 2.84–2.89 (t, 2H, J=13.19 Hz, $CH_2$, 2.01–2.08 (m, 2H, $CH_2$). MS(Cl): m/e 478 (M+ for free base). Anal. Calcd. for $C_{17}H_{14}Br_2F_3N_3$•HCl: C, 39.76, H, 2.94, N, 8.18. Found: C, 39.57, H, 2.96, N, 7.98.

EXAMPLE 36

N-(2,3-difluorophenyl)-(1,2,3,4-tetrahydroquinolinyl)carboximidamnide hydrochloride (Formula II: HCl salt of R=2,3-fluorophenyl, $R^1$=H, X=$CH_2$, m=n=0)

White solid: mp 194–195° C.; $R_f$=0.135 (10:2 $CHCl_3$/MeOH); $^1$H NMR (300 MHz, $CD_3OD$) δ 7.34–7.37 (m, 1H, Ar—H), 7.12–7.27 (m, 6H, Ar—H), 3.83–3.87 (t, 2H, J=13.0 Hz, $CH_2$), 2.82–2.86 (t, 2H, J=13.19 Hz, $CH_2$), 2.06–2.15 (m, 2H, $CH_2$). MS(Cl): m/e 288 (M+ for free base). Anal. Calcd. for $C_{16}H_{15}F_2N_3$•HCl: c, 59.36, H, 4.98, N, 12.98. Found: C, 59.44, H, 4.97, N, 12.74.

EXAMPLE 37

N-(2-trfluoromethoxyphenyl)-(1,2,3,4-tetrahydroquinolinyl)carboximiide hydrochloride (Formula II: HCl salt of R=2-trifluromethoxyphenyl, $R^1$=H, X=$CH_2$, m=n=0)

White solid: mp 80–82° C.; $R_f$=0.115 (10:1 $CHCl_3$/MeOH); $^1$H NMR (300MHz, $CD_3OD$) δ 7.46–7.52 (t, 1H, J=16.42 Hz, Ar—H), 7.15–7.35 (m, 7H, Ar—H), 3.82–3.86 (t, 2H, J=12.98 Hz, $CH_2$), 2.82–2.86 (t, 2H, J=12.91 Hz, $CH_2$), 2.11–2.17 (m, 2H, $CH_2$). MS(Cl): m/e 336 (M$^+$ for free base). Anal. Calcd. for $C_{17}H_{16}F_3N_3O$•HCl: C, 54.92, H, 4.61, N, 11.30. Found: C, 55.10, H, 4.78, N, 11.44.

EXAMPLE 38

N-(2-biphenyl)-1-benz[cd]indolinyl-carboximidamide•hydrochloride (Formula IV: HCl salt of R=2-biphenyl, $R^1$=H, m=n=0)

Light grey powder; purity: 94.0% (HPLC); TLC ($CHCl_3$:MeOH; 10:1): $R_f$=0.25; mp: 143–145° C.; $^1$H NMR ($CD_3OD$): 7.73–7.70 (d, 1H, J=8.2 Hz, Ar—H), 7.61–7.32 (m, 13H, Ar—H), 7.08–7.06 (d, 1H, J=7.1 Hz, Ar—H), 5.19 (s, 2H, $CH_2$). Anal. Calcd. for $C_{24}H_{19}N_3$•HCl (385.89): c, 74.70, H, 5.22, N, 10.89; Found: C, 74.60, H, 5.40, N, 10.61.

EXAMPLE 39

N-(3.5-dichlorophenyl)-1-tetrahydrobenz[cd] indolinyl-carboximidamide•hydrochloride (Formula VII: HCl salt of R=3,5-dichlorophenyl, $R^1$=H, m=n=0)

White solid; purity: 98.7% (HPLC); TLC ($CHCl_3$:MeOH; 10:1): $R_f$=0.28; $^1$H NMR ($CD_3OD$): 7.39–7.35 (m, 3H, Ar—H), 7.19–7.14 (t, 1H, J=7.3 Hz, Ar—H), 7.11–7.08 (d, 1H, J=7.4 Hz, Ar—H), 6.95–6.93 (d, 1H, J=6.9HZ, Ar—H), 4.44–4.38 (dd, 1H, J=8.1,9.9 Hz, NCH), 3.44–3.40 (dd, 1H, J=8.1,9.9 Hz, NCH), 2.94–2.85 (m, 1H, CH), 2.75–2.69 (m, 1H, CH), 2.27–2.12 (m, 2H, $CH_2$), 1.86–1.80 (m, 1H, CH), 1.41–1.29 (m, 1H, CH). Calcd. for $C_{18}H_{17}N_3Cl_2$•HCl (382.73): C, 56.49, H, 4.74, N, 11.98, Cl, 27.79; Found: C, 56.44, H, 5.00, N, 10.99, Cl, 27.61.

EXAMPLE 40

N-(2,5-dibromophenyl)-(2,3,4,5-tetrahydro-[1,5]-benzothiazin-5-yl)carboximidamide hydrochloride (Formula VI: HCl salt of R=2,5-dibromophenyl, $R^1$=H, X=S, m=n=0)

Whitish solid: mp 216–217° C.; $^1$H NMR (300 MHz, $CD_3OD$) δ 7.4–7.8 (m, 7H, Ar—H), 4.3—4.65 (brs, 1H, $CH_2$), 3.2–3.4 (brs, 1H, $CH_2$), 2.7–3.1 (m, 2H, $CH_2$), 2.1–2.4 (m, 2H, $CH_2$). MS(Cl): m/e 442 (M$^+$+H for free base). Anal. Calcd. for $C_{16}H_{15}Br_2N_3S$•HCl: C, 40.23, H, 3.38, N, 8.80; Found: C, 40.08, H, 3.10, N, 8.73.

EXAMPLE 41

Synthesis of 5,6,11,12-tetrahydrodibenz[b,f]azocincarboximidamide•hydrochloride

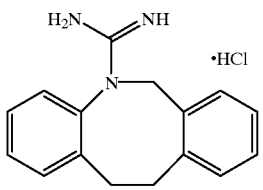

By method indicated above in Example 3, part 3 using 5,6,11,12-tetrahydrodibenz[b,f]azocine•HCl.

White solid: mp: 238–240° C., TLC (CHCl$_3$:MeOH; 10:1); R$_f$=0.25; $^1$H NMR (CD$_3$OD) δ ppm 7.1 (m, Ar—H, 8H), 5.28 (d, CHN, 1H), 4.58 (d, CHN, 1H), 3.20 (m, CH$_2$, 1H), 3.0 (m, CH$_2$, 1H); Mass /CI—NH$_3$: MH$^+$252; Anal. Calcd. for C$_{16}$H$_{18}$N$_3$Cl•0.25H$_2$O: C, 65.75, H, 6.38, N, 14.38; Found: C, 65.55, H, 6.37, N, 14.94.

EXAMPLE 42

Synthesis of N-(4'-sec-burylphenyl)-1-(5,6,11,12-tetrahydrodibenz[b,f]azocin)-carboximidamide•hydrochloride Part A: Preparation of 5,6,11,12-tetrahydrodibenz[b,f]azocin-cyanamide By method indicated in Example 2, part 1 above using 5,6,11,12-tetrahydrodibenz[b,f]azocine.

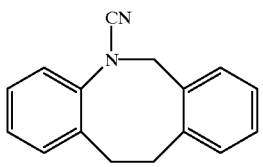

Part B: Preparation of N-(4'-sec-butylphenyl)-1-(5,6,11,12-tetrahydrodibenz[b,f]azocin)-carboximidamide•hydrochloride

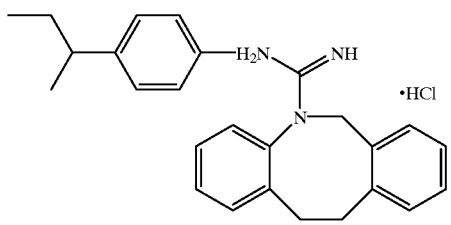

By method indicated in Example 2, part 2 above using 5,6,11,12-tetrahydrodibenz[b,f]azocin-cyanamide, sec-butylaniline and one equivalent of aluminum chloride.

Oil, TLC (CHCl$_3$:MeOH; 10:0.5); R$_f$=0.25; $^1$H NMR (CDCl$_3$) δ ppm 7.1 (m, Ar—H, 12H), 5.4 (br, CHN, 1H), 4.6 (br, CHN, 1H), 3.25 (br, CH$_2$, 2H), 3.0 (br, CH$_2$, 2H), 2.55 (m, CH, 1H), 1.60 (m, CH$_2$, 2H), 1.2 (d, CH$_3$CH$_2$, 3H), 0.8 (t, CH$_3$CH, 3H); Mass /CI—NH$_3$: MH$^+$384.

EXAMPLE 43

10,11-dihydro-[5H]-diben[b,f]azepinylcarboximidamide hydrochloride

White solid: mp 120–121° C.; $^1$H NMR (300 MHz, CD$_3$OD) δ 7.31–7.46 (m, 8H, Ar—H), 3.23–3.36 (brs, 2H, Ar—CH$_2$), 2.80–2.93 (brs, 1H, Ar—CH$_2$); MS(Cl): m/e 238 (M$^+$ for free base); Anal. Calcd. for C$_{15}$H$_{15}$N$_3$•HCl: C, 60.99, H, 6.28, N, 14.22; Found: C, 60.91, H, 6.17, N, 14.29.

EXAMPLE 44

N-(1-naphthyl)-dibenzo[b,f]azepinylcarboximidamide hydrochloride

White solid; mp 230° C.; $^1$H NMR (300 MHz, CD$_3$OD) δ 7.94–7.99 (m, 2H, Ar—H), 7.79–7.87 (m, 2H, Ar—H), 7.62–7.69 (m, 5H, Ar—H), 7.51–7.61 (m, 5H, Ar—H), 7.44–7.47 (m, 1H, Ar—H), 7.33–7.36 (brs, 2H, CH=CH); MS(Cl): m/e 262 (M$^+$+H for free base); Anal. Calcd. for C$_{25}$H$_{19}$N$_3$•HCl: C, 75.46, H, 5.07, N, 10.56; Found: C, 75.59, H, 5.03, N, 10.55.

EXAMPLE 45

N-(4-butoxyphenyl)-dibenzo[b,f]azepinylcarboximidarnide hydrochloride

White solid: mp 190–192° C.; R$_f$=0.269 (10:2 CHCl$_3$/MeOH); $^1$H NMR (300 MHz, CD$_3$OD) δ 7.49–7.73 (m, 8H, Ar—H), 7.19 (s, 2H, Ar—H), 7.07–7.10 (m, 2H, Ar—H), 6.92–6.95 (m, 2H, Ar—H), 3.93–3.97 (t, 2H, J=13 Hz, 2H, CH$_2$), 1.68–1.78 (m, 2H, CH$_2$), 1.40–1.52 (m, 2H, CH$_2$), 0.928–0.977 (t, 3H, J=14.71 Hz, CH$_3$); MS(Cl): m/e 384 (M$^+$ for free base); Anal. Calcd. for C$_{25}$H$_{25}$N$_3$O•CH$_3$SO$_3$H: C, 65.11, H, 6.09, N, 8.76; Found: C, 61.16, H, 6.45, N, 8.20.

EXAMPLE 46

N-(2-chloro-5-methylsulfinylphenyl)-1-(6-trifluoromethyl-1,2,3,4-tetrahydroquinolinyl) carboximidaimide hydrochloride (Formula II: HCl salt of R=2-chloro-5-methylsulfmylphenyl, R$^1$=H, X=CH$_2$, R$^3$=6-trifluoromethyl, n=1, m=0)

The title compound was prepared by oxidiation of the corresponding sulfide precursor (i.e. (N-(2-chloro-5-methylthiophenyl)-1-(6-trifluoromethyl-1,2,3,4-tetrahydroquinolinyl)-carboxitidamide) with 30% hydrogen peroxide in methanol at reflux for 24 hours, followed by column chrornatography over silica gel.

White solid: mp 188–190° C.; R$_f$=0.12 (10:1 CHCl$_3$/MeOH); $^1$H NMR (300 MHz, CD$_3$OD) δ 7.476–7.743 (m, 7H, Ar—H), 3.904–3.946 (t, J=6 Hz, 2H, CH), 2.799 (s, 3H, CH$_3$), 2.100–2.186 (m, 2H, CH$_2$); MS(Cl): m/e 417 (M+ for free base); Anal. Calcd. for C$_{18}$H$_{17}$ClF$_3$N$_3$OS•HCl: C, 47.80, H, 4.01, N, 9.29; Found: C, 47.86, H, 4.25, N, 9.16.

EXAMPLE 47

N-(1-naphthyl)-1-(2,3-dihydro-1-oxo-6-trifluoromethylbenzo[1,4]thiazin-4-yl) carboximaidamide mesylate (Formula II'': mesylate salt of R=1-naphthyl, R$^1$=H, X=S—(O)—R$^3$=6-trifluoromethyl, n=1, m=0)

The title compound was prepared by oxidiation of the corresponding sulfide precursor (i.e. N-(1-naphthyl)-1-(2,3-dihydro-6-trifluoromethylbenzo[1,4]thiazin-4-yl) carboximidamide) with sodium periodate in acetonitrile:water (1:1) at room temperature for 24 hours, then conversion to free base with 1N NaOH followed by column chromatography over silica gel and conversion to the mesylate salt with methane sulfonic acid.

White solid: mp 231–234° C.; R$_f$=0.45 (9:1 CHCl$_3$/MeOH); $^1$H NMR (300 MHz, CD$_3$OD) δ 7.96–8.03 (m, 3H, Ar—H), 7.58–7.63 (m, 1H, Ar—H), 7.40*14* 7.52 (m, 3H, Ar—H), 7.28–7.39 (d, J=6 Hz, 1H, Ar—H), 7.02–7.11 (d, J=6 Hz, 1H, Ar—H), 4.44–4.52 (brs, 1H, $CH_2$), 4.02–4.20 (brs, 1H, $CH_2$), 3.19–3.40 (brs, 1H, $CH_2$); MS(Cl): m/e 404 ($M^+$ for free base); Anal. Calcd. for $C_{20}H_{16}F_3N_3OS \cdot HCl$: C, 45.41, H, 4.76, N, 7.57; Found: C, 45.09, H, 4.40, N, 7.29.

EXAMPLE 48
In vivo Anticonvulsant activity in the DBA/2 mouse model (Mouse audiogenic assay)

The in vivo potency of compounds of the invention is exemplified by data summarized in the Table I below and obtained pursuant to the following protocol.

Compounds were tested for their effectiveness in preventing seizures in DBA/2 mice which have a unique sensitivity to auditory stimulation. Exposure to loud high-frequency sounds can trigger seizure activity in these animals. This sensitivity develops from postnatal day 12 and peaks around day 21 and slowly diminishes as the animals mature. The unusual response to auditory stimulation in this strain of mouse is believed to be due to a combination of early myelination (causing an unusually low excitatory threshold) and delayed development of inhibitory mechanisms.

Mice were injected intraperitoneally with the compound specified in Table I below or with vehicle control, 30 minutes prior to being placed in a bell jar and turning on the auditory stimulus (12 KHz sine wave at 110–120 db). Administered doses are specified in Table I as milligram of compound per kilogram bodyweight of mouse. The auditory stimulus was left on for 60 seconds and mice reactions were time and recorded. Percentage inhibition was determined with reference to vehicle controls. Results are shown in the Table I below. "FB" refers to free base.

TABLE I

| | | Audiogenic Response | | |
|---|---|---|---|---|
| Example No. | Compound Name | Dose (mg/kg) | % Inhib. | Salt |
| 2 | N-(1-naphthyl)-1-indolinylcarboximidamide | 2<br>10 | 82<br>100 | FB |
| 4 | N-(4-benzyloxyphenyl)-1-indolinylcarboximidamide | 20 | 32 | mesylate |
| 5 | N-(40-methoxynaphthyl)-1-indolinylcarboximidamide | 5<br>10<br>20 | 50<br>68<br>87 | mesylate |
| 6 | N-(3,4-dichlorophenyl)-1-indolinylcarboximidamide | 10<br>20 | 41<br>83 | FB |
| 7 | N-(5-acenaphthyl)-1-(5-methoxy)-indolinylcarboximidamide | 10 | 21 | FB |
| 8 | N-(5-acenaphthyl)-1-(5-bromo)-indolinylcarboximidamide | 20 | 11 | FB |
| 9 | N-(4-sec-butylphenyl)-1-indolinylcarboximidamide | 20 | 28 | mesylate |
| 11 | N-(2,3-dichlorophenyl)-1-indolinylcarboximidamide | 10 | 55 | HCl |
| 12 | N-(2,3-dimethylphenyl)-1-indolinylcarboximidamide | 10<br>5<br>2 | 88<br>67<br>23 | HCl |
| 13 | N-(5,6,7,8-tetrahydro-1-naphthyl)-1-indolinylcarboximidamide | 20<br>10 | 80<br>48 | HCl |
| 14 | N-(2-biphenyl)-1-indolinylcarboximidamide | 20 | 56 | HCl |
| 20 | N-(1-naphthyl)-[(7-trifluoromethyl-1,2,3,4-tetrahydroquinolinyl)carboximidamide] | 4 | 13 | HCl |
| 21 | N-(1-naphthyl)-1,2,3,4-tetrahydroquinolinyl)carboximidamide | 4<br>2<br>1 | 88<br>62<br>13 | HCl |
| 22 | N-(3-biphenyl)-N-(benz[cd]indolinyl)carboximidamide | 10 | 23 | HCl |
| 23 | N-(2-tolyl)-N-(benz[cd]indolinyl)carboximidamide | 4<br>2<br>1 | 95<br>61<br>53 | HCl |
| — | N-(1-naphthyl)-[6-methyl-1,2,3,4-tetrahydroquinolinyl)carboximidamide | 4 | 62 | HCl |
| — | N-(2-chloro-5-ethylphenyl)-[7-trifluoromethyl-1,2,3,4-tetrahydroquinolinyl)carboximidamide] | 20<br>10 | 91<br>44 | HCl |
| 25 | N-(1-naphthyl)-1-benz[cd]indolinylcarboximidamide | 10<br>5 | 76<br>59 | HCl |
| — | N-(1-naphthyl)-1,2,3,4-tetrahydroisoquinolinyl)carboximidamide | 20 | 41 | HCl |

This invention has been described in detail with reference to preferred embodiments thereof. However, it will be appreciated that those skilled in the art, upon consideration of this disclosure, may make modifications and improvements within the spirit and scope of the invention.

What is claimed is:
1. A compound of the following formula:

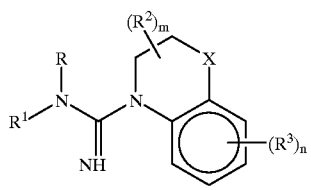

II wherein R and R¹ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted alkylsulfinyl or substituted or unsubstituted alkylsulfonyl, substituted or unsubstituted carbocyclic aryl, substituted or unsubstituted aralkyl, or a substituted or unsubstituted heteroaromatic or heteroalicyclic group having from 1 to 3 rings, 3 to 8 ring members in each ring and from 1 to 3 hetero atoms, with at least one of R and R¹ being other than hydrogen;

each R³ is independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl having at least about 6 ring carbon atoms;

X is —O—, —S—, or substituted or unsubstituted —N—;

n is 0, 1, 2, 3 or 4; and pharmaceutically acceptable salts thereof.

2. A compound of the following formula:

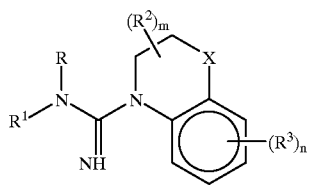

II wherein R and R¹ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted alkylsulfinyl or substituted or unsubstituted alkylsulfonyl, substituted or unsubstituted carbocyclic aryl, substituted or unsubstituted aralkyl, or a substituted or unsubstituted heteroaromatic or heteroalicyclic group having from 1 to 3 rings, 3 to 8 ring members in each ring and from 1 to 3 hetero atoms;

each R² and each R³ is independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl having at least about 6 ring carbon atoms;

X is sulfinyl or sulfonyl;

m and n are each independently 0,1,2,3 or 4; and pharmaceutically acceptable salts thereof.

3. A compound of the following formula:

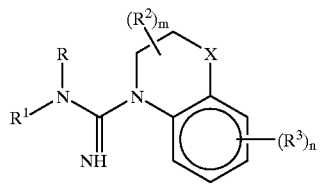

wherein R and R¹ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted alkylsulfinyl or substituted or unsubstituted alkylsulfonyl, substituted or unsubstituted carbocyclic aryl, substituted or unsubstituted aralkyl, or a substituted or unsubstituted heteroaromatic or heteroalicyclic group having from 1 to 3 rings, 3 to 8 ring members in each ring and from 1 to 3 hetero atoms;

each R² and each R³ is independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl having at least about 6 ring carbon atoms;

X is sulfmyl or sulfonyl;

m and n are each independently 0,1,2,3 or 4; or pharmaceutically acceptable salts thereof.

4. A compound of any one of claim 1 that is:
N-(1-naphthyl)-4-(2,3-dihydro-[1,4]-benzothiazinyl) carboximidamide;
N-(1-naphthyl)-4-(2,3-dihydro-[1,4]-benzoxazinyl) carboximidamide;
N-(2,5-dibromophenyl)-4-(2,3-dihydro-6-trifluoromethyl-[1,4]-benzothiazinyl) carboximidamide;
N-(2-fluoro-5-trifluoromethylphenyl)-4-(6-chloro-[1,4]-benzothiazinyl)-carboximidamide;
N-(2,5-dibromophenyl)-4-(6-chloro-[1,4]-benzothiazinyl)carboximidamide;
N-(1-naphthyl)-4-(6-chloro-2,3-dihydro-[1,4]-benzothiazinyl)carboximidamide;
N-(5-acenaphthyl)-4-(2,3-dihydro-[1,4]-benzothiazinyl) carboximidamide;
N-(2,3-difluorophenyl)-N-methyl-4-(2,3-dihydro-[1,4]-benzothiazinyl) carboximidamide;
N-(1-naphthyl)-4-(6-trifluoromethyl-2,3-dihydro-[1,4]-benzothiazinyl) carboximidamide;

N-(5,6,7,8-tetrahydro-1-naphthyl)-4-(2,3-dihydrobenzo-[1,4]-thiazinyl) carboximidamide;

N-(3-biphenyl)-4-(2,3-dihydrobenzo-[1,4]-thiazinyl) carboximidamide;

N-(2-naphthyl)-4-(2,3-dihydrobenzo-[1,4]-thiazinyl) carboximidamide;

N-(3,5-dichlorophenyl)-4-(2,3-dihydro-[1,4]-benzothiazinyl)carboximidamide; and

N-(2,3-difluorophenyl)-4-(2,3-dihydro-[1,4]-benzothiazinyl)carboximidamide; or or a pharmaceutically acceptable salt of said compounds.

5. A compound of claim 3 that is N-(2,5-dibromophenyl)-4-(2,3-dihydro-4-oxo-6-trifluoromethyl-[1,4]-benzothiazinyl)-carboximidamide;

N-(2,5-dibromophenyl)-4-(2,3-dihydro-1-dioxo-6-trifluoromethyl)-([1,4]-bezothiazinyl) carboximidarmide; or N-(1-naphthyl)-4-(2,3-dihydro-6-trifluoromethylbenzo[1,4]-1-oxo-thiazinyl)carboximidamide;

or a pharmaceutically acceptable salt of said compounds.

6. A compound of any one of claims 1, 2 or 3 wherein R is substituted or unsubstituted carbocyclic aryl, substituted or unsubstituted aralkyl, or a substituted or unsubstituted heteroaromatic or heteroalicyclic group.

7. A compound of any one of claims 1, 2 or 3 wherein R is substituted or substituted carbocyclic aryl.

8. A compound of any one of claims 1, 2 or 3 wherein R is substituted or urisubstituted phenyl or naphthyl.

9. A compound of any one claims 1, 2 or 3 wherein R is phenyl or naphthyl substituted at one or more ring positions by halogen hydroxyl, azido, alkyl, alkenyl, alkynyl, alkoxy, alkylthio, alkylsulfinyl, alkylsulfonyl, aminoalkyl, carbocyclic aryl, or aralkyl.

10. A compound of any one of claims 1, 2 or 3 wherein $R^1$ is hydrogen or substituted or unsubstituted alkyl, substituted or unsubstitued alkenyl, substituted or unsubstituted alkynyl, substituted or unsubstituted alkoxy, substituted or unsubstituted alkylthio, substituted or unsubstituted aminoalkyl, substituted or unsubstituted alkylsulfinyl, or substituted or unsubstituted alkylsulfonyl.

11. A compound of any one of claims 1, 2 or 3 wherein $R^1$ is hydrogen or substituted or unsubstituted alkyl.

12. A compound of any of the claims 1, 2 or 3 that is optically active.

13. A compound of claim 2 or 3 where the compound contains an optically active —S(O)— group.

14. A pharmaceutical composition comprising a pharmaceutically acceptable carrier and a compound of any one of claims 1, 2, 3, 5 or 6.

15. A method of treating a neurodegenerative disease comprising administering to a mammal suffering from or susceptible to said disease a therapeutically effective amount of a compound of the following formula:

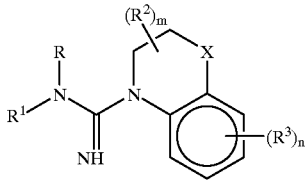

II wherein R and $R^1$ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted alkylsulfinyl or substituted or unsubstituted alkylsulfonyl, substituted or unsubstituted carbocyclic aryl, substituted or unsubstituted aralkyl, or a substituted or unsubstituted heteroaromatic or heteroalicyclic group having from 1 to 3 rings, 3 to 8 ring members in each ring and from 1 to 3 hetero atoms;

each $R^2$ and each $R^3$ are each independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl having at least about 6 ring carbon atoms;

X is —O—, —S—, or substituted or unsubstituted —N—;

m and n are each independently 0,1,2,3 or 4; and pharmaceutically acceptable salts thereof.

16. A method of treating a neurodegenerative disease comprising administering to a mammal suffering from said disease a therapeutically effective amount of a compound of the following formula:

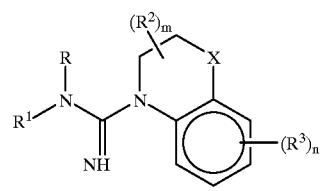

wherein R and $R^1$ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted alkylsulfinyl or substituted or unsubstituted alkylsulfonyl, substituted or unsubstituted carbocyclic aryl, substituted or unsubstituted aralkyl, or a substituted or unsubstituted heteroaromatic or heteroalicyclic group having from 1 to 3 rings, 3 to 8 ring members in each ring and from 1 to 3 hetero atoms;

each $R^2$ and each $R^3$ are each independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl having at least about 6 ring carbon atoms;

X is sulfinyl or sulfonyl;

m and n are each independently 0,1,2,3 or 4; and pharmaceutically acceptable salts thereof.

17. A method of treating Alzheimer's disease, Parkinson's disease, Huntington's disease, Amyotrophic Lateral Sclerosis, Down's Syndrome or Korsakoff's disease, Cerebral Palsy, or epilepsy, comprising administering to a mammal suffering from or susceptible to said disease a therapeutically effective amount of a compound of the formula:

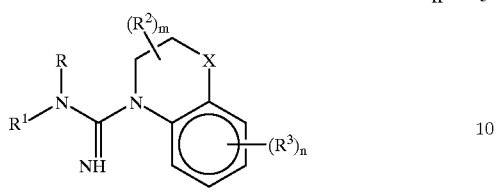

II wherein R and R¹ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted alkylsulfinyl or substituted or unsubstituted alkylsulfonyl, substituted or unsubstituted carbocyclic aryl, substituted or unsubstituted aralkyl, or a substituted or unsubstituted heteroaromatic or heteroalicyclic group having from 1 to 3 rings, 3 to 8 ring members in each ring and from 1 to 3 hetero atoms;

each R² and each R³ are each independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl having at least about 6 ring carbon atoms;

X is —O—, —S—, or substituted or unsubstituted —N—;

m and n are each independently 0,1,2,3 or 4; and pharmaceutically acceptable salts thereof.

18. A method of treating Alzheimer's disease, Parkinson's disease, Huntington's disease, Amyotrophic Lateral Sclerosis, Down's Syndrome or Korsakoff's disease, Cerebral Palsy, or epilepsy, comprising administering to a mammal suffering from said disease a therapeutically effective amount of a compound of the formula:

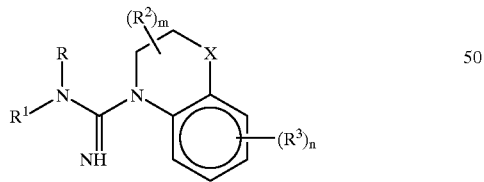

wherein R and R¹ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted alkylsulfinyl or substituted or unsubstituted alkylsulfonyl, substituted or unsubstituted carbocyclic aryl, substituted or unsubstituted aralkyl, or a substituted or unsubstituted heteroaromatic or heteroalicyclic group having from 1 to 3 rings, 3 to 8 ring members in each ring and from 1 to 3 hetero atoms;

each R² and each R³ are each independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl having at least about 6 ring carbon atoms;

X is sulfnyl or sulfonyl;

m and n are each independently 0,1,2,3 or 4; and pharmaceutically acceptable salts thereof.

19. A method of treating nerve cell death or degeneration comprising administering to a mammal suffering from or susceptible to nerve cell death or degeneration a therapeutically effective amount of a compound of the formula:

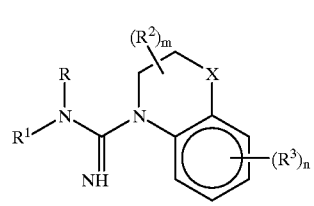

II wherein R and R¹ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted alkylsulfinyl or substituted or unsubstituted alkylsulfonyl, substituted or unsubstituted carbocyclic aryl, substituted or unsubstituted aralkyl, or a substituted or unsubstituted heteroaromatic or heteroalicyclic group having from 1 to 3 rings, 3 to 8 ring members in each ring and from 1 to 3 hetero atoms;

each R² and each R³ are each independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl having at least about 6 ring carbon atoms;

X is —O—, —S—, or substituted or unsubstituted —N—;

m and n are each independently 0,1,2,3 or 4; and pharmaceutically acceptable salts thereof.

20. A method of treating or preventing nerve cell death or degeneration comprising administering to a mammal suffering from or susceptible to nerve cell death or degeneration a therapeutically effective amount of a compound of the formula:

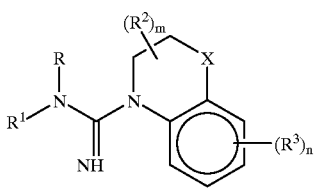

wherein R and R¹ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted alkylsulfinyl or substituted or unsubstituted alkylsulfonyl, substituted or unsubstituted carbocyclic aryl, substituted or unsubstituted aralkyl, or a substituted or unsubstituted heteroaromatic or heteroalicyclic group having from 1 to 3 rings, 3 to 8 ring members in each ring and from 1 to 3 hetero atoms;

each R² and each R³ are each independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl having at least about 6 ring carbon atoms;

X is sulfinyl or sulfonyl;

m and n are each independently 0,1,2,3 or 4; and pharmaceutically acceptable salts thereof.

21. A method of claim 19 or 20 wherein the nerve cell death or degeneration is caused by hypoxia, hypoglycemia, brain or spinal cord ischemia, retinal ischemia or brain or spinal cord trauma.

22. A method of treating a mammal suffering from or susceptible to stroke, heart attack or brain or spinal cord trauma comprising administering to a mammal suffering from or susceptible to stroke, heart attack or brain or spinal cord trauma a therapeutically effective amount of a compound of the formula:

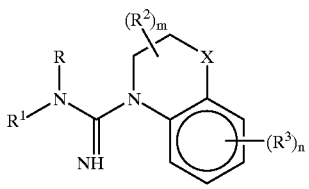

II wherein R and R¹ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted alkylsulfinyl or substituted or unsubstituted alkylsulfonyl, substituted or unsubstituted carbocyclic aryl, substituted or unsubstituted aralkyl, or a substituted or unsubstituted heteroaromatic or heteroalicyclic group having from 1 to 3 rings, 3 to 8 ring members in each ring and from 1 to 3 hetero atoms;

each R² and each R³ are each independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl having at least about 6 ring carbon atoms;

X is —O—, —S—, or substituted or unsubstituted —N—;

m and n are each independently 0,1,2,3 or 4; and pharmaceutically acceptable salts thereof.

23. A method of treating a mammal suffering from or susceptible to stroke, heart attack or brain or spinal cord trauma comprising administering to a mammal suffering from or susceptible to stroke, heart attack or brain or spinal cord trauma a therapeutically effective amount of a compound of the formula:

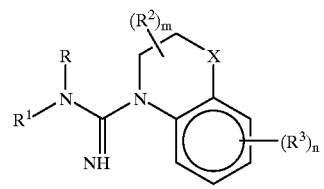

wherein R and R¹ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted alkylsulfinyl or substituted or unsubstituted alkylsulfonyl, substituted or unsubstituted carbocyclic aryl, substituted or unsubstituted aralkyl, or a substituted or unsubstituted heteroaromatic or heteroalicyclic group having from 1 to 3 rings, 3 to 8 ring members in each ring and from 1 to 3 hetero atoms;

each R² and each R³ are each independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl having at least about 6 ring carbon atoms;

X is sulfinyl or sulfonyl;

m and n are each independently 0,1,2,3 or 4; and pharmaceutically acceptable salts thereof.

24. A method of treating a mammal suffering from or susceptible to neuropathic pain, migraines, shingles, emesis, narcotic withdrawal symptoms or age comprising administering to the mammal a therapeutically effective amount of a compound of the formula:

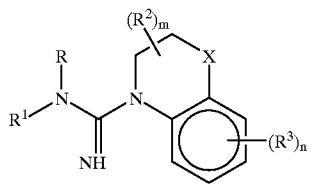

wherein R and R¹ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted alkylsulfinyl or substituted or unsubstituted alkylsulfonyl, substituted or unsubstituted carbocyclic aryl, substituted or unsubstituted aralkyl, or a substituted or unsubstituted heteroaromatic or heteroalicyclic group having from 1 to 3 rings, 3 to 8 ring members in each ring and from 1 to 3 hetero atoms;

each $R^2$ and each $R^3$ are each independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl having at least about 6 ring carbon atoms;

X is —O—, —S—, or substituted or unsubstituted —N—;

m and n are each independently 0,1,2,3 or 4; and pharmaceutically acceptable salts thereof.

25. A method of treating a mammal suffering from or susceptible to neuropathic pain, migraines, shingles, emesis, narcotic withdrawal symptoms or age-dependent dementia, comprising administering to the mammal a therapeutically effective amount of a compound of the formula:

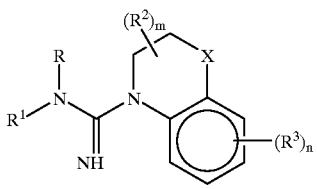

wherein R and R¹ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted alkylsulfinyl or substituted or unsubstituted alkylsulfonyl, substituted or unsubstituted carbocyclic aryl, substituted or unsubstituted aralkyl, or a substituted or unsubstituted heteroaromatic or heteroalicyclic group having from 1 to 3 rings, 3 to 8 ring members in each ring and from 1 to 3 hetero atoms;

each $R^2$ and each $R^3$ are each independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl having at least about 6 ring carbon atoms;

X is sulfnyl or sulfonyl;

m and n are each independently 0,1,2,3 or 4; and pharmaceutically acceptable salts thereof.

26. A method of treating a mammal suffering from or susceptible to decreased blood flow or nutrient supply to retinal tissue or optic nerve, or retinal ischemia or trauma, or optic nerve injury, comprising administering to the mammal a therapeutically effective amount of a compound of the formula:

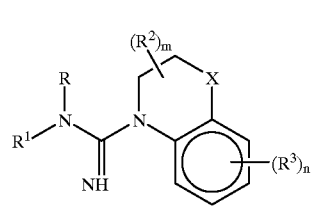

wherein R and R¹ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted alkylsulfinyl or substituted or unsubstituted alkylsulfonyl, substituted or unsubstituted carbocyclic aryl, substituted or unsubstituted aralkyl, or a substituted or unsubstituted heteroaromatic or heteroalicyclic group having from 1 to 3 rings, 3 to 8 ring members in each ring and from 1 to 3 hetero atoms;

each $R^2$ and each $R^3$ are each independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl having at least about 6 ring carbon atoms;

X is —O—, —S—, or substituted or unsubstituted —N—;

m and n are each independently 0,1,2,3 or 4; and pharmaceutically acceptable salts thereof.

27. A method of treating a mammal suffering from or susceptible to decreased blood flow or nutrient supply to retinal tissue or optic nerve, or retinal ischemia or trauma, or optic nerve injury, comprising administering to the mammal a therapeutically effective amount of a compound of the formula:

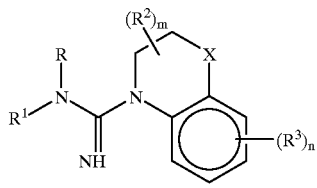

wherein R and $R^1$ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted alkylsulfinyl or substituted or unsubstituted alkylsulfonyl, substituted or unsubstituted carbocyclic aryl, substituted or unsubstituted aralkyl, or a substituted or unsubstituted heteroaromatic or heteroalicyclic group having from 1 to 3 rings, 3 to 8 ring members in each ring and from 1 to 3 hetero atoms;

each $R^2$ and each $R^3$ are each independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl having at least about 6 ring carbon atoms;

X is sulfinyl or sulfonyl;

m and n are each independently 0,1,2,3 or 4; and pharmaceutically acceptable salts thereof.

28. A method of treating a mammal suffering from or susceptible to post-surgical neurological deficits or neurological deficits associated with cardiac arrest, comprising administering to the mammal a therapeutically effective amount of a compound of the formula:

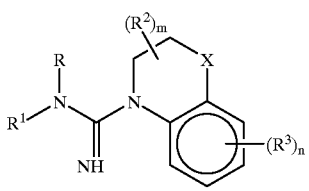

wherein R and $R^1$ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted alkylsulfinyl or substituted or unsubstituted alkylsulfonyl, substituted or unsubstituted carbocyclic aryl, substituted or unsubstituted aralkyl, or a substituted or unsubstituted heteroaromatic or heteroalicyclic group having from 1 to 3 rings, 3 to 8 ring members in each ring and from 1 to 3 hetero atoms;

each $R^2$ and each $R^3$ are each independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl having at least about 6 ring carbon atoms;

X is —O—, —S—, or substituted or unsubstituted —N—;

m and n are each independently 0,1,2,3 or 4; and pharmaceutically acceptable salts thereof.

29. A method of treating a mammal suffering from or susceptible to post-surgical neurological deficits or neurological deficits associated with cardiac arrest, comprising administering to the mammal a therapeutically effective amount of a compound of the formula:

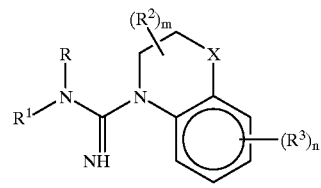

wherein R and $R^1$ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted alkylsulfinyl or substituted or unsubstituted alkylsulfonyl, substituted or unsubstituted carbocyclic aryl, substituted or unsubstituted aralkyl, or a substituted or unsubstituted heteroaromatic or heteroalicyclic group having from 1 to 3 rings, 3 to 8 ring members in each ring and from 1 to 3 hetero atoms;

each $R^2$ and each $R^3$ are each independently hydrogen, halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl having at least about 6 ring carbon atoms;

X is sulfinyl or sulfonyl;

m and n are each independently 0,1,2,3 or 4; and pharmaceutically acceptable salts thereof.

30. A method of any one of claims 15, 17, 19, 22, 24, 26, and 28 wherein the compound is:

N-(1-naphthyl)-4-(2,3-dihydro-[1,4]-benzothiazinyl) carboximidamide;

N-(1-naphthyl)-4-(2,3-dihydro-[1,4]-benzoxazinyl) carboximidamide;

N-(2,5-dibromophenyl)-4-(2,3-dihydro-6-trifluoromethyl-[1,4]-benzothiazinyl) carboximidamide;

N-(2-fluoro-5-trifluoromethylphenyl)-4-(6-chloro-[1,4]-benzothiazinyl)-carboximidamide;

N-(2,5-dibromophenyl)-4-(6-chloro-[1,4]-benzothiazinyl)carboximidamide;

N-(1-naphthyl)-4-(6-chloro-2,3-dihydro-[1,4]-benzothiazinyl)carboximidamide;

N-(5-acenaphthyl)-4-(2,3-dihydro-[1,4]-benzothiazinyl) carboximidamide;

N-(2,3-difluorophenyl)-N-methyl-4-(2,3-dihydro-[1,4]-benzothiazinyl) carboximidamide;

N-(1-naphthyl)-4-(6-trifluoromethyl-2,3-dihydro-[1,4]-benzothiazinyl) carboximidamide;

N-(5,6,7,8-tetrahydro-1-naphthyl)-4-(2,3-dihydrobenzo-[1,4]-thiazinyl) carboximidamide;

N-(3-biphenyl)-4-(2,3-dihydrobenzo-[1,4]-thiazinyl) carboximidamide;

N-(2-naphthyl)-4-(2,3-dihydrobenzo-[1,4]-thiazinyl) carboximidamide;

N-(3,5-dichlorophenyl)-4-(2,3-dihydro-[1,4]-benzothiazinyl)carboximidamide; and

N-(2,3-difluoropbenyl)-4-(2,3-dihydro-[1,4]-benzothiazinyl)carboximidamide; or a pharmaceutically acceptable salt of said compounds.

31. A method of any one of claims 16, 18, 20, 23, 25, 27 and 29 wherein the compound is N-(2,5-dibromophenyl)-4-(2,3-dihydro-4-oxo-6-trifluoromethyl-[1,4]-benzothiazinyl)-carboximidamide;

N-(2,5-dibromophenyl)-4-(2,3-dihydro-1-dioxo-6-trifluoromethyl)-([1,4]-benzothiazinyl) carboximidamide; or N-(1-naphthyl)-4-(2,3-dihydro-6-trifluoromethylbenzo[1,4]-1-oxo-thiazinyl)carboximidamide;

or a pharmaceutically acceptable salt of said compounds.

32. A method of any one of claims 15–20, or 22–29 wherein R is substituted or unsubstituted carbocyclic aryl, substituted or unsubstituted aralkyl, or a substituted or unsubstituted heteroaromatic or heteroalicyclic group.

33. A method of any one of claims 15–20 or 22–29 wherein R is substituted or unsubstituted carbocyclic aryl.

34. A method of any one claims 15–20 or 22–29 wherein R is substituted or unsubstituted phenyl or naphthyl.

35. A method of any one claims 15–20 or 22–29 wherein R is phenyl or naphthyl substituted at one or more ring positions by halogen, hydroxyl, azido, alkyl, alkenyl, alkynyl, alkoxy, alkylthio, alkylsulfinyl, alkylsulfonyl, aminoalkyl, carbocyclic aryl, or aralkyl.

36. A method of any one of claims 15–20 or 22–29 wherein R1 is hydrogen or substituted or unsubstituted alkyl.

37. A method of claim 21 wherein R is substituted or unsubstituted carbocyclic aryl, substituted or unsubstituted aralkyl, or a substituted or unsubstituted heteroaromatic or heteroalicyclic group.

38. A method of claim 21 wherein R is substituted or unsubstituted carbocyclic aryl.

39. A method of claim 21 wherein R is substituted or unsubstituted phenyl or naphthyl.

40. A method of claim 21 wherein the mammal is suffering from neuropathic pain.

* * * * *